United States Patent
Ginsburg et al.

(10) Patent No.: US 10,329,618 B2
(45) Date of Patent: Jun. 25, 2019

(54) DIAGNOSTIC MARKERS FOR PLATELET FUNCTION AND METHODS OF USE

(71) Applicant: Duke University, Durham, NC (US)

(72) Inventors: Geoffrey S. Ginsburg, Durham, NC (US); Joseph E. Lucas, Chapel Hill, NC (US); Thomas L. Ortel, Mebane, NC (US); Richard C. Becker, Durham, NC (US); Deepak Voora, Chapel Hill, NC (US); Jen-Tsan Chi, Chapel Hill, NC (US)

(73) Assignee: Duke University, Durham, NC (US)

( * ) Notice: Subject to any disclaimer, the term of this patent is extended or adjusted under 35 U.S.C. 154(b) by 6 days.

(21) Appl. No.: 14/426,430

(22) PCT Filed: Sep. 6, 2013

(86) PCT No.: PCT/US2013/058565
§ 371 (c)(1),
(2) Date: Mar. 6, 2015

(87) PCT Pub. No.: WO2014/039859
PCT Pub. Date: Mar. 13, 2014

(65) Prior Publication Data
US 2015/0322514 A1 Nov. 12, 2015

Related U.S. Application Data

(60) Provisional application No. 61/697,545, filed on Sep. 6, 2012.

(51) Int. Cl.
*C12Q 1/6883* (2018.01)
*A61K 31/60* (2006.01)
*G01N 33/68* (2006.01)
*G16H 50/30* (2018.01)

(52) U.S. Cl.
CPC ............ *C12Q 1/6883* (2013.01); *A61K 31/60* (2013.01); *G01N 33/6893* (2013.01); *C12Q 2600/106* (2013.01); *C12Q 2600/118* (2013.01); *C12Q 2600/158* (2013.01); *C12Q 2600/16* (2013.01); *G01N 2800/32* (2013.01); *G01N 2800/50* (2013.01); *G01N 2800/52* (2013.01); *G16H 50/30* (2018.01)

(58) Field of Classification Search
None
See application file for complete search history.

(56) References Cited

U.S. PATENT DOCUMENTS

2006/0003959 A1 1/2006 Burden et al.
2008/0009024 A1 1/2008 Christie

FOREIGN PATENT DOCUMENTS

WO WO 2012/024543 2/2012
WO WO 2012/113555 8/2012
WO WO 2014/039859 3/2014

OTHER PUBLICATIONS

Nurden et al. Journal of Thrombosis and Haemostasis. 2011. 9(Suppl. 1): 76-91.*
Sun et al. Journal of Thrombosis and Haemostasis. 2007. 5:146-154.*
Li. Identification of Aspirin Resistant Biomarkers Using Whole Blood Genome Profiling. Thesis. Aug. 31, 2009.*
Simon. Journal of Clinical Oncology. 2005. 23(29):7332-7341.*
Saito-Hisaminato et al. DNA Research. 2002. 9:35-45.*
Hoshikawa et al. Physical Genomics. 2003. 12: 209-219.*
Dillman et al. Toxicological Sciences. 2005. 87(1):306-314.*
Affymetrix Documents. Prepared by the Examiner on Jan. 12, 2017. Information retrieved on Jan. 12, 2017 from the internet: http://www.affymetrix.com/estore/index.jsp.*
Pascal et al. BMC Genomics. 2008. 9:246. (Year: 2008).*
Maier et al. FEBS Letters. 2009. 583:3966-3973. (Year: 2009).*
Chan et al. Drug Discovery & Development. 2006. 4 pages. (Year: 2006).*
Angiolillo et al., "Aspirin and clopidogrel: efficacy and resistance in diabetes mellitus," Best Practice & Research Clinical Endocrinology & Metabolism 23, 2009, (3):375-388.
Antithrombotic Trialist Collaboration, "Aspirin in the primary and secondary prevention of vascular disease collaborative meta-analysis of individual participant data from randomised trials," The Lancet 373, 2009, 1849-1860.
Becker et al., "Sex differences in platelet reactivity and response to low-dose aspirin therapy," Jama 295, 2006, (12): 1420-1427.
Bluteau et al., "Dysmegakaryopoiesis of FPD/AML pedigrees with constitutional RUNX1 mutations is linked to myosin II deregulated expression," Blood, 2012, 120:2708-2718.
Born, GV "Strong Inhibition by 2-Chloroadenosine of the Aggregation of Blood Platelets by Adenosine Diphosphate," Natur, 1964, e 202:95-96.
Bray et al., "Platelet glycoprotein Iib. Chromosomal localization and tissue expression," The Journal of Clinical Investigation 80, 1987, 1812-1817.
Bustin et al., "The MIQE guidelines: minimum information for publication of quantitative real-time PCR experiments.," Clinical Chemistry, 2009, 55:611-622.
Cameron et al., "The Runx genes: lineage-specific oncogenes and tumor suppressors," Oncogene 2004;23:4308-14.
Capodanno et al., "Pharmacodynamic Effects of Different Aspirin Dosing Regimens in Type 2 Diabetes Mellitus Patientes With Coronary Artery Disease / Clinical Perspective," Circulation: Cardiovascular Interventions 4, 2011, 180-187.

(Continued)

*Primary Examiner* — Joseph G. Dauner
(74) *Attorney, Agent, or Firm* — Michael Best & Friedrich LLP

(57) ABSTRACT

Disclosed herein are biomarkers of platelet function and methods for assessing platelet function in response to antiplatelet therapy and for determining a prognosis, diagnosis, or risk identification in a patient by detecting at least one biomarker of platelet function in the patient as well as determining amounts thereof. The biomarkers may be used to identify a patient as a candidate for treatment with an antiplatelet agent and to monitor and adjust antiplatelet therapy in a patient.

4 Claims, 54 Drawing Sheets

(56) References Cited

OTHER PUBLICATIONS

Carvalho et al., "High-Dimensional Sparce Factor Modeling: Applications in Gene Expression Genomics," J Am Stat Assoc 103, 2008, 1438-1456.
Cuisset et al., "Aspirin noncompliance is the major cause of "aspirin resistance" in patients undergoing coronary stenting," American Heart Journal 157, 2009, (5):889-893.
D'Agostino et al., "Validation of the Framingham coronary heart disease prediction scores: results of a multiple ethnic groups investigation," JAMA: the journal of the American Medical Association 286, 2001, 180-187.
Delong et al., "Comparing the areas under two or more correlated receiver operating characteristic curves: a nonparametric approach," Biometrics 44, 1988, 837-845.
Elagib et al., "RUNX1 and GATA-1 coexpression and cooperation in megakaryocytic differentiation," Blood 2003;101:4333-41.
Fallahi et al. "Aspirin insensitive thrombophilia: Transcript profiling of blood identifies platelet abnormalities and HLA restriction," Gene 2013, 520(2):131-8.
Faraday et al., "Heritability of platelet responsiveness to aspirin in activation pathways directly and indirectly related to cyclooxygenase-1," Circulation 115, 2007, (19):2490-2496.
Faraday et al., "Identification of a specific intronic PEAR1 gene variant associated with greater platelet aggregability and protein expression," Blood 118, 2011, 3367-3375.
Fitzgerald et al., "Endogenous biosynthesis of prostacyclin and thromboxane and platelet function during chronic administration of aspirin in man," J Clin Invest 71, 1983, (3):676-688.
Frelinger et al., "Association of Cyclooxygenase-1-Dependent and -Independent Platelet Function Assays With Adverse Clinical Outcomes in Aspirin-Treated Patients Presenting for Cardiac Catheterization," Circulation 120, 2009, (25):2586-2596.
Frelinger et al., "Residual arachidonic acid-induced platelet activation via an adenosine diphosphate-dependent but cyclooxygenase-1- and cyclooxygenase-2-independent pathway: a 700-patient study of aspirin resistance," Circulation 113, 2006, (25):2888-2896.
Gnatenko et al., "Transcript profiling of human platelets using microarray and serial analysis of gene expression," Blood 101, 2003, 2285-2293.
Goodall et al., "Transcription profiling in human plateles reveals LRRFIP1 as a novel protein regulating platelet function," Blood 116, 2010, 4646-4656.
Gurbel et al., "Evaluation of dose-related effects of aspirin on platelet function: results from the Aspirin-Induced Platelet Effect (ASPECT) study," Circulation 115, 2007, (25):3156-3164.
Gurbel et al., "Platelet function monitoring in patients with coronary artery disease," J Am Coll Cardiol 50, 2007, (19):1822-1834.
Hayward et al., "Platelet function analyzer (PFA)-100® closure time in the evaluation of platelet disorders and platelet function," Journal of Thrombosis and Haemostasis 4, 2006, (2):312-319.
Heagerty et al., "Time-dependent ROC curves for censored survival data and a diagnostic marker. Biometrics," Biometrics, 2000, 56:337-44.
Helgadottir et al., "A Common Variant on Chromosome 9p21 Affects the Risk of Myocardial Infarction," Science 316, 2007, 1491-1493.
Ho et al., "Linkage of a familial platelet disorder with a propensity to develop myeloid malignancies to human chromosome 21q22.1-22.2," Blood 1996;87:5218-24.
Homoncik et al., "Monitoring of aspirin (ASA) pharmacodynamics with the platelet function analyzer PFA-100," Thromb Haemost 83, 2000, (2):316-321.
Horne et al., "Association of variation in the chromosome 9p21 locus with myocardial infarction versus chronic coronary artery disease," Cir Cardiovasc Genet 1, 2008, 85-92.
International Search Report and Written Opinion for Application No. PCT/US2013/058565 dated Jan. 9, 2014 (15 pages).
Jalagadugula et al., "Regulation of platelet myosin light chain (MYL9) by RUNX1: implications for thrombocytopenia and platelet dysfunction in RUNX1 haplodeficiency," Blood 2010;116:6037-45.
Johnson et al., "Genome-wide meta-analyses identifies seven loci associated with platelet aggregation in response to agonists," Nat Genet 42, 2010, (7):608-613.
Kathiresan et al., "Genome-wide association of early-onset myocardial infarction with single nucleotide polymorphisms and copy number variants," Nat Genet 41, 2009, 334-341.
Kopp et al., "Inhibition of NF-kappa B by sodium salicylate and aspirin," Science 1994; 265:956-9.
Krishnan et al., "OFFgel-based multidimensional LC-MS/MS approach to the cataloguing of the human platelet proteome for an interactomic profile," Electrophoresis 32, 2011, 686-695.
Landgrebe et al., "Permutation-validated principal components analysis of microarray data," Genome Biology 3, 2002, (4):research0019.0011-research0019.0011.
Levanon et al., "Structure and regulated expression of mammalian RUNX genes," Oncogene 2004;23:4211-9.
Liu et al., "Identification of an N-terminal transactivation domain of Runx1 that separates molecular function from global differentiation function," The Journal of biological chemistry 2006;281:25659-69.
Livak et al., "Analysis of Relative Gene Expression Data Using Real-Time Quantitative PCR and the 2(-Delta Delta C(T)) Method," Methods, 2001, 25:402-408.
Lood et al., "Platelet transcriptional profile and protein expression in patients with systemic lupus erythematosus: up-regulation of the type I interferon system is strongly associated with vascular disease," Blood, 2010.
Lucas et al., "Latent factor analysis to discover pathway-associated putative segmental aneuploidies in human cancers," PLoS Comput Biol 6, 2010, e1000920.
Lucas et al., "Metaprotein expression modeling for label-free quantitative proteomics," BMC Bioinformatics, 2012, 13:74.
Mark et al., "Continuing evolution of therapy for coronary artery disease. Initial results from the era of coronary angioplasty," Circulation 89, 1994, 2015-2025.
Mathias et al., "A combined genome-wide linkage and association approach to find susceptibility loci for platelet function phenotypes in European American and African American families with coronary artery disease," BMC Medical Genomics 3, 2010, (1):22.
McCall et al., "Assessing affymetrix GeneChip microarray quality," BMC Bioinformatics, 2011, 12:137.
McPherson et al., "A common allele on chromosome 9 associated with coronary heart disease," Science 316, 2007, 1488-1491.
Mori et al., "Differential effect of aspirin on platelet aggregation in IDDM," Diabetes 41, 1992, (3):261-266.
Nagalla et al., "Platelet microRNA-mRNA coexpression profiles correlates with platelet reactivity," Blood 117, 2011, 5189-5197.
O'Donnell et al., "Genome-Wide Association Study for Coronary Artery Calcification With Follow-Up in Myocardial Infarction / Clinical Perspective," Circulation 124, 2011, 2855-2864.
Ohmori et al., "Aspirin resistance detected with aggregometry cannot be explained by cyclooxygenase activity: involvement of other signaling pathway(s) in cardiovascular events of aspirin-treated patients," J Thromb Haemost 4, 2006, (6):1271-1278.
Ortel et al., Ortel TL, "Assessment of primary hemostasis by PFA-100 analysis in a tertiary care center," Thromb Haemost 84, 2000, (1):93-97.
Paniccia et al., "Comparison of Different Methods to Evaluate the Effect of Aspirin on Platelet Function in High-Risk Patients With Ischemic Heart Disease Receiving Dual Antiplatelet Treatment," American Journal of Clinical Pathology 128, 2007, 143-149.
Patrono et al., "Drug insight: aspirin resistance—fact or fashion?," Nature clinical practice Cardiovascular medicine 4, 2007, (1):42-50.
Patrono et al., "Low dose aspirin and inhibition of thromboxane B2 production in healthy subjects," Thrombosis Research 17, 1980, (3-4):317-327.
Pencina et al., "Evaluating the added predictive ability of a new marker: from area under ROC curve to reclassification and beyond," Statistics in Medicine 27, 2008, 157-172, discussion 207-112.
Pencina et al., "Extensions of net reclassification improvement calculations to measure usefulness of new biomarkers," Statistics in Medicine 30, 2011, 11-21.

(56) References Cited

OTHER PUBLICATIONS

Perneby et al., "Dose- and time-dependent antiplatelet effects of aspirin," Thromb Haemost 95, 2006, (4):652-658.
Pham et al., "Gene-Expression Profiling for Rejection Surveillance after Cardiac Transplantation," New England Journal of Medicine 362, 2010, 1890-1900.
Phillips et al., "The platelet mebrane glycoprotein Iib-IIIa complex," Blood 71, 1988, 831-843.
Price et al., "Principal components analysis corrects for stratification in genome-wide association studies," Nat Genet 38, 2006, (8):904-909.
Pulcinelli et al., "Inhibition of platelet aggregation by aspirin progressively decreases in long-term treated patients," J Am Coll Cardiol 43, 2004, (6):979-984.
Raghavachari et al., "Amplified expression profiling of platelet transcriptome reveals changes in arginine metabolic pathways in patients with sickle cell disease," Circulation 115, 2007, 1551-1562.
Reilly et al., "Identification of ADAMTS7 as a novel locus for coronary atherosclerosis and association of ABO with myocardial infarction in the presence of coronary atherosclerosis: two genome-wide association studies," The Lancet, 2011, 377:383-92.
Roberts et al., "Inhibition of platelet function by a controlled release acetylsalicylic acid formulation—single and chronic dosing studies," Eur J Clin Pharmacol 27, 1984, (1):67-74.
Rosati et al., "A New Information System for Medical Practice," Arch Intern Med, 1975, 135:1017-1024.
Rosenberg et al., "Multicenter Validation of the Diagnostic Accuracy of a Blood-Based Gene Expression Test for Assessing Obstructive Coronary Artery Disease in Nondiabetic Patients," Annals of Internal Medicine 153, 2010, 425-434.
Rowley et al., "Genome-wide RNA-seq analysis of human and mouse platelet transcriptomes," Blood 2011;118:e101-11.
Rox et al., "PCR-Based amplification of platelet mRNA sequences obtained from small-scale platelet samples," Methods Mol Biol 2009;496:285-92.
Samani et al., "Genomewide association analysis of coronary artery disease," N Engl J Med 357, 2007, 443-453.
Santilli et al., "Platelet Cyclooxygenase Inhibition by Low-Dose Aspirin Is Not Reflected Consistently by Platelet Function Assays: Implications for Aspirin Resistance," Journal of the American College of Cardiology 53, 2009, (8):667-677.
Schedel et al., "Genome-wide platelet RNA profiling in clinical samples," Methods Mol Biol 2009;496:273-83.
Schwartz et al., "A new method for measuring inhibition of platelet function by nonsteroidal antiinflammatory drugs," Journal of Laboratory and Clinical Medicine 139, 2002, (4):227-233.
Shah et al., "High heritability of metabolomic profiles in families burdened with premature cardiovascular disease," Mol Syst Biol 5, 2009.
Shah et al., "Reclassification of cardiovascular risk using integrated clinical and molecular biosignatures: Design of rationale for the Measurement to Understand the Reclassification of Disease of Cabarrus and Kannapolis (MURDOCK) Horizon 1 cardiovascular Disease Study," American Heart Journal 160, 2010, 371-379 e2.
Sheppard et al., "The alpha adrenergic response of Down's syndrome platelets," The Journal of pharmacology and experimental therapeutics 1983;225:584-8.
Song et al., "Haploinsufficiency of CBFA2 causes familial thrombocytopenia with propensity to develop acute myelogenous leukaemia," Nature genetics 1999;23:166-75.
Soni, A. (2007) Aspirin Use among the Adult U.S. Noninstitutionalized Population, with and without Indicators of Heart Disease, 2005.
Stamova et al., "Identification and validation of suitable endogenous reference genes for gene expression studies in human peripheral blood," BMC Medical Genomics, 2009, 2:49.
Subramanian et al., "Gene set enrichment analysis: A knowledge-based approach for interpreting genome-wide expression profiles," Proceedings of the National Academy of Sciences of the United States of America 102, 2005, 15545-15550.
Sun et al., "Association of CBFA2 mutation with decreased platelet PKC-theta and impaired receptor-mediated activation of GPIIb-IIIa and pleckstrin phosphorylation: proteins regulated by CBFA2 play a role in GPIIb-IIIa activation," Blood 2004;103:948-54.
Sun et al., "Decreased platelet expression of myosin regulatory light chain polypeptide (MYL9) and other genes with platelet dysfunction and CBFA2/RUNX1 mutation: insights from platelet expression profiling," Journal of Thrombosis and Haemostasis 2007;5:146-54.
Telfer et al., "Expression and function of a stem cell promoter for the murine CBFalpha2 gene: distinct roles and regulation in natural killer and T cell development," Dev Biol 2001;229:363-82.
Thompson et al., "Size dependent platelet subpopulations: relationship of platelet volume to ultrastructure, enzymatic activity, and function," British Journal of Haematology 1982, 50:509-19.
Tijssen et al., "Genome-wide Analysis of Simultaneous GATA1/2, RUNX1, FLI1, and SCL Binding in Megakaryocytes Identifies Hematopoietic Regulators," Developmental Cell 2011;20:597-609.
Voora et al., "Aspirin Exposure Reveals Novel Genes Associated With Platelet Function and Cardiovascular Events," Journal of the Americna College of Cardiology, 2013, vol. 62, No. 14, 1267-76.
Voora et al., "Time-dependent changes in non-COX-1-dependent platelet function with daily aspirin therapy." J Thromb Thrombolysis, 2012, 33(3):246-257.
Wang et al., "BFRM: Bayesian factor regression modeling," Bulletin of the International Society of Bayesian Analysis 14, 2007, 4-5.
Wang et al., "Disruption of the Cbfa2 gene causes necrosis and hemorrhaging in the central nervous system and blocks definitive hematopoiesis," Proceedings of the National Academy of Sciences of the United States of America 1996;93:3444-9.
Wang et al., "Incidence of aspirin nonresponsiveness using Ultegra Rapid Platelet Function Assay-ASA," The American Journal of Cardiology 92, 2003, 1492-1494.
Wang et al., "Peakwide mapping on chromosome 3q13 identifies the kalirin gene as a novel candidate gene for coronary artery dissease," American journal of human genetics 80, 2007, 650-663.
Watkins et al., "A HaemAtlas: characterizing gene expression in differentiated human blood cells," Blood 113, 2009, e1-e9.
Williams et al., "Genetic regulation of platelet receptor expression and function: application in clinical practice and drug development," Arteriosclerosis, thrombosis, and vascular biology 30, 2010, (12):2372-2384.
Wingrove et al., "Correlation of Peripheral-Blood Gene Expression With the Extent of Coronary Artery Stenosis," Circ Cardiovasc Genet 1, 2008, 31-38.
Yee et al., "Aggregometry detects platelet hyperreactivity in healthy individuals," Blood 106, 2005, (8):2723-2729.
Yee et al., "Platelet hyperreactivity generalizes to multiple forms of stimulation," J Thromb Haemost 4, 2006, (9):2043-2050.
Yin et al., "The anti-inflammatory agents aspirin and salicylate inhibit the activity of I[kappa]B kinase-[beta]," Nature 1998;396:77-80.
Zhou et al., "Intracellular Erythrocyte PAF Acetylhydrolase 1 Inactivates Aspirin in Blood," Journal of Biological Chemistry 2011.
Zufferey et al., "Platelet reactivity is a stable and global phenomenon in aspirin-treated cardiovascular patients," Thromb Haemost 106, 2011, (3). doi:11-04-0226.

* cited by examiner

A

B

A continued

A continued

B

DIAGNOSTIC MARKERS FOR PLATELET FUNCTION AND METHODS OF USE

CROSS-REFERENCE TO RELATED APPLICATIONS

This patent application is a national stage filing under 35 U.S.C. 371 of International Patent Application No. PCT/US2013/058565, filed Sep. 6, 2013, which claims priority to U.S. Provisional Patent Application No. 61/697,545, filed Sep. 6, 2012, each of which is incorporated herein by reference in its entirety.

STATEMENT OF GOVERNMENT INTEREST

This invention was made with government support under federal grant numbers GM091083-01 and 5T32HL007101 awarded by National Institutes of Health, 5UL1RR024128 awarded by National Center for Research Resources, 5RC1GM091083 awarded by the National Institutes of General Medical Sciences, and 5U01DD000014-06 awarded by the Centers for Disease Control and Prevention. The U.S. Government has certain rights to this invention.

TECHNICAL FIELD

The present invention relates to methods for assessing platelet function and for determining a prognosis, diagnosis, or risk identification of cardiovascular disease in a patient by detecting at least one biomarker of platelet function in the patient as well as determining amounts thereof. The biomarkers may be used to identify a patient suffering from cardiovascular disease as a candidate for treatment with an antiplatelet agent and to monitor and adjust antiplatelet therapy in a patient.

BACKGROUND

Methods of identifying individuals at risk for coronary artery disease (CAD) mortality, primarily due to platelet mediated cardiovascular events such as myocardial infarction (MI), are a priority for reducing the burden of cardiovascular disease. To identify novel risk factors, genome-wide surveys of allelic variation, structural variation, and gene expression can identify loci associated with CAD, though not all are subsequently associated with cardiovascular events.

Aspirin is a potent inhibitor of COX-1 and an inhibitor of platelet function. Aspirin is one of the most commonly prescribed medications for the prevention of cardiovascular events, suggesting that aspirin interacts with biological pathways that may underlie these events. Platelet function assays can be used as surrogates for the effects of aspirin and demonstrate variability, reproducibility, and heritability, despite complete suppression of platelet COX-1. However, platelet function testing is not widely available primarily due to technical complexity, such as the need for specialized equipment and trained personnel. For example, point-of-care tests require testing to be completed within hours of phlebotomy and thus are out of reach for the vast majority of outpatients on aspirin. Further, most patients taking aspirin for chronic prevention are outpatients where results at the point-of-care are not required. Instead, testing in central laboratories would be sufficient for determining aspirin response in the outpatient setting.

It would be beneficial if aspirin could be used as a probe in conjunction with whole blood gene expression profiling to elucidate novel biological pathways associated with platelet function in response to aspirin and cardiovascular outcomes.

SUMMARY

The present disclosure is directed to a method for providing a diagnosis, prognosis or risk classification to a subject. The method comprises obtaining a biological sample from the subject; determining the gene expression level of at least one a biomarker of platelet function in the biological sample from the subject; and comparing the gene expression level of the at least one biomarker of platelet function in the sample to a reference level of the at least one biomarker of platelet function. A gene expression level of the at least one biomarker of platelet function in the sample greater than the reference level of the at least one biomarker of platelet function identifies the subject as having a condition associated with cardiovascular disease or who is at risk of having a condition associated with cardiovascular disease. A gene expression level of the at least one biomarker of platelet function in the sample less than the reference level of the at least one biomarker of platelet function identifies the subject as having an increased risk of excessive bleeding. The method may optionally include administering an antiplatelet agent to the subject identified as having a condition associated with cardiovascular disease or who is at risk of having a condition associated with cardiovascular disease, or administering an anticoagulant to the subject identified as having an increased risk of excessive bleeding. An effective dosage of antiplatelet agent may be administered. The reference level of the at least one biomarker of platelet function may be the level of the at least one biomarker of platelet function in a control sample. The control sample may be from a healthy subject or a subject without cardiovascular disease. The reference level of the at least one biomarker of platelet function may be the cutoff value of the at least one biomarker of platelet function determined by measuring a change in gene expression levels between biological samples obtained before and after aspirin treatment of a healthy patient group or patients without cardiovascular disease. The reference level of the at least one biomarker of platelet function may be the cutoff values of the at least one biomarker of platelet function determined by receiver operating characteristic (ROC) analysis from biological samples from patients with and without cardiovascular disease. The level of the at least one biomarker of platelet function may be at least about 1.1 fold change compared to the reference level of the at least one biomarker of platelet function. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The biomarker of platelet function may be ITGA2B. The biomarker of platelet function may be RUNX1. The gene expression levels of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79 may be determined. The gene expression level of all of the genes may total an absolute change of an increase of at least 1.6 compared to reference level of all of the genes. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700, 462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method for providing a diagnosis, prognosis or risk classification to a subject having a condition associated with cardiovascular disease or who is at risk of having a condition associated with cardiovascular disease. The method comprises obtaining a biological sample from the subject; determining the gene expression level of at least one a biomarker of platelet function in the biological sample from the subject; and comparing the gene expression level of the at least one biomarker of platelet function in the sample to a reference level of the at least one biomarker of platelet function. A gene expression level of the at least one biomarker of platelet function in the sample greater than the reference level of the at least one biomarker of platelet function identifies the subject as having a condition associated with cardiovascular disease or who is at risk of having a condition associated with cardiovascular disease. The method optionally includes administering an antiplatelet agent to the subject identified as having a condition associated with cardiovascular disease or who is at risk of having a condition associated with cardiovascular disease. An effective dosage of antiplatelet agent may be administered. The reference level of the at least one biomarker of platelet function may be the level of the at least one biomarker of platelet function in a control sample. The control sample may be from a healthy subject or a subject without cardiovascular disease. The reference level of the at least one biomarker of platelet function may be the cutoff value of the at least one biomarker of platelet function determined by measuring a change in gene expression levels between biological samples obtained before and after aspirin treatment of a healthy patient group or patients without cardiovascular disease. The reference level of the at least one biomarker of platelet function may be the cutoff values of the at least one biomarker of platelet function determined by receiver operating characteristic (ROC) analysis from biological samples from patients with and without cardiovascular disease. The level of the at least one biomarker of platelet function may be at least about 1.1 fold change compared to the reference level of the at least one biomarker of platelet function. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The biomarker of platelet function may be ITGA2B. The biomarker of platelet function may be RUNX1. The gene expression levels of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79 may be determined. The gene expression level of all of the genes may total an absolute change of an increase of at least 1.6 compared to reference level of all of the genes. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700, 462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method of determining or predicting platelet function response to an antiplatelet agent in a subject to identify the subject as a candidate for antiplatelet therapy. The method comprises obtaining a biological sample from the subject; determining the gene expression level of at least one biomarker of platelet function in the biological sample from the subject; comparing the gene expression level of the at least one biomarker of platelet function in the biological sample to a reference level of the at least one biomarker of platelet function; and identifying the subject as a candidate for antiplatelet therapy if the gene expression level of the at least one biomarker of platelet function in the sample is higher than the reference level of the at least one biomarker of platelet function. The method optionally includes administering an antiplatelet agent to the subject identified as a candidate for treatment with an antiplatelet agent. An effective dosage of antiplatelet agent may be administered. The reference level of the at least one biomarker of platelet function may be the level of the at least one biomarker of platelet function in a control sample. The control sample may be from a healthy subject or a subject without cardiovascular disease. The reference level of the at least one biomarker of platelet function may be the cutoff value of the at least one biomarker of platelet function determined by measuring a change in gene expression levels between biological samples obtained before and after aspirin treatment of a healthy patient group or patients without cardiovascular disease. The reference level of the at least one biomarker of platelet function may be the cutoff values of the at least one biomarker of platelet function determined by receiver operating characteristic (ROC) analysis from biological samples from patients with and without cardiovascular disease. The level of the at least one biomarker of platelet function may be at least about 1.1 fold change compared to the reference level of the at least one biomarker of platelet function. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The biomarker of platelet function may be ITGA2B. The biomarker of platelet function may be RUNX1. The gene expression levels of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79 may be determined. The gene expression level of all of the genes may total an absolute change of an increase of at least 1.6 compared to reference level of all of the genes. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700, 462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method for monitoring the antiplatelet treatment of a subject. The method comprises obtaining a biological sample from the subject, wherein the subject is under a current treatment regimen of an antiplatelet agent; determining the gene expression level of at least one biomarker of platelet function in the biological sample; comparing the gene expression level of the at least one biomarker of platelet function in the biological sample to a reference level of the at least one biomarker of platelet function; and modifying the course of treatment based upon the gene expression level of the at least one biomarker of platelet function in the sample. If the gene expression level of the at least one biomarker of platelet function in the sample is the same or higher as the reference level of the at least one biomarker of platelet function, then a different antiplatelet agent is prescribed. If the gene expression level of the at least one biomarker of platelet function is lower than the reference level of the at least one biomarker of platelet function, then the current treatment regimen of the antiplatelet agent is continued or reduced. The subject may be suffering or will suffer from a condition associated with cardiovascular disease. The method may further comprise continuing to monitor the gene expression levels of the at least one biomarker of platelet function by repeating said steps after the course of treatment is modified. The reference level of the at least one biomarker of platelet function may be the level of the at least one biomarker of platelet function in a control sample. The control sample may be from a healthy subject or a subject without cardiovascular disease. The reference level of the at least one biomarker of platelet function may be the cutoff value of the at least one biomarker of platelet function determined by measuring a change in gene expression levels between biological samples obtained before and after aspirin treatment of a healthy patient group or patients without cardiovascular disease. The reference level of the at least one biomarker of platelet function may be the cutoff values of the at least one biomarker of platelet function determined by receiver operating characteristic (ROC) analysis from biological samples from patients with and without cardiovascular disease. The level of the at least one biomarker of platelet function may be at least about 1.1 fold change compared to the reference level of the at least one biomarker of platelet function. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The biomarker of platelet function may be ITGA2B. The biomarker of platelet function may be RUNX1. The gene expression levels of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79 may be determined. The gene expression level of all of the genes may total an absolute change of an increase of at least 1.6 compared to reference level of all of the genes. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700, 462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method of identifying a subject as a candidate for treatment with an antiplatelet agent. The method comprises obtaining a biological sample from the subject; determining the gene expression level of RUNX1 in the biological sample from the subject; comparing the gene expression level of RUNX1 in the biological sample to a reference level of RUNX1; and identifying the subject as a candidate for treatment with an antiplatelet agent if the gene expression level of RUNX1 in the sample is higher than the reference level of RUNX1. The method may optionally include administering an antiplatelet agent to the subject identified as a candidate for treatment with an antiplatelet agent. The gene expression level of RUNX1 RNA transcript may be measured. The subject may be identified as a candidate for treatment with an antiplatelet agent if the RUNX1 RNA transcript is a P1-driven RUNX1 transcript and the level of RUNX1 RNA transcript is higher than the reference level; or if the RUNX1 RNA transcript is a P2-driven RUNX1 transcript and the level of RUNX1 RNA transcript is lower than the reference level. An effective dosage of antiplatelet agent may be administered. The subject may be suffering or will suffer from a condition associated with cardiovascular disease. The reference level of RUNX1 may be the level of RUNX1 in a control sample. The control sample may be from a healthy subject or a subject without cardiovascular disease. The reference level of RUNX1 may be the RUNX1 cutoff value determined by measuring a change in gene expression levels between biological samples obtained before and after aspirin treatment of a healthy patient group or patients without cardiovascular disease. The reference level of RUNX1 may be the RUNX1 cutoff values determined by receiver operating characteristic (ROC) analysis from biological samples from patients with and without cardiovascular disease. The level of the RUNX1 RNA transcript may be at least a 1.33 fold change compared to the reference level of RUNX1. The level of the RUNX1 RNA transcript may be at least a 1.33 fold increase compared to the reference level of RUNX1. The level of the RUNX1 RNA transcript may be at least a 1.33 fold decrease compared to the reference level of RUNX1. The method may further comprising determining the gene expression level of at least one biomarker of platelet function, and comparing the level of the at least one biomarker of platelet function to a reference gene expression level for the at least one biomarker of platelet function, wherein the at least one biomarker of platelet function is selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79. The at least one biomarker of platelet function may be ITGA2B. The gene expression levels of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79 may be determined. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700,462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method for monitoring the antiplatelet treatment of a subject. The method comprises obtaining a biological sample from the subject, the subject is under a current treatment regimen of an antiplatelet agent; determining the gene expression level of RUNX1 in the biological sample from the subject; comparing the gene expression level of RUNX1 in the biological sample to a reference level of RUNX1; and modifying the course of treatment based upon the gene expression level of RUNX1 in the sample. If the gene expression level RUNX1 in the sample is the same or higher as the reference level of RUNX1, then a different antiplatelet agent is prescribed. If the gene expression level RUNX1 is lower than the reference level of RUNX1, then the current treatment regimen of the antiplatelet agent is continued or reduced. The gene expression level of RUNX1 RNA transcript may be measured. If the RUNX1 RNA transcript is a P1-driven RUNX1 transcript and the level of RUNX1 RNA transcript is higher than the reference level or if the RUNX1 RNA transcript is a P2-driven RUNX1 transcript and the level of RUNX1 RNA transcript is lower than the reference level, then the current treatment with antiplatelet agent is continued or reduced. If the RUNX1 RNA transcript is a P1-driven RUNX1 transcript and the level of RUNX1 RNA transcript is lower than the reference level or if the RUNX1 RNA transcript is a P2-driven RUNX1 transcript and the level of RUNX1 RNA transcript is higher than the reference level, then a different antiplatelet agent is prescribed. The method may further comprise continuing to monitor the gene expression levels of RUNX1 by repeating said steps after the course of treatment is modified. The subject may be suffering or will suffer from a condition associated with cardiovascular disease. The reference level of RUNX1 may be the level of RUNX1 in a control sample. The control sample may be from a healthy subject or a subject without cardiovascular disease. The reference level of RUNX1 may be the RUNX1 cutoff value determined by measuring a change in gene expression levels between biological samples obtained before and after aspirin treatment of a healthy patient group or patients without cardiovascular disease. The reference level of RUNX1 may be the RUNX1 cutoff values determined by receiver operating characteristic (ROC) analysis from biological samples from patients with and without cardiovascular disease. The level of the RUNX1 RNA transcript may be at least a 1.33 fold change compared to the reference level of RUNX1. The level of the RUNX1 RNA transcript may be at least a 1.33 fold increase compared to the reference level of RUNX1. The level of the RUNX1 RNA transcript may be at least a 1.33 fold decrease compared to the reference level of RUNX1. The method may further comprising determining the gene expression level of at least one biomarker of platelet function, and comparing the level of the at least one biomarker of platelet function to a reference gene expression level for the at least one biomarker of platelet function, wherein the at least one biomarker of platelet function is selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79. The at least one biomarker of platelet function may be ITGA2B. The gene expression levels of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79 may be determined. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700,462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method for providing a diagnosis, prognosis or risk classification to a subject having a condition associated with cardiovascular disease or who is at risk of having a condition associated with cardiovascular disease. The method comprises obtaining a biological sample from the subject; performing at least one platelet function assay to generate a platelet function result for the sample; determining a platelet function score (PFS) for the sample from the platelet function result of step (b) using principal components analysis; and comparing the PFS for the sample against a reference PFS, wherein a PFS for the sample greater than the reference PFS identifies the subject as having a condition associated with cardiovascular disease or who is at risk of having a condition associated with cardiovascular disease. The method may optionally include administering an antiplatelet agent to the subject identified as having a condition associated with cardiovascular disease or who is at risk of having a condition associated with cardiovascular disease. An effective dosage of antiplatelet agent may be administered. More than one platelet function assay may be performed. The method may further comprise determining the gene expression level of at least one biomarker of platelet function, and comparing the level of the at least one biomarker of platelet function to a reference gene expression level for the at least one biomarker of platelet function. The reference gene expression level of the at least one biomarker of platelet function may be the level of the at least one biomarker of platelet function in a control sample. The control sample may be from a healthy subject or a subject without cardiovascular disease. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700,462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method of identifying a subject suffering or will suffer from cardiovascular disease as a candidate for treatment with an antiplatelet agent. The method comprises obtaining a biological sample from the subject; performing at least one platelet function assay to generate a platelet function result for the sample; determining a platelet function score (PFS) for the sample from the platelet function result of step (b) using principal components analysis; comparing the PFS for the sample against a reference PFS; and identifying the subject as a candidate for treatment with an antiplatelet agent if the PFS for the sample is greater than the reference PFS. The method may optionally include administering an antiplatelet agent to the subject identified as a candidate for treatment with an antiplatelet agent. An effective dosage of antiplatelet agent may be administered. More than one platelet function assay may be performed. The method may further comprise determining the gene expression level of at least one biomarker of platelet function, and comparing the level of the at least one biomarker of platelet function to a reference gene expression level for the at least one biomarker of platelet function. The reference gene expression level of the at least one biomarker of platelet function may be the level of the at least one biomarker of platelet function in a control sample. The control sample may be from a healthy subject or a subject without cardiovascular disease. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700,462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a method for monitoring the antiplatelet treatment of a subject. The method comprises obtaining a biological sample from the subject, wherein the subject is under a current treatment regimen of an antiplatelet agent; performing at least one platelet function assay to generate a platelet function result for the sample; determining a platelet function score (PFS) for the sample from the platelet function result of step (b) using principal components analysis; comparing the PFS for the sample against a reference PFS; and modifying the course of treatment based upon the PFS for the sample, wherein if the PFS for the sample is the same or higher as a reference PFS, then a different antiplatelet agent is prescribed, and wherein if PFS for the sample is lower than the reference PFS, then the current treatment regimen of the antiplatelet agent is continued or reduced. The subject may be suffering or will suffer from a condition associated with cardiovascular disease. The method may further comprise continuing to monitor the PFS by repeating said steps after the course of treatment is modified. More than one platelet function assay may be performed. The method may further comprise determining the gene expression level of at least one biomarker of platelet function, and comparing the level of the at least one biomarker of platelet function to a reference gene expression level for the at least one biomarker of platelet function. The reference gene expression level of the at least one biomarker of platelet function may be the level of the at least one biomarker of platelet function in a control sample. The control sample may be from a healthy subject or a subject without cardiovascular disease. The at least one biomarker of platelet function may be selected from the group consisting of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79 and RUNX1. The antiplatelet agent may include at least one of aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700,462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof. The antiplatelet agent may be aspirin. The cardiovascular disease may be coronary artery disease, cardiovascular death, sudden cardiac death, stroke, transient ischemic attack or thrombosis. The subject may be human. The gene expression levels may be determined by measuring the RNA or protein levels of the biomarker of platelet function. The biological sample of a subject may be selected from a tissue sample, bodily fluid, whole blood, plasma, serum, urine, bronchoalveolar lavage fluid, and a cell culture suspension or fraction thereof. The biological sample of a subject may be blood plasma or blood serum.

The present disclosure is directed to a biomarker of platelet function for use in said methods. The biomarker includes at least one gene selected from the group consisting of the genes listed in FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, C6ORF79, RUNX1, and combinations thereof. The biomarker may include FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79. The biomarker may consist of FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF79. The biomarker may include the gene ITGA2B. The biomarker may include RUNX1.

The present disclosure is directed to a kit comprising a reagent capable of binding said biomarker, a reference standard indicating a reference gene expression biomarker level, and instructions for use.

DETAILED DESCRIPTION

Figure 1:
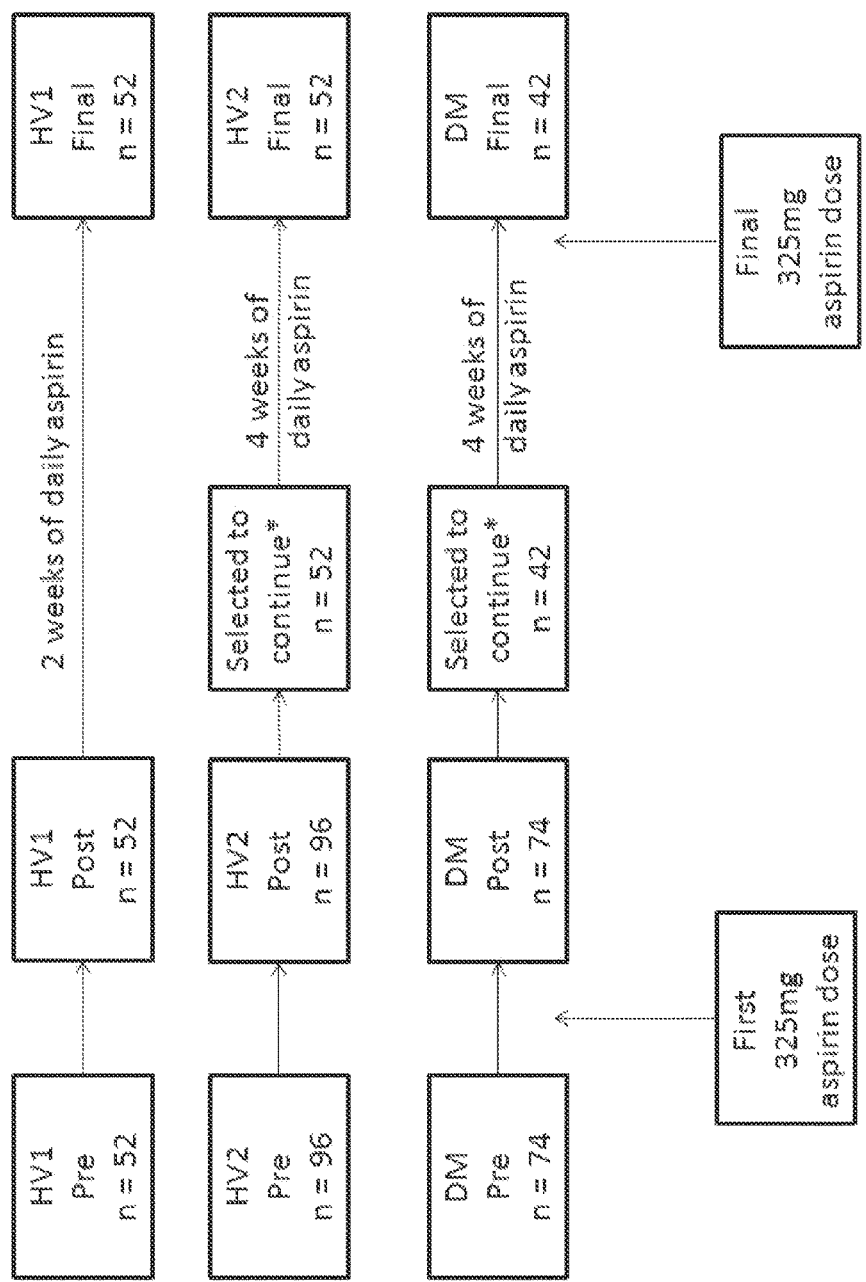
FIG. 1 shows an overview study flow for the two healthy volunteer cohorts (HV1 and HV2) and diabetic cohort (DM). All subjects had platelet function measurements made before (Pre) and 3 hrs after (Post) aspirin. All HV1 subjects and selected HV2 and DM subjects continued with daily aspirin therapy and returned for a Final assessment of platelet function made 3-5 hrs after the final aspirin dose. *see selection protocol in Example 1.

Platelets are normally involved in a number of physiological processes such as adhesion, for example, to cellular and non-cellular entities, aggregation, for example, for the purpose of forming a blood clot, and release of factors such as growth factors (e.g., platelet-derived growth factor (PDGF)) and platelet granular components. The present disclosure provides a method of assessing the platelet function in a subject in response to antiplatelet therapy using biomarkers of platelet function and/or a platelet function score. Lower levels or reductions in gene expression levels of the biomarkers of platelet function may be indicative of a favorable platelet function response to antiplatelet therapy and/or lower cardiovascular risk.

The present invention is directed to analyzing the levels of at least one biomarker of platelet function and/or determining a PFS to assess or predict platelet function in response to antiplatelet therapy in a patient. The present invention is also directed to analyzing the levels of at least one biomarker of platelet function and/or determining a PFS to provide diagnosis, prognosis or risk classification to a subject who may or may not have been treated with an antiplatelet therapy and to identify, diagnose and treat a patients in need thereof with antiplatelet therapy. The methods may be used to diagnose and monitor a patient who may have or is at risk of having cardiovascular disease or thrombosis.

This method differs over previous methods by using at least one gene from a group of genes, known as the aspirin response signature (ARS), in combination with RUNX1, that have been shown to change expression due to treatment with aspirin. These biomarkers, either alone or in combination, may be used to distinguish patients who will respond to antiplatelet therapy from patients who will not respond as well as to monitor the effectiveness of antiplatelet therapy in a subject that is currently undergoing antiplatelet therapy. The use of the biomarkers of platelet function may be further combined with a PFS or other clinical or laboratory data to provide accurate and precise diagnosing in point-of care or laboratory settings, and subsequent treatment of subjects, such as those suffering from cardiovascular disease or thrombosis, with antiplatelet therapy.

One aspect of the present disclosure provides a method of assessing the effectiveness of treating a subject at risk for cardiovascular disease (e.g., myocardial infarction, stroke, etc.) or thrombosis with a platelet-inhibiting agent comprising, consisting of, or consisting essentially of obtaining a biological sample from the subject, isolating RNA from the sample to generate a gene expression pattern, comparing the gene expression pattern of the subject against a reference or control, and administering to the subject at least one additional platelet-inhibiting agent if there is an increased gene expression of factors associated with platelet function score (PFS) as compared to the control.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "administration" or "administering," as used herein, refers to providing, contacting, and/or delivery of an anti-platelet agent by any appropriate route to achieve the desired effect. These agents may be administered to a subject in numerous ways including, but not limited to, orally, ocularly, nasally, intravenously, topically, as aerosols, suppository, etc. and may be used in combination.

The term "antiplatelet agent", "antiplatelet inhibitor", "platelet inhibiting agent", "platelet function inhibitors" or "antiplatelet drug" as used interchangeably herein refers to a member of a class of pharmaceuticals that decrease platelet function and inhibit thrombus formation. Antiplatelet agents impair the ability of mature platelets to perform their normal physiological roles (i.e., their normal function). Antiplatelet agents are most effective in the arterial circulation, where anticoagulants have little effect. However, antiplatelet agents may also be used in the venous system for prevention of thrombosis.

The term "biomarker" as used herein refers to any quantifiable biological component that is unique to a particular physiological condition (e.g., cardiovascular disease). A biomarker may be a gene, an mRNA resulting from transcription of a gene or a protein resulting from translation of an mRNA. A measureable increase or decrease, of a biomarker level, relative to a control, such as an individual, group of individuals or populations, or alternatively, relative to subjects with cancer, may provide a diagnosis of a particular physiological condition.

The term "cardiovascular disease", "cardiovascular disorder" or "CVD" as used interchangeably herein refers to a number of diseases that affect the heart and circulatory system. Cardiovascular disease encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

The term "confidence interval" or "CI" as used herein refers to an interval estimate of a population parameter used to indicate the reliability of an estimate. The confidence interval refers to the region containing the limits or band of a parameter with an associated confidence level that the bounds are large enough to contain the true parameter value. The bands may be single-sided to describe an upper or lower limit or double sided to describe both upper and lower limits. The region gives a range of values, bounded below by a lower confidence limit and from above by an upper confidence limit, such that one can be confident (at a pre-specified level such as 95% or 99%) that the true population parameter value is included within the confidence interval. Confidence intervals may be formed for any of the parameters used to describe the characteristic of interest. Confidence intervals may be used to estimate the population parameters from the sample statistics and allow a probabilistic quantification of the strength of the best estimate. A preferred confidence interval may be at least 90%, at least 91%, at least 92%, at least 93%, at least 94%, at least 95%, at least 96%, at least 97%, at least 98%, or at least 99%.

The term "control subject" as used herein means a healthy subject, i.e. a subject having no clinical signs or symptoms of cardiovascular disease. The control subject is clinically evaluated for otherwise undetected signs or symptoms of cardiovascular disease, which evaluation may include routine physical examination and/or laboratory testing.

"Correlation coefficient" as used herein means a significant correlation that may be determined by any suitable statistic method. For example, the correlation coefficient may be Spearman's rank correlation coefficient (also known as "Spearman's rho" and "Spearman's rho correlation coefficient"), which is a non-parametric measure of statistical dependence between two variables. Spearman's rho assesses how well the relationship between two variables can be described using a monotonic function. If there are no repeated data values, a perfect Spearman correlation of +1 or −1 occurs when each of the variables is a perfect monotone function of the other. A highly significant correlation is indicated when Spearman's rho is at least 0.50, preferably at least 0.60, more preferably at least 0.70, even more preferably at least 0.80, yet more preferably at least 0.85, even more preferably at least 0.90. Spearman's rho may be between at least approximately 0.15 and 0.99, between at least approximately 0.20 and 0.80, between at least approximately 0.30 and 0.50, or between at least approximately 0.55 and 0.60. Most preferably, for two markers, Spearman's rho is at least approximately 0.50, at least approximately 0.55, at least approximately 0.60, at least approximately 0.65, at least approximately 0.70, at least approximately 0.75, at least approximately 0.80, at least approximately 0.85, at least approximately 0.90, at least approximately 0.91, at least approximately 0.92, at least approximately 0.93, at least approximately 0.94, at least approximately 0.95, at least approximately 0.96, at least approximately 0.97, at least approximately 0.98, or at least approximately 0.99. The gene expression of at least one biomarker and platelet function may have Spearman's rho of at least approximately 0.15, at least approximately 0.2, at least approximately 0.25, at least approximately 0.30, at least approximately 0.35, at least approximately 0.40, at least approximately 0.45, or at least approximately 0.50.

The term "effective dosage" or "therapeutically effective dosage" as used interchangeably herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of platelets and the like. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the anti-platelet agent may be administered at various times during the course of treatment of the subject. The times of administration and dosages used will depend on several factors, such as the goal of treatment (e.g., treating v. preventing), condition of the subject, etc. and can be readily determined by one skilled in the art.

"Interquartile range" or "IQR" as used herein means a measure of statistical dispersion, being equal to the difference between the upper and lower quartiles, IQR=Q3−Q1.

The term "normal control" or "healthy control" as used herein means a sample or specimen taken from a subject, or an actual subject who does not have cardiovascular disease, or is not at risk of developing cardiovascular disease.

The term "predetermined cutoff" and "predetermined level" as used herein means an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

The term "reference activity level" or "reference" as used herein means an activity level of at least one biomarker of platelet function in a sample group that serves as a reference against which to assess the activity level in an individual or sample group. For example, the reference activity level may be the activity of the at least one biomarker of platelet function in a control sample from patients that are healthy, patients that do not have cardiovascular disease, or patients that have cardiovascular but have not suffered death or myocardial infarction (MI).

The term "risk assessment," "risk classification," "risk identification," or "risk stratification" as used herein interchangeably, means an evaluation of factors including biomarkers, to predict the risk of occurrence of future events including disease onset or disease progression, so that treatment decisions regarding the subject may be made on a more informed basis.

"Receiver Operating Characteristic" or "ROC" curve analysis refers to an analysis that is generally known in the biological arts for the determination of the ability of a test to discriminate one condition from another, e.g. to determine the performance of each marker in assessing platelet function and/or identifying cardiovascular disease. A description of ROC analysis is described in P. J. Heagerty et al., Biometrics 56:337-44 (2000), the disclosure of which is hereby incorporated by reference in its entirety.

The term "sample," "test sample," "specimen," "biological sample," "sample from a subject," or "subject sample" as used herein interchangeably, means a sample or isolate of blood, tissue, urine, serum, plasma, amniotic fluid, cerebrospinal fluid, placental cells or tissue, endothelial cells, leukocytes, or monocytes, can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art.

The term also means any biological material being tested for and/or suspected of containing an analyte of interest such as at least one biomarker of platelet function. The sample may be any tissue sample taken or derived from the subject. In some embodiments, the sample from the subject may comprise protein. Any cell type, tissue, or bodily fluid may be utilized to obtain a sample. Such cell types, tissues, and fluid may include sections of tissues such as biopsy and autopsy samples, frozen sections taken for histological purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

Methods well-known in the art for collecting, handling and processing urine, blood, serum and plasma, and other body fluids, are used in the practice of the present disclosure. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples, a pre-processed archived sample, etc.), pretreatment of the sample is an option that can be performed for mere convenience (e.g., as part of a protocol on a commercial platform). The sample may be used directly as obtained from the subject or following pretreatment to modify a characteristic of the sample. Pretreatment may include extraction, concentration, inactivation of interfering components, and/or the addition of reagents.

The term "risk of having a cardiovascular disease" or "cardiovascular disease risk" of a subject as used herein means an evaluation of factors including biomarkers, to predict the risk of occurrence of cardiovascular disease including increased probability of cardiovascular disease onset, cardiovascular disease progression, and occurrence/severity of clinical symptoms associated with cardiovascular disease.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human. In some embodiments, the subject or subject may be a human or a non-human. In some embodiments, the subject may be a human subject at risk for developing or already having cardiovascular disease. In some embodiments, the subject may be a human subject at risk of bleeding or excessive bleeding.

The term "thrombosis" as used herein refers to the formation or presence of coagulated blood or a thrombus attached at the site of formation or has embolized to other parts of the circulation system.

The term "thrombus" as used herein means an aggregation of blood factors, primary platelets and fibrin with entrapment of cellular elements, frequently causing vascular obstruction at the point of its formation. One of skill would understand there are very many types of thrombus including, but not limited to, blood platelet, fibrin, and white cell. Conditions associated with a thrombus include pulmonary embolism, thrombosis of the kidneys, myocardial infarction, deep venous thrombosis, venous thrombosis, arterial thrombosis, bacterial embolus, portal vein thrombosis (liver), jugular vein thrombosis, Budd-Chiari syndrome (blockage of the hepatic vein or inferior vena cava), Paget-Schroetter disease, neurovascular disorder and stroke.

2. METHODS FOR PROVIDING A DIAGNOSIS, PROGNOSIS OR RISK CLASSIFICATION TO A SUBJECT

The present invention is directed to a method for providing a diagnosis, prognosis or risk classification to a subject. The subject may be suffering or will be suffering from cardiovascular disease, thrombosis, or at risk of bleeding or excessive bleeding.

The method includes the steps of (a) obtaining a biological sample from the subject; (b) determining the gene expression level of at least one biomarker of platelet function in the biological sample from the subject; and (c) comparing the gene expression level of the at least one biomarker of platelet function in the sample to a reference level of at least one biomarker of platelet function. If the gene expression level of the at least one biomarker of platelet function in the sample is greater than the reference level of the at least one biomarker of platelet function, the subject is identified as having or at risk of having a condition associated with cardiovascular disease or thrombosis. If the gene expression level of the at least one biomarker of platelet function in the sample is less than the reference level of the at least one biomarker of platelet function, the subject is identified as having an increased risk of bleeding or excessive bleeding. The method includes administering or adjusting an antiplatelet agent to the subject identified as having or at risk of having a condition associated with cardiovascular disease or thrombosis or withdrawing or adjusting an antiplatelet agent to the subject identified as having an increased risk of bleeding or excessive bleeding.

3. METHODS FOR PROVIDING A DIAGNOSIS, PROGNOSIS OR RISK CLASSIFICATION TO A SUBJECT HAVING OR AT RISK OF HAVING CARDIOVASCULAR DISEASE

The present invention is directed to a method for providing a diagnosis, prognosis or risk classification to a subject having a condition associated with cardiovascular disease or who is at risk of having a condition associated with cardiovascular disease. The method may include the steps of (a) obtaining a biological sample from the subject; (b) determining the gene expression level of at least one biomarker of platelet function in the biological sample from the subject; and (c) comparing the gene expression level of the at least one biomarker of platelet function in the sample to a reference level of the at least one biomarker of platelet function. If the gene expression level of the at least one biomarker of platelet function in the sample is greater than the reference level of the at least one biomarker of platelet function, the subject is identified as having a condition associated with cardiovascular disease or who is at risk of having a condition associated with cardiovascular disease. The method includes administering an antiplatelet agent to the subject identified as having a condition associated with cardiovascular disease or who is at risk of having a condition associated with cardiovascular disease.

The method may include performing at least one platelet function assay to generate a platelet function result for the sample, determining a platelet function score (PFS) for the sample from the platelet function result using principal components analysis, and comparing the PFS for the sample against a reference PFS. If the PFS for the sample is greater than the reference PFS, the subject is identified as having a condition associated with cardiovascular disease or who is at risk of having a condition associated with cardiovascular disease;

4. METHOD OF DETERMINING OR PREDICTING PLATELET FUNCTION RESPONSE TO AN ANTIPLATELET AGENT

The present invention is directed to a method of determining or predicting platelet function response to an antiplatelet agent in a subject to identify the subject as a candidate for antiplatelet therapy. The method includes the steps of (a) obtaining a biological sample from the subject; (b) determining the gene expression level of at least one biomarker of platelet function in the biological sample from the subject; (c) comparing the gene expression level of the at least one biomarker of platelet function in the biological sample to a reference level of the at least one biomarker of platelet function; (d) identifying the subject as a candidate for antiplatelet therapy if the gene expression level of the at least one biomarker of platelet function in the sample is higher than the reference level of the at least one biomarker of platelet function; and (e) administering an antiplatelet agent to the subject identified as a candidate for treatment with an antiplatelet agent.

5. METHODS OF IDENTIFYING A SUBJECT AS A CANDIDATE FOR TREATMENT WITH AN ANTIPLATELET AGENT

The present invention is directed to a method of identifying a subject as a candidate for treatment with an antiplatelet agent. The method may include the steps of (a) obtaining a biological sample from the subject; (b) determining the gene expression level of at least one biomarker of platelet function in the biological sample from the subject; (c) comparing the gene expression level of the at least one biomarker of platelet function in the biological sample to a reference level of the at least one biomarker of platelet function; (d) identifying the subject as a candidate for treatment with an antiplatelet agent if the gene expression level of the at least one biomarker of platelet function in the sample is higher than the reference level of the at least one biomarker of platelet function; and (e) administering an antiplatelet agent to the subject identified as a candidate for treatment with an antiplatelet agent.

The method may include the steps of (b) determining the gene expression level of RUNX1 in the biological sample from the subject; (c) comparing the level of RUNX1 in the biological sample to a reference level of RUNX1; and (d) identifying the subject as a candidate for treatment with an antiplatelet agent based on the level of RUNX1 in the sample. The subject is identified as a candidate for treatment with an antiplatelet agent if the gene expression level of RUNX1 is higher than the reference level of RUNX1 of platelet function.

The method may include determining the level of RUNX1 RNA transcript. The subject is identified as a candidate for treatment with an antiplatelet agent if: the RUNX1 RNA transcript is a P2-driven RUNX1 transcript and the level of RUNX1 RNA transcript is higher than the reference level; or the RUNX1 RNA transcript is a P1-driven RUNX1 transcript and the level of RUNX1 RNA transcript is lower than the reference level. The method includes administering an antiplatelet agent to the subject identified as a candidate for treatment with an antiplatelet agent.

6. METHODS FOR MONITORING ANTIPLATELET TREATMENT OF A SUBJECT

The present invention is directed to a method for monitoring the antiplatelet treatment of a subject. The subject may be suffering or will be suffering from cardiovascular disease or thrombosis.

The method may include the steps of (a) obtaining a biological sample from the subject, wherein the subject is under a current treatment regimen of an antiplatelet agent; (b) determining the gene expression level of at least one biomarker of platelet function in the biological sample; (c) comparing the gene expression level of the at least one biomarker of platelet function in the biological sample to a reference level of the at least one biomarker of platelet function; and (d) modifying the course of treatment based upon the gene expression level of the at least one biomarker of platelet function in the sample. If the gene expression level of the at least one biomarker of platelet function in the sample is the same or higher as the reference level of the at least one biomarker of platelet function, then a different antiplatelet agent or different dose/dosing frequency of the current antiplatelet agent is prescribed. If the gene expression level of the at least one biomarker of platelet function is lower than the reference level of the at least one biomarker of platelet function, then the current treatment regimen of the antiplatelet agent is continued or reduced.

The method may include the steps of (a) obtaining a biological sample from the subject, the subject is under a current treatment regimen of an antiplatelet agent; (b) determining the gene expression level of RUNX1 in the biological sample from the subject; (c) comparing the gene expression level of RUNX1 in the biological sample to a reference level of RUNX1; and (d) modifying the course of treatment based upon the gene expression level of RUNX1 in the sample. If the gene expression level RUNX1 in the sample is the same or higher as the reference level of RUNX1, then a different antiplatelet agent is prescribed. If the gene expression level RUNX1 is lower than the reference level of RUNX1, then the current treatment regimen of the antiplatelet agent is continued or reduced.

The method may include determining the level of an RUNX1 RNA transcript in the biological sample from the subject. If the RUNX1 RNA transcript is a P1-driven RUNX1 transcript and the level of RUNX1 RNA transcript is higher than the reference level or if the RUNX1 RNA transcript is a P2-driven RUNX1 transcript and the level of RUNX1 RNA transcript is lower than the reference level, then the current treatment with antiplatelet agent is continued or reduced. If the RUNX1 RNA transcript is a P1-driven RUNX1 transcript and the level of RUNX1 RNA transcript is lower than the reference level or if the RUNX1 RNA transcript is a P2-driven RUNX1 transcript and the level of RUNX1 RNA transcript is higher than the reference level, then a different antiplatelet agent or different dose/dosing frequency of the current antiplatelet agent is prescribed.

The method may include the steps of (a) obtaining a biological sample from the subject, wherein the subject is under a current treatment regimen of an antiplatelet agent, (b) performing at least one platelet function assay to generate a platelet function result for the sample, (c) determining a platelet function score (PFS) for the sample from the platelet function result of step (b) using principal components analysis; (d) comparing the PFS for the sample against a reference PFS; and (e) modifying the course of treatment based upon the PFS for the sample. If the PFS for the sample is the same or higher as a reference PFS, then a different antiplatelet agent or different dose/dosing frequency of the current antiplatelet agent is prescribed. If the PFS for the sample is lower than the reference PFS, then the current treatment regimen of the antiplatelet agent is continued or reduced.

The method may further include continuing to monitor the gene expression levels after the course of treatment is modified. Continued monitoring of gene expression levels may include repeating the steps described.

7. METHODS OF IDENTIFYING A SUBJECT SUFFERING FROM CARDIOVASCULAR DISEASE AS A CANDIDATE FOR TREATMENT WITH AN ANTIPLATELET AGENT

The present invention is directed to a method of identifying a subject suffering or will suffer from cardiovascular disease as a candidate for treatment with an antiplatelet agent. The method may include the steps of (a) obtaining a biological sample from the subject; (b) performing at least one platelet function assay to generate a platelet function result for the sample; (c) determining a platelet function score (PFS) for the sample from the platelet function result of step (b) using principal components analysis; (d) comparing the PFS for the sample against a reference PFS; (e) identifying the subject as a candidate for treatment with an antiplatelet agent if the PFS for the sample is greater than the reference PFS; and (f) administering an antiplatelet agent to the subject identified as a candidate for treatment with an antiplatelet agent.

8. BIOMARKERS OF PLATELET FUNCTION

The methods described above quantify the gene expression levels of a biomarker of platelet function or combinations of biomarkers of platelet function. The biomarker may be a gene that is responsive to antiplatelet therapy. The biomarker may increase or decrease gene expression level in response to the antiplatelet therapy. The biomarkers of platelet function include the genes of the ARS and RUNX1. One or all of these genes may be used as the biomarker of platelet function in the methods described above.

The biomarker of platelet function may be mRNA resulting from transcription of a gene or a protein resulting from translation of an mRNA. In some embodiments, the biomarker is a gene, or an mRNA resulting from transcription of a gene. In some embodiments, the biomarker comprises at least one gene of the ARS, which is also referred herein as Factor 14. In certain embodiments, the biomarker comprises ITGA2B. In other embodiments, the biomarker comprises RUNX1. As provided herein, a measurable increase or decrease of such a biomarker level, relative to a normal population, or alternatively, relative to levels of the same subject prior to anti-platelet treatment, provide an indication of the effectiveness of the anti-platelet treatment. In some embodiments, increased expression of one or more of such biomarkers indicates that treatment with an anti-platelet agent is not working effectively and additional administration with a second (or more) anti-platelet agent is needed. The use of at least one biomarker of platelet function, which includes the genes of ARS and RUNX1, may also be used to predict if subjects who are not on antiplatelet therapy are at risk or higher risk of death/MI.

(a) Aspirin Response Signature

The methods may include measuring the gene expression levels of a platelet response signature. RNA profiles of platelet-specific genes were discovered to be novel biomarkers for identifying subjects that do not respond adequately to aspirin and who are at risk for death/myocardial infarction. A set of 64 co-expressed genes named the "aspirin response signature" (ARS), which were identified by comparing the expression levels before and after aspirin was administered to subjects, was associated with PFS in healthy individuals. An association between the ARS and platelet function was observed after the administration of aspirin, suggesting that the latent effect of ARS genes on platelet function is unmasked in response to aspirin. When a CATHGEN cohort was stratified by aspirin use, it was observed that the association between the ARS and death/MI was higher in those using aspirin at the time of catheterization.

Corresponding proteins for 17 ARS genes were identified in the platelet proteome, of which, six were associated with PFS. The set of co-expressed genes are primarily of platelet origin. The ARS is associated with death/myocardial infarction in patient cohorts independent of cardiovascular risk factors. The ARS can be used to discriminate individuals at heighten risk for death/MI.

The set of co-expressed genes includes FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, TTC7B, ARHGAP6, PARVB, TUBB1, GNG11, PRSS1, PRKAR2B, MFAP3L, PBX1, ENDOD1, FRMD3, TMEM64, BEND2, RAB27B, ELOVL7, MMD, CLEC4D, SDPR, MYLK, CXCL5, C12ORF39, PCGF5, RHOBTB1, HIST1H3H, HIST1H2BG, PF4V1, LGALSL, CDC14B, HIST1H2AG, RHGAP18, RAB4A, TPM1, and C6ORF7.

The methods described above may include determining the gene expression levels of a subset of genes of the ARS or an individual gene of the ARS. The subset of genes may include at least 1 gene, at least 2 genes, at least 3 genes, at least 4 genes, at least 5 genes, at least 6 genes, at least 7 genes, at least 8 genes, at least 9 genes, at least 10 genes, at least 11 gene, at least 12 genes, at least 13 genes, at least 14 genes, at least 15 genes, at least 16 genes, at least 17 genes, at least 18 genes, at least 19 genes, at least 20 genes, at least 21 gene, at least 22 genes, at least 23 genes, at least 24 genes, at least 25 genes, at least 26 genes, at least 27 genes, at least 28 genes, at least 29 genes, at least 30 genes, at least 31 gene, at least 32 genes, at least 33 genes, at least 34 genes, at least 35 genes, at least 36 genes, at least 37 genes, at least 38 genes, at least 39 genes, at least 40 genes, at least 41 gene, at least 42 genes, at least 43 genes, at least 44 genes, at least 45 genes, at least 46 genes, at least 47 genes, at least 48 genes, at least 49 genes, at least 50 genes, at least 51 gene, at least 52 genes, at least 53 genes, at least 54 genes, at least 55 genes, at least 56 genes, at least 57 genes, at least 58 genes, at least 59 genes, at least 60 genes, at least 61 genes, at least 62 genes, at least 63 genes, or at least 64 genes of the genes of the ARS.

A particular subset of genes includes FSTL1, CTTN, CTDSPL, TREML1, SPARC, ITGA2B, CMTM5, SLC24A3, MPL, CLU, CPNE5, CLEC1B, SELP, IGF2BP3, SH3BGRL2, PROS1, ALOX12, JAM3, LRRC32, ITGB3, PPBP, MGLL, THBS1, MYL9, PF4, GP1BB, TGFB1I1, PCSK6, CALD1, GUCY1B3, PDE5A, and TTC7B. A particular subset of genes includes MYL9, ITGA2B, CMTM5, TREML1, ENDOD1, PBX1, LGALSL, TPM1, SLC24A3, TGFB1I1, IGF2BP3, SELP, CLEC4D, TTC7B, ITGB3, CLU, GP1BB, HIST1H2BG, THBS1, TMEM64, ALOX12, C12039, PARVB, SH3BGRL2, SPARC, PCSK6, PCGF5, PROS1, CALD1, CTDSPL, TRBV27, PF4, MGLL, FRMD3, HIST1H3H, TUBB1, PRKAR2B, ELOVL7, PPBP, CPNE5, FSTL1, LRRC32, CTTN, CLEC1B, RHOBTB1, GNG11, PDE5A, HIST1H2AG, ARHGAP18, and RAB4A. The individual gene may be ITGA2B, ITGB3, MYL9, CLU, PPKAR2B, TREML1, or CTTN.

(b) RUNX1

RUNX1 is a hematopoietic transcription factor that is involved in normal hematopoiesis and megakaryocyte differentiation. Deletion of RUNX1 leads to embryonic lethality in mice due to hemorrhage, and humans with mutations leading to RUNX1 haploin sufficiency are characterized by thrombocytopenia, impaired GPIIb/IIIa receptor-mediated aggregation, an "aspirin-like" platelet disorder, and a predisposition to leukemia. By contrast, gene duplication (as seen in Down's syndrome) leads to platelet hyperactivity. When platelets of an individual with a truncating RUNX1 mutation that eliminate its DNA binding domain were compared to those of normal donors, ~235 genes were found to be down-regulated, of which 28 overlapped with the ARS gene set. In addition, 29 of the 64 ARS genes were identified in ChIP-seq experiments using RUNX1 as the target. RUNX1 may be involved in the regulation of ARS transcripts and the response to aspirin, as RUNX1 transcripts correlate with ARS gene expression, platelet function in response to aspirin, and long-term clinical outcomes in patients with cardiovascular disease. Aspirin may reduce the risk of cardiovascular disease through modulation of the levels of the RUNX1 transcription factor. Changes in RUNX1 may likely occur at least at the level of the megakaryocyte.

RUNX1 is transcribed from two alternate promoters (P1 and P2) producing versions of RUNX1 that differ in their N-terminal sequences, but share the DNA binding domain and C-terminal transactivation domain. P1 and P2 derived RUNX1 transcripts have opposing relationships on gene expression, platelet function, clinical cardiovascular outcomes. The RUNX1 transcription factor is a cause of certain forms of leukemia due to inherited or acquired mutations, translocations, or duplications. Most genetic alterations disrupt its DNA binding domain or C-terminal transactivation domain. The N-terminal sequence of RUNX1 has an additional transactivation domain that is not required for normal megakaryocyte development. Further, the alternate N-terminal sequences appear to have different binding properties to RUNX1 target sequences.

An inverse correlation may exist between the P1 and P2 derived transcripts. When P1 and P2 derived transcripts were included in regression models for platelet function or clinical outcomes, the association of P1 derived transcripts was significant. Although P1 and P2 derived transcripts are associated with platelet function and clinical outcomes, the P1 derived transcripts with their influence on gene expression, platelet function, and cardiovascular outcomes may be more important.

9. PLATELET FUNCTION SCORE

The method may include determining a platelet function score (PFS) to assess the platelet function in response to antiplatelet therapy in a subject. The PFS may be determined by using a variety of platelet agonists before and after the administration of aspirin in conjunction with a principal components analysis (PCA) to derive an integrated measure of non COX-1 dependent platelet function (NCDPF) in a cohort of healthy volunteers.

The PFS may be calculated using the following equation:

$$PFS = 4(PFA100-199)/82*0.291) + ((AUCADP10-296.87)/40.58*-0.349) + ((AUCADP5-258.02)/56.75*-0.3398) + ((AUCADP1-47.0698)/49.863*-0.24477) + ((AUCEPI0\_5-120.0762)/137.58*-0.299) + ((AUCEPI1-185.465)/173.75*-0.3462) + ((AUCEPI10-343.576)/217.355*-0.387051) + ((AUCCOL5-256.41)/76.85*-0.3579) + ((AUCCOL2-193.84)/101.933*-0.3619))$$

where, PFA100=PFA100 collagen/epinephrine closure time (in seconds); AUCADP10, AUCADP5, and AUCADP1 are areas under the curve for ADP at 10, 5, and 1 µM, respectively; AUCEPI10, AUCEPI1, and AUCEPI0_5 are areas under the curve for Epinephrine at 10, 1, and 0.5 µM, respectively; and AUCCOL5 and AUCCOL2 are areas under the curve for Collagen at 5 and 2 mg/ml, respectively.

The PFS may be used to determine non COX-1 dependent platelet function and the platelet function response to aspirin.

(a) Platelet Function Assay

The methods described above may include performing at least one platelet function assay. Agonists such as collagen, epinephrine, and ADP can also stimulate platelet function through the generation of thromboxane. The platelet function assay may include measuring COX-1 dependent platelet function and non-COX-1 dependent platelet function. The platelet function assay may include light transmittance aggregometry (LTA) using the agonists, epinephrine, ADP, collagen, serum thromboxane B2 or arachidonic acid. The platelet function assay may also include point-of-care assays, such as PFA100.

10. ANTIPLATELET THERAPY

The methods of the invention described above measure the gene expression levels of at least one biomarker of platelet function in the subject and compare this level to a reference gene expression level of the at least one biomarker of platelet function. Depending on the method described above, this comparison is correlated to whether (1) a particular antiplatelet agent is appropriate for treating the subject, (2) an antiplatelet agent is even appropriate or effective for treating the subject, (3) platelet function changes or responds to the antiplatelet agent, (4) an antiplatelet agent will be effective in treating the cardiovascular disease or thrombosis, and (5) an antiplatelet agent will not be effective in treating the cardiovascular disease or thrombosis. An effective dosage of antiplatelet agent is administered to subjects identified as a candidate for antiplatelet therapy. The methods described above may be used to adjust the dosage or dosing frequency of antiplatelet agent to the subject. For example, by monitoring the platelet function response to aspirin, a subject may be administered twice daily dosing instead of daily dosing.

In some embodiments the antiplatelet agent can be administered to a patient in an amount of about 10 mg/day to about 500 mg/day, about 10 mg/day to about 200 mg/day (e.g., 10, 20, 30, 40, 50, 60, 70, 80, 90, 100, 110, 120, 130, 140, 150, 160, 170, 180, 190, or 200 mg/day), 100 mg/day to about 200 mg/day, or about 200 mg/day to about 500 mg/day (e.g., 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 mg/day), inclusive of any single or multi-dose daily administration regimen that falls within that total daily dose range. In some embodiments, the dose is from 150-325 mg/day. Additionally, one of ordinary skill in the art would also know how to adjust or modify variables such as dosage, dosage schedules, and routes of administration, as appropriate, for a given subject.

The subject identified or monitored in the methods described above may be currently treated with or may be identified as candidates for antiplatelet therapy or treatment. Platelet function inhibitors inhibit platelet aggregation, which are compounds that reduce or halt the ability of platelets to associate physically with themselves or with other cellular and non-cellular components, thereby precluding the ability of a platelet to initiate the formation of a thrombus. The antiplatelet agent may be an irreversible cyclooxygenase inhibitor, an adenosine diphosphate (ADP) receptor inhibitor, a phosphodiesterase inhibitor, a glycoprotein IIB/IIIA inhibitor, an adenosine reuptake inhibitor, a thromboxane inhibitor, a thromboxane synthase inhibitor, or a thromboxane receptor antagonist. For example, the antiplatelet agent may be aspirin, acadesine, prasugrel, ticagrelor, enilogrel, eptifibatide, cangrelor, anagrelide, anipamil, argatroban, clopidogrel, FR-122047, danaparoid sodium, dazoxiben hydrochloride, diadenosine 5',5'''-P1,P4-tetraphosphate (Ap4A) analogs, defibrotide, dilazep dihydrochloride, 1,2- and 1,3-glyceryl dinitrate, dipyridamole, dopamine and 3-methoxytyramine, efegatran sulfate, enoxaparin sodium, glucagon, Ro-43-8857, L-700,462, ifetroban, ifetroban sodium, iloprost, isocarbacyclin methyl ester, isosorbide-5-mononitrate, itazigrel, ketanserin, BM-13.177, lamifiban, lifarizine, molsidomine, nifedipine, oxagrelate, prostaglandin E (PGE), lexipafant, prostacyclin (PGI2), pyrazines, pyridinol carbamate, abciximab, sulfinpyrazone, BN-50727, BN-52021, CV-4151, E-5510, FK-409, GU-7, KB-2796, KBT-3022, KC-404, KF-4939, OP-41483-, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophylline, pentoxifylline, picotamide, sulotroban, tirofiban, trapidil, trifenagrel, trilinolein, dipyridamole, clofibrate, caffeine, ticlopidine and combinations thereof.

The antiplatelet agent(s) may be in the form of a pharmaceutical composition. The term "pharmaceutical composition" refers to the combination of compound (i.e., for example, anti-platelet agent) with a carrier, inert or active, making the composition especially suitable for diagnostic or therapeutic use in vivo, in vivo or ex vivo. A "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975)).

11. MEASURING GENE EXPRESSION LEVELS

The methods described above quantify the gene expression levels of a biomarker of platelet function or combinations of biomarkers of platelet function. The gene expression level of a particular biomarker of platelet function may be determined using any methods known in the art for assaying gene expression. The gene expression levels may be determined by measuring mRNA or protein levels of the genes encoding the biomarkers.

For example, an mRNA transcript of a gene may be detected for determining the expression level of the gene. Based on the sequence information provided by the GenBank™ database entries, the genes can be detected and expression levels measured using techniques well known to one of ordinary skill in the art. For example, sequences within the sequence database entries corresponding to polynucleotides of the genes can be used to construct probes for detecting mRNAs by, e.g., Northern blot hybridization analyses. The hybridization of the probe to a gene transcript in a subject biological sample can be also carried out on a DNA array, such as a microarray. The use of an array is preferable for detecting the expression level of a plurality of the genes. Examples of microarrays are those available from Affymetrix, such as Affymetrix U133A2 array and U133 plus 2.0 array.

As another example, the sequences can be used to construct primers for specifically amplifying the polynucleotides in, e.g., amplification-based detection methods such as reverse-transcription based polymerase chain reaction (RT-PCR). As another example, mRNA levels can be assayed by quantitative RT-PCR or RNA sequencing.

Furthermore, the expression level of the genes can be analyzed based on the biological activity or quantity of proteins encoded by the genes. The protein levels of a biomarker may be determined using proteomics or immunoassay. Any immunoassay may be utilized. For example, the immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, The ELISA may be a sandwich ELISA.

Specific immunological binding of the antibody to a biomarker of platelet function can be detected via direct labels, such as fluorescent or luminescent tags, metals and radionuclides attached to the antibody or via indirect labels, such as alkaline phosphatase or horseradish peroxidase.

The use of immobilized antibodies or fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and then processed quickly through washes and detection steps to generate a measurable signal, such as a colored spot.

12. REFERENCE LEVELS

The methods described above compare the gene expression levels of at least one biomarker of platelet function to a reference level of the at least one biomarker of platelet function. The reference level may be a cutoff value of the at least one biomarker of platelet function determined by receiver operating characteristic (ROC) analysis from biological samples of a patient group with and without cardiovascular disease or with and without conditions associated with cardiovascular disease. The reference level may be a cutoff value that is a change in gene expression pre-vs. post-aspirin in a control subject, such as a healthy subject or patient without cardiovascular disease, as determined by RT-PCR.

(a) Aspirin Response Signature

A cutoff values may be the change in gene expression pre-vs. post-aspirin in healthy volunteers as determined by RT-PCR. For example, a cutoff value may be at least a 0.5 absolute change, 0.6 absolute change, 0.7 absolute change, 0.8 absolute change, 0.9 absolute change, 1.0 absolute change, 1.1 absolute change, 1.2 absolute change, 1.3 absolute change, 1.4 absolute change, 1.5 absolute change, 1.6 absolute change, 1.7 absolute change, 1.8 absolute change, 1.9 absolute change, 2.0 absolute change, 2.1 absolute change, 2.2 absolute change, 2.3 absolute change, 2.4 absolute change, 2.5 absolute change, 3.0 absolute change, 3.5 absolute change, 4.0 absolute change, 4.5 absolute change, or 5.0 absolute change in gene expression of the ARS.

A cutoff value may be at least a 0.5 absolute change, 0.6 absolute change, 0.7 absolute change, 0.8 absolute change, 0.9 absolute change, 1.0 absolute change, 1.1 absolute change, 1.2 absolute change, 1.3 absolute change, 1.4 absolute change, 1.5 absolute change, 1.6 absolute change, 1.7 absolute change, 1.8 absolute change, 1.9 absolute change, 2.0 absolute change, 2.1 absolute change, 2.2 absolute change, 2.3 absolute change, 2.4 absolute change, 2.5 absolute change, 3.0 absolute change, 3.5 absolute change, 4.0 absolute change, 4.5 absolute change, or 5.0 absolute change of a reduction in gene expression of the ARS.

A cutoff value may be at least a 0.5 absolute change, 0.6 absolute change, 0.7 absolute change, 0.8 absolute change, 0.9 absolute change, 1.0 absolute change, 1.1 absolute change, 1.2 absolute change, 1.3 absolute change, 1.4 absolute change, 1.5 absolute change, 1.6 absolute change, 1.7 absolute change, 1.8 absolute change, 1.9 absolute change, 2.0 absolute change, 2.1 absolute change, 2.2 absolute change, 2.3 absolute change, 2.4 absolute change, 2.5 absolute change, 3.0 absolute change, 3.5 absolute change, 4.0 absolute change, 4.5 absolute change, or 5.0 absolute change of an increase in gene expression of the ARS.

A cutoff values may be the change in gene expression pre-vs. post-aspirin in healthy volunteers as determined by RT-PCR. For example, cutoff value may be at most a 0.5 absolute change, 0.6 absolute change, 0.7 absolute change, 0.8 absolute change, 0.9 absolute change, 1.0 absolute change, 1.1 absolute change, 1.2 absolute change, 1.3 absolute change, 1.4 absolute change, 1.5 absolute change, 1.6 absolute change, 1.7 absolute change, 1.8 absolute change, 1.9 absolute change, 2.0 absolute change, 2.1 absolute change, 2.2 absolute change, 2.3 absolute change, 2.4 absolute change, 2.5 absolute change, 3.0 absolute change, 3.5 absolute change, 4.0 absolute change, 4.5 absolute change, or 5.0 absolute change in gene expression of the ARS.

A cutoff value may be at most a 0.5 absolute change, 0.6 absolute change, 0.7 absolute change, 0.8 absolute change, 0.9 absolute change, 1.0 absolute change, 1.1 absolute change, 1.2 absolute change, 1.3 absolute change, 1.4 absolute change, 1.5 absolute change, 1.6 absolute change, 1.7 absolute change, 1.8 absolute change, 1.9 absolute change, 2.0 absolute change, 2.1 absolute change, 2.2 absolute change, 2.3 absolute change, 2.4 absolute change, 2.5 absolute change, 3.0 absolute change, 3.5 absolute change, 4.0 absolute change, 4.5 absolute change, or 5.0 absolute change of a reduction in gene expression of the ARS.

For example, cutoff value may be at most a 0.5 absolute change, 0.6 absolute change, 0.7 absolute change, 0.8 absolute change, 0.9 absolute change, 1.0 absolute change, 1.1 absolute change, 1.2 absolute change, 1.3 absolute change, 1.4 absolute change, 1.5 absolute change, 1.6 absolute change, 1.7 absolute change, 1.8 absolute change, 1.9 absolute change, 2.0 absolute change, 2.1 absolute change, 2.2 absolute change, 2.3 absolute change, 2.4 absolute change, 2.5 absolute change, 3.0 absolute change, 3.5 absolute change, 4.0 absolute change, 4.5 absolute change, or 5.0 absolute change of an increase in gene expression of the ARS.

(b) Individual Gene Transcripts

A cutoff values may be the change in gene expression pre-vs. post-aspirin in healthy volunteers as determined by RT-PCR. For example, a cutoff value may be at least a 0.5-fold, 0.6-fold, 0.7-fold, 0.8-fold, 0.9-fold, 1.0-fold, 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 3.0-fold, 3.5-fold, 4.0-fold, 4.5-fold, or 5.0-fold in gene expression of at least one biomarker of platelet function.

A cutoff value may be at least a 0.5-fold, 0.6-fold, 0.7-fold, 0.8-fold, 0.9-fold, 1.0-fold, 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 3.0-fold, 3.5-fold, 4.0-fold, 4.5-fold, or 5.0-fold of a reduction in gene expression of at least one biomarker of platelet function.

A cutoff value may be at least a 0.5-fold, 0.6-fold, 0.7-fold, 0.8-fold, 0.9-fold, 1.0-fold, 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 3.0-fold, 3.5-fold, 4.0-fold, 4.5-fold, or 5.0-fold of an increase in gene expression of at least one biomarker of platelet function.

13. COMBINATION WITH CLINICAL AND LABORATORY DATA

The methods described above quantify the gene expression levels of a biomarker of platelet function or combinations of biomarkers of platelet function. The gene expression levels may be used in combination with other clinical and laboratory data to assess platelet function in response to aspirin or predicting cardiovascular events. Examples of clinical and laboratory data include Age, Sex, Race, Smoking, Diabetes, Hypertension, Hyperlipidemia, Coronary artery, disease, Platelet count, and Mean platelet volume.

14. SUBJECTS OR SUBJECT IN THE METHOD

The methods described above are directed to treating a subject with an antiplatelet agent. The subject treated, diagnosed, or monitored by the methods described above may be a subject or patient suffering from a condition associated with cardiovascular disease, thrombosis, or excessive bleeding. The subject may be treated with an antiplatelet agent before or after the methods described above are performed. Some of the methods described above determine whether an antiplatelet agent is appropriate to administer to the subject suffering from a condition associated with cardiovascular disease, thrombosis, or excessive bleeding.

(c) Cardiovascular Disease

Cardiovascular disease may refer to ischemia; arterial damage (damage to the endothelial lining) due to physical damage (endartiectomy, balloon angioplasty) or as a result of chronic damage (including atherosclerosis); myocardial damage (myocardial necrosis); any physiological or pathophysiological condition that elicits a neoangiogenic response; and myonecrosis. Cardiovascular disease may include ischemic heart disease, which is related to problems with the circulation of the blood to the heart muscle, cerebrovascular disease, which is related to problems with the circulation of the blood in the blood vessels of the brain, and peripheral vascular disease, which affects the circulation primarily in the legs. Subjects with cardiovascular disease may develop a number of complications, including, but not limited to, fatal or non-fatal myocardial infarction, stroke, angina pectoris, transient ischemic attacks, peripheral arteriopathy, aneurysms, arrhythmia, atherosclerosis, cardiomyopathic, cerebrovascular accident (stroke), cerebrovascular disease, congenital heart disease, congestive heart failure, coronary heart disease (CHD), also referred to as coronary artery disease (CAD), ischemic heart disease or atherosclerotic heart disease, cardiovascular death, sudden cardiac death, dilated cardiomyopathy, diastolic dysfunction, endocarditis, heart failure, hypertension (high blood pressure), hypertrophic cardiomyopathy, mitral valve prolapse, myocarditis, rheumatic heart disease, and valve disease.

(d) Thrombosis

Thrombosis may refers to the formation or presence of coagulated blood and/or platelets attached at the site of formation, or that have detached from the site of origin and embolized to another part of the circulatory system, and includes, without limitation, acute coronary artery thrombosis which can lead to myocardial infarction, acute cerebral artery thrombosis, which can lead to stroke and ischemic attacks, thrombosis in vascular catheters, thrombosis of vascular grafts, venous thromboembolism thrombosis associated with organ transplantation, venous thromboembolism, venous thrombosis, renal vein thrombosis, clot formation in bypass, hemodialysis or continuous renal replacement therapy (CRRT) circuits, and thrombosis in dialysis vascular fistulas and grafts.

(e) Excessive Bleeding

The subject treated, diagnosed, or monitored by the methods described above may be a subject or patient suffering from a condition associated with an increased risk of excessive bleeding. A subject at risk of excessive bleeding may have an abnormality or disease of the platelets called a thrombocytopathy, which could be a low number of platelets (thrombocytopenia), a decrease in function of platelets (thrombasthenia), or an increase in the number of platelets (thrombocytosis). A disorder that reduces the number of platelets may cause a subject to be at risk of excessive bleeding, such as heparin-induced thrombocytopenia (HIT) or thrombotic thrombocytopenic purpura (TTP) that typically cause thromboses, or clots, instead of bleeding.

15. KITS

Provided herein is a kit, which may be used for performing the methods described above. The kit may provide at least one reagent capable of binding a biomarker of platelet function described above and a reference standard indicating a reference gene expression level of the biomarker of platelet function. The kit may further comprise additional reagents capable of binding one or more of the other biomarkers of platelet function described above and a reference standard indicating a reference gene expression level of the additional biomarker of platelet function. The kit may also comprise one or more containers, such as vials or bottles, with each container containing a separate reagent. The kit may further comprise written instructions, which may describe how to perform or interpret an analysis, monitoring, treatment, or method described herein.

16. EXAMPLES

The foregoing may be better understood by reference to the following examples, which are presented for purposes of illustration and are not intended to limit the scope of the invention. The present invention has multiple aspects, illustrated by the following non-limiting examples.

Example 1

Aspirin Challenge Study

Overview.

A summary and single metric of platelet function that integrates multiple non-COX1 dependent platelet function (NCDPF) test results was developed by employing a principal components analysis to NCDPF data from an aspirin challenge study in healthy volunteers. This metric, termed platelet function score (PFS), was derived and validated in independent cohorts of healthy volunteers and diabetics, which are a group characterized by heightened platelet function. The utility of the PFS was demonstrated by 1) comparing COX-1 vs. non-COX-1 dependent measures of platelet function and 2) investigating the reproducibility and time-dependent effects of NCDPF during daily aspirin therapy.

Several aspirin challenge studies were performed to examine gene expression profiles in healthy volunteers and diabetics at the extremes of platelet function in response to aspirin. The study design and sample sizes were chosen for the purposes of analyzing gene expression data, not platelet function in response to aspirin per se. A summary of the platelet function observations was made and an overview of the different cohorts and time points are described in FIG. 1. After a pilot study of healthy volunteers ("HV1") was completed, the study protocol was amended for two subsequent studies in healthy volunteers and diabetics ("HV2" and "DM", respectively): increased duration of aspirin exposure, increased age requirement, addition of arachidonic acid aggregation with and without in vitro aspirin, and a focus on those at the extremes of platelet function response. The HV2 and DM cohorts served as independent validation cohorts for the observations made in HV1.

A group of healthy adult volunteers (HV1) were recruited and a defined set of platelet function measurements, as described below, were made before aspirin ("Pre") and 3-hrs after ("Post") a single 325 mg tablet of aspirin. Subsequently, subjects were returned for a final assessment ("Final") 2 weeks after 325 mg/day aspirin. This dose of aspirin was chosen to ensure complete suppression of platelet COX-1 activity in each participant. The 3-hour timepoint was chosen to measure the maximal inhibitory effect of aspirin.

Inclusion and Exclusion Criteria.

This study included healthy volunteers greater than 18 (HV1) or 30 (HV2) years old and diabetics (defined by chart review and/or use of insulin or oral agent) greater than 30 years of age. The following exclusion criteria applied to all cohorts: history of a bleeding disorder, gastrointestinal bleeding, regular use of antiplatelet agents (except aspirin in DM), nonsteroidal anti-inflammatory agents (NSAIDs), oral corticosteroids, anticoagulants, coexisting conditions: diabetes (except for HV1 and HV2), coronary artery disease, peripheral artery disease, cerebrovascular disease, history of stroke, deep venous thrombosis, transient ischemic attack, daily use of more than 1 prescription medication (for HV1 and HV2, except oral contraceptives and anti-histamines), regular cigarette use (defined as >1 cigarette/day), or known pregnancy.

Throughout the study period subjects were reminded to refrain from any new medications (in particular those containing aspirin or NSAIDs) and cigarette use. Subjects were given a list of over the counter medications that contain aspirin/NSAIDs to avoid. Dietary supplements were not exclusion criteria and were not recorded, but instead, subjects were instructed to not alter their intake of any supplements throughout the study period.

Aspirin and NSAID Washout.

For subjects taking aspirin or NSAIDs prior to entry into the study, the subject was asked to reschedule their visit after at least 14 days of documented aspirin/NSAID abstinence.

Aspirin Therapy.

Medication adherence was a priority and subjects were required to record the date and time of each aspirin dose. Adherence was confirmed with a pill count at the end of the study. Finally, subjects received telephone reminders during the study to ensure adherence. Subjects that missed any of the three doses prior to the Final visit were given additional aspirin and rescheduled until adherence was established.

Platelet Function Studies.

Before each visit, subjects were asked to fast and to refrain from tobacco (during the preceding 24 hrs) and alcohol or intensive exercise on the day of testing. Phlebotomy was performed after 10 minutes of resting supine with minimal trauma or stasis at the venipuncture site using a 21-guage needle into 3.2% sodium citrate tubes. The focus of these studies was around NCDPF and thus, the NCDPF assays were defined as the following: PFA100, and epinephrine, ADP, and collagen induced LTA. COX-1 dependent platelet function was initially not measured in HV1, however after observing the changes in NCDPF in HV1, COX-1 dependent measures was added to HV2. Serum thromboxane B2 and AA induced aggregation were chosen as measures of COX-1 activity and also added in vitro aspirin to the AA aggregation assay to further assess for any evidence of unsuppressed COX-1 activity.

Light Transmittance Aggregometry.

Light transmittance aggregometry (LTA) was performed as previously described (Born (1964) Nature 202:95-96) using the following agonists: arachidonic acid (AA, Chrono-log, 0.5 mM), epinephrine (Chrono-Log, 10, 1, and 0.5 µM), ADP (Chrono-Log, 10, 5, and 1 µM), and collagen (Chrono-Log, 5 and 2 µg/ml). The area under the LTA curve (AUC) was chosen as the primary measure of aggregation because the AUC captures several features of the aggregometry curve that are each sensitive to the effects of aspirin: slope, maximal aggregation, and final aggregation. To standardize AUC measurements across individuals and visits the test duration was fixed at 12 minutes for epinephrine and six minutes for collagen, AA, and ADP.

Description of Area Under the Curve (AUC) Measurement.

Figure 21:
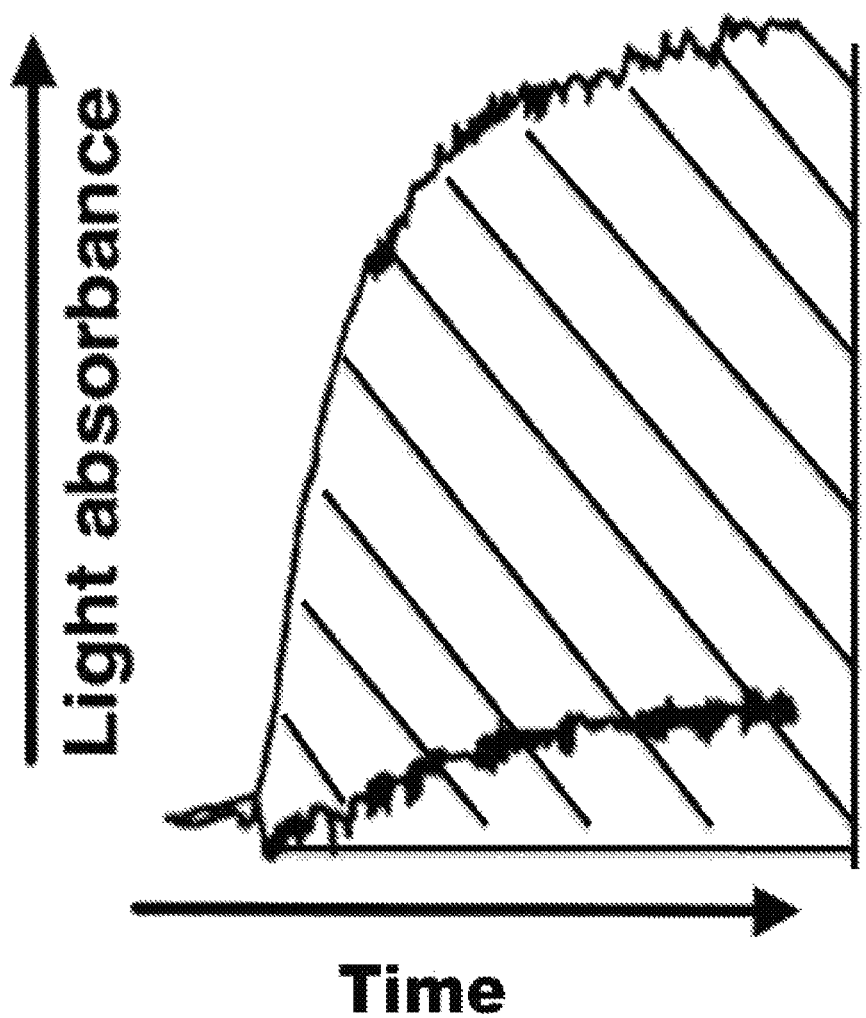
FIG. 21 shows an example plot of percent aggregation over time.

Using light transmittance aggregometry the percent aggregation is plotted over time to produce the upper curve similar to FIG. 21. The AUC is measured by the aggregometer over the duration of the test, which is fixed at 6 minutes for collagen and ADP and 12 minutes for epinephrine. Higher AUC values reflect higher maximal and residual aggregation, slope, and velocities.

Platelet Function Analyzer.

PFA100 closure time with the use of the collagen/epinephrine cartridge was performed. The collagen/ADP cartridge was not selected because its results are not sensitive to the effects of aspirin. Briefly, citrated whole blood was placed in the PFA100 chamber and blood was aspirated through an aperture in a collagen/epinephrine coated membrane. The amount of time (in seconds[s], up to a maximum of 300 s) until blood ceased to flow through the membrane aperture was recorded as the final result.

Serum Thromboxane B2.

Serum thromboxane B2 was measured in HV2 at the Final visit. Briefly, serum was collected by allowing whole blood to clot at 37° C. for 45 minutes then centrifuged at 3000 rpm for 10 minutes. Serum was aspirated and stored at −80 degrees Celsius until ELISA testing. Thromboxane B2 measurements were performed using an ELISA based assay, in duplicate, averaged, and according to the manufacture's protocol (Enzo Life Sciences, Catalog No. ADI-900-002) with no modifications.

In Vitro Aspirin.

A stock solution of aspirin was created by dissolving acetylsalicylic acid (Sigma-Aldrich A5376) into DMSO and aliquots stored at −80 degrees Celsius. On the day of use, fresh aliquots were thawed, diluted in PBS, and stored at 4 degrees Celsius. This diluted aspirin solution was added to PRP to a final concentration of aspirin (53 μM) that exceeds that achieved in vivo with a 325 mg aspirin dose or required to maximally inhibit arachidonic induced aggregation. The PRP was allowed to incubate with in vitro aspirin for 10 minutes at room temperature prior to the addition of agonist.

Statistical Analysis.

Correlations between the various measures of platelet function were assessed with the Spearman correlation coefficient (r). Paired or unpaired t-tests were employed to compare continuous variables between groups and the Wilcoxon signed rank test was used for variables that were not normally distributed. Chi square tests were used to compare categorical variables between groups.

Missing Data.

A small number of time-points (n=21.5%) in the collagen LTA data were missing and were imputed in the following manner: 1) Replace the missing values by the average for that assay. 2) Compute principal components. Let x be the NxP-dimensional matrix of platelet function measurements, where N is the number of samples and P is the number of different platelet function measurements. Compute the singular value decomposition: x=UDV'. The D* was then computed by setting to zero all but the first three diagonal elements of D. 3) Compute x*=UD*V' and replace all missing values of x with the corresponding values from x*. 4) Repeat steps 2 and 3 until the algorithm converges.

Platelet Function Score.

The main interest was to study NCDPF since minimal variation in COX-1 dependent platelet function measures on aspirin was previously shown. Because linear relationships between the multiple measures of NCDPF were observed (Table 2), it was assumed that each measure of NCDPF was a reflection of a single biological factor. A platelet function score was derived from a principal components analysis (PCA) of all platelet function measurements made in the HV1 cohort. PCA was chosen to quantify this biological factor. PCA is an unbiased, mathematical technique for reducing a collection of measurements down to a single "meta-measurement" that best describes the aggregate behavior of the set. For example, in the biological sciences, PCA can quantify population substructure in genome wide association studies, patterns of gene expression in microarray experiments, and metabolic pathways in metabolomic studies. In the present study, the input into the PCA was the following set of non-imputed measures from the HV1 cohort: the PFA100 closure time and the AUC from each concentration of ADP, epinephrine, and collagen LTA. Each measurement was given equal weight and the first principal component was defined, which was constructed to be positively correlated with higher NCDPF, as the platelet function score (PFS).

To calculate PFS in a new sample the weights from the PCA performed in HV1 and the new platelet function measurements (i.e., in HV2, DM, and imputed HV1 data) was applied as follows:

$$PFS = -4(PFA100-199)/82*0.291)+((AUCADP10-296.87)/40.58*-0.349)+((AUCADP5-258.02)/56.75*-0.3398)+((AUCADP1-47.0698)/49.863*-0.24477)+((AUCEPI0\_5-120.0762)/137.58*-0.299)+((AUCEPI1-185.465)/173.75*-0.3462)+((AUCEPI10-343.576)/217.355*-0.387051)+((AUCCOL5-256.41)/76.85*-0.3579)+((AUCCOL2-193.84)/101.933*-0.3619))$$

where PFA100=PFA100 collagen/epinephrine closure time (in seconds); AUCADP10, AUCADP5, and AUCADP1=areas under the curve for ADP at 10, 5, and 1 μM, respectively; AUCEPI10, AUCEPI1, and AUCEPI0_5=areas under the curve for Epinephrine at 10, 1, and 0.5 μM, respectively; AUCCOL5 and AUCCOL2=areas under the curve for Collage at 5 and 2 mg/ml, respectively.

All analyses were performed in R (version 2.8.1). All statistical tests were two-sided and a p-value<0.05 was considered significant.

Results.

The baseline characteristics of the three cohorts are described in Table 1. Besides differences in medications, age was the only significantly different baseline characteristic between cohorts. As outlined in FIG. 1, pre-aspirin (Pre) and the 3 hour post-aspirin (Post) measurements were made in 52 subjects in HV1, 96 subjects in HV2, and 74 subjects in DM. Per our selection protocols, the following numbers of subjects returned for the Final visit in each cohort: 52 in HV1, 52 in HV2, and 42 in DM.

TABLE 1

Baseline Characteristics

|  | HV1 (n = 52) | HV2 (n = 96) | DM (n = 74) |
|---|---|---|---|
| Age (mean +/−SD, years) | 31 ± 9 | 43 ± 9* | 55 ± 11* |
| Female (n) | 26 | 59 | 46 |
| Race (n, white/black/other) | 36/9/7 | 60/32/4 | 40/30/4 |
| Medications (n) | | | |
| OCP | 5 | 6 | 0 |
| Insulin | — | — | 9 |
| Oral agents | — | — | 59 |
| Diet control | — | — | 6 |
| Anti-HTN | — | — | 49 |
| Lipid lowering | — | — | 37 |

*$p < 0.001$ for comparison with HV1; OCP = oral contraceptive pills; HTN = hypertensive The study was expanded to diabetics so in order to have a group of healthy volunteers whose age was similar to those of diabetics, the age restriction was increased to 30 years. This second group of healthy volunteers (HV2) and diabetics (DM) were recruited and assessed with an identical set platelet function measures made as in HV1 before (Pre) and 3-hrs after (Post) a 325 mg aspirin dose. Using their platelet function data, the PFS was calculated for each subject. The first 10 subjects in HV2 and DM were used to define the PFS distribution for each cohort, selected to continue with 4 weeks of aspirin therapy, and returned for a final measurement of platelet function (Final). For subsequent subjects in the HV2 and DM cohorts, the $1^{st}$ and $4^{th}$ quartile of their respective PFS distribution were selected for additional aspirin therapy and final platelet function testing (Final).

Construction of the Platelet Function Score (PFS) as a Surrogate for Non COX1 Dependent Platelet Function (NCDPF).

A strong and significant correlation between various measures of NCDPF made before and after aspirin exposure in HV1 was observed (Table 2).

TABLE 2

Significant correlations between measures of non-COX dependent platelet function in HV1

|         | PFA   | ADP 10 µM | ADP 5 µm | ADP 1 µM | Epi 10 µM | Epi 1 µM | Epi .5 µM | Col 5 µg/l | Col 2 µg/µl |
|---------|-------|-----------|----------|----------|-----------|----------|-----------|------------|-------------|
| PFA     |       | −0.25     | −0.29    | −0.27    | −0.50     | −0.50    | −0.51     | −0.23      | −0.29       |
| ADP 10 µM | −0.25 |         | 0.87     | 0.61     | 0.65      | 0.58     | 0.58      | 0.79       | 0.74        |
| ADP 5 µM  |       | 0.83      |          | 0.65     | 0.65      | 0.58     | 0.62      | 0.77       | 0.67        |
| ADP 1 µM  |       | 0.42      | 0.54     |          | 0.66      | 0.66     | 0.70      | 0.53       | 0.58        |
| Epi 10 µM | −0.28 | 0.66      | 0.66     | 0.49     |           | 0.91     | 0.92      | 0.60       | 0.66        |
| Epi 1 µM  | −0.26 | 0.47      | 0.52     | 0.61     | 0.79      |          | 0.94      | 0.53       | 0.65        |
| Epi 0.5 µM | −0.22 | 0.41     | 0.42     | 0.58     | 0.62      | 0.83     |           | 0.57       | 0.68        |
| Col 5 µg  | −0.44 | 0.56      | 0.41     | —        | 0.45      | 0.33     | 0.26      |            | 0.87        |
| Col 2 µg  | −0.55 | 0.55      | 0.49     | —        | 0.44      | 0.32     | —         | 0.75       |             |

Significant (p < 0.05) Pearson correlation coefficients are reported before (below diagonal), after (above diagonal) aspirin.
PFA = PFA100 closure time in seconds;
Remaining measurements used area under the light transmittance aggregometry curve;
Epi = epinephrine;

Col = Collagen

To condense these measures of platelet function into a single metric, a PCA on the PFA100 closure time and the AUCs induced by epinephrine, ADP, and collagen was conducted to derive the PFS on all timepoints in HV1. The PFS was highly correlated with the platelet function measurements used to construct the PFS, with the weakest correlation with PFA100 and strongest with epinephrine LTA. (Table 3) To validate the PFS, the correlation between PFS and platelet function measures in HV2 and DM cohorts was assessed. In these cohorts, the PFS was calculated by taking their platelet function measures and applying the weights derived from the PCA from HV1. In these validation cohorts, the PFS significantly and strongly correlated with each measure of NCDPF, with a similar strength and direction as in HV1 (Table 3).

TABLE 3

Significant correlations between measures of non-COX dependent platelet function and PFS in derivation (HV1) and validation (HV2 and DM) cohorts

| Cohort | PFA | ADP 10 µM | ADP 5 µM | ADP 1 µM | Epi 10 µM | Epi 1 µM | Epi .5 µM | Col 5 µg/µl | Col 2 µg/µl |
|--------|-----|-----------|----------|----------|-----------|----------|-----------|-------------|-------------|
| Correlation with Pre PFS ||||||||||
| HV1    |         | 0.72** | 0.79** | 0.69** | 0.88** | 0.87** | 0.78** | 0.55** | 0.68** |
| HV2    |         | 0.83** | 0.82** | 0.62** | 0.80** | 0.85** | 0.79** | 0.57** | 0.74** |
| DM     | −0.21** | 0.87** | 0.84** | 0.81** | 0.82** | 0.80** | 0.77** | 0.69** | 0.84** |
| Correlation with Post PFS ||||||||||
| HV1    | −0.48** | 0.89** | 0.89** | 0.81** | 0.89** | 0.89** | 0.85** | 0.89** | 0.88** |
| HV2    | −0.34*  | 0.85** | 0.89** | 0.75** | 0.77** | 0.73** | 0.74** | 0.80** | 0.75** |
| DM     | −0.27*  | 0.87** | 0.87** | 0.83** | 0.75** | 0.71** | 0.76** | 0.85** | 0.80** |
| Correlation with Final PFS ||||||||||
| HV1    | −0.55** | 0.85** | 0.85** | 0.72** | 0.83** | 0.79** | 0.84** | 0.87** | 0.91** |
| HV2    | −0.52** | 0.81** | 0.89** | 0.62** | 0.80** | 0.80** | 0.81** | 0.85** | 0.84** |
| DM     | −0.45*  | 0.87** | 0.88** | 0.76** | 0.82** | 0.76** | 0.77** | 0.85** | 0.78** |

The platelet function score (PFS) was derived in the HV1 cohort and validated in the HV2 and DM cohorts (as described in Methods). Significant correlations between PFS and each measure of platelet function;
PFA = PFA100 closure time in seconds;
Remaining measurements used area under the light transmittance aggregometry curve;
Epi = epinephrine;
Col = Collagen;
*p = 0.01 > p > 0.001;
**p < 0.0001

Acute Effects of Aspirin on COX-1 Dependent Platelet Function.

Figure 2:
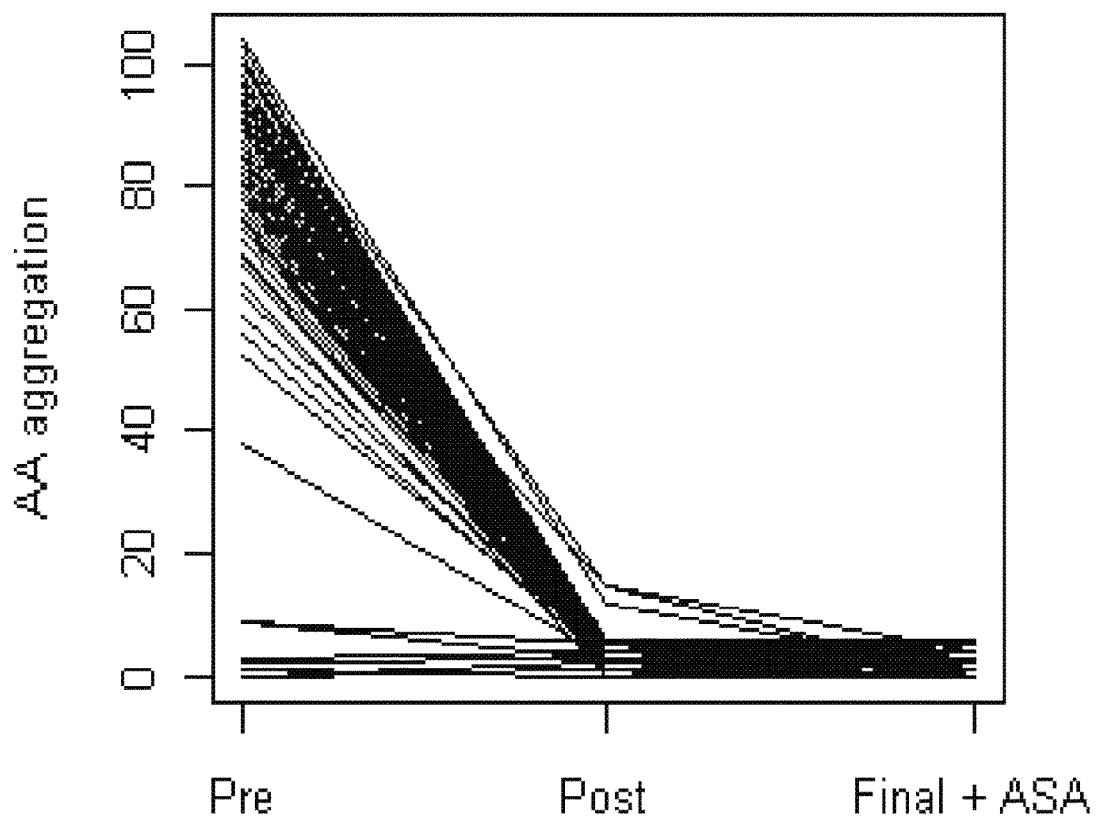
FIG. 2 shows COX-1 dependent platelet function with aspirin. Arachidonic acid-induced platelet aggregation before (Pre), 3 hrs after 325 mg aspirin by mouth without in vitro aspirin (Post), and 3 hrs after 325 mg aspirin by mouth with in vitro aspirin. (Post+ASA) % aggregation on Y axis; AA arachidonic acid concentration=0.5 mM; in vitro aspirin concentration=53 µM.
Figure 2:
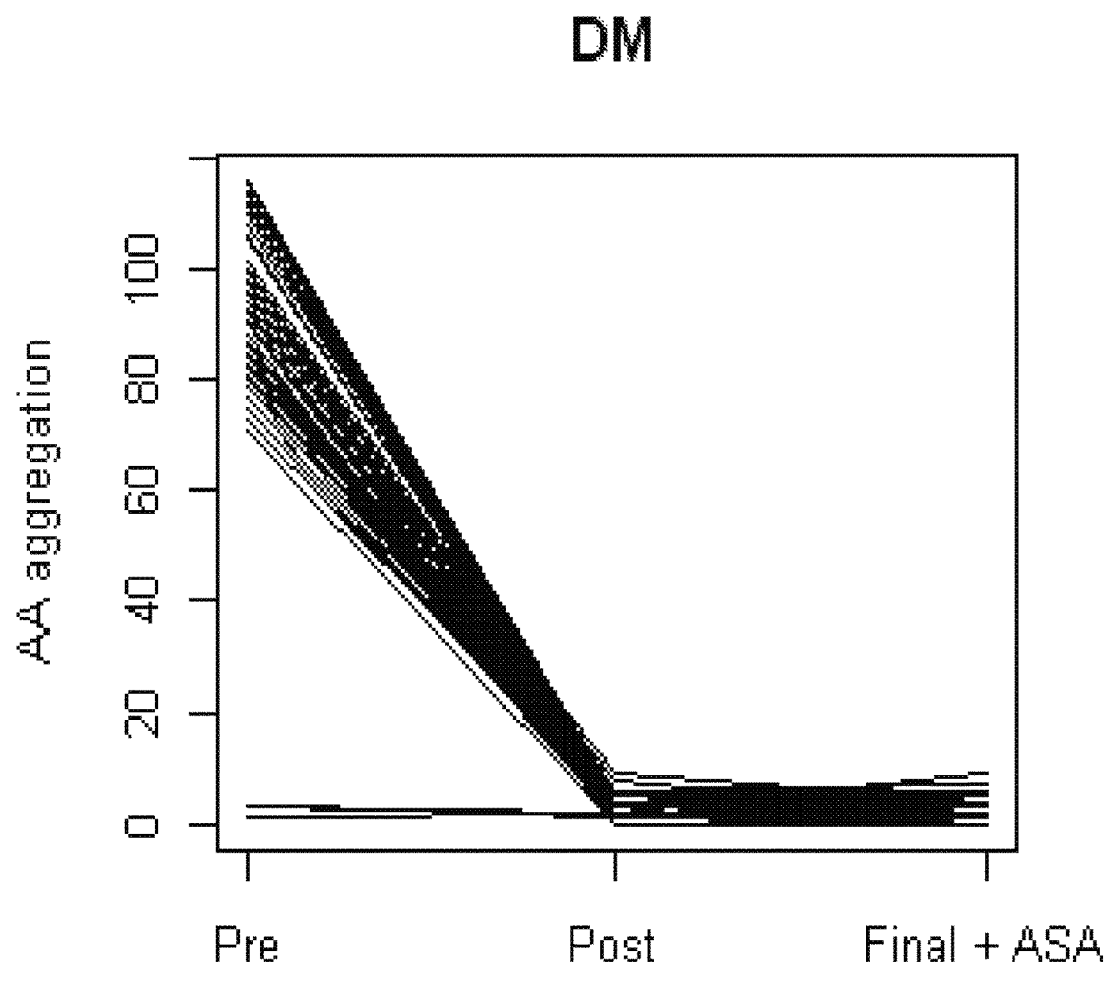

COX-1 dependent platelet function, as assessed by AAA, was effectively suppressed by a single, 325 mg dose of aspirin in all HV2 and DM subjects; the in vitro addition of aspirin had no further effect on AAA. (FIG. 2).

Acute Effects and Characteristics of Aspirin on NCDPF.

Figure 3:
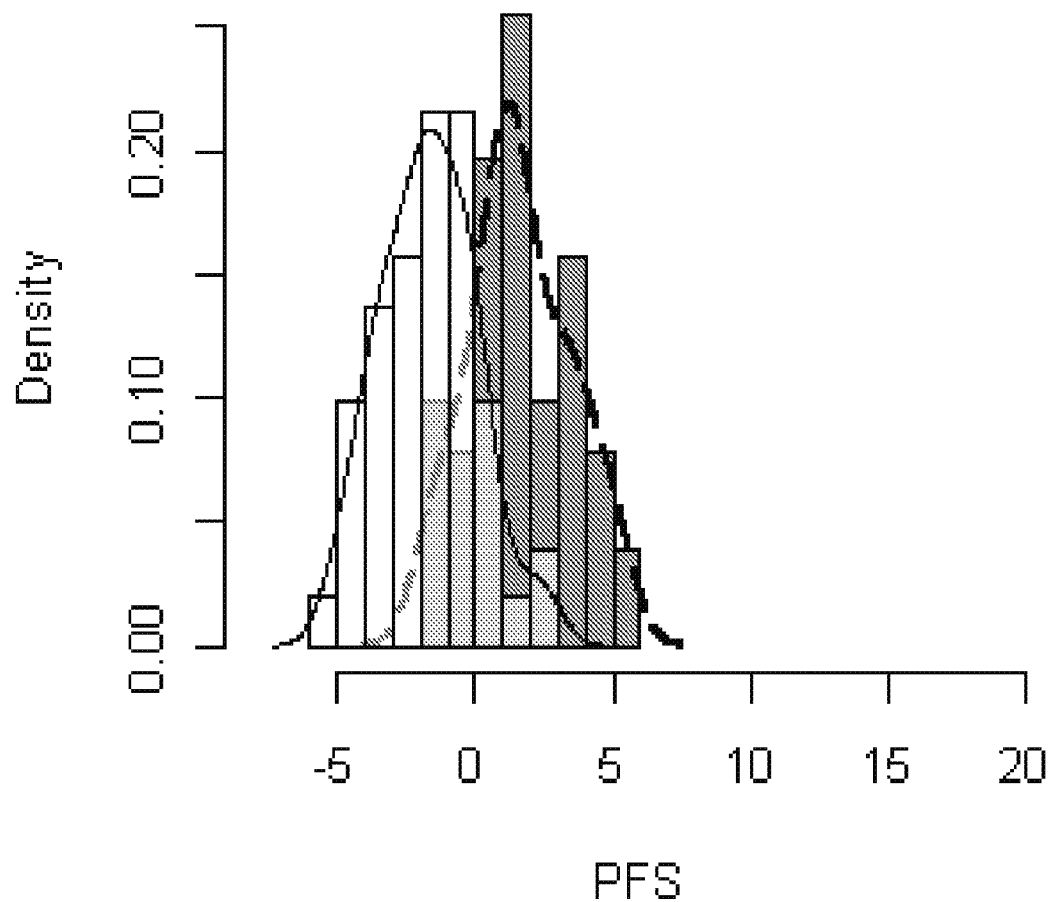
FIG. 3 shows the distributions of Platelet Function Score (PFS). Histograms of platelet function score (PFS) for two cohorts of healthy volunteers (HV1 and HV2) and a cohort of diabetics (DM), before (Pre, shaded) and 3 hrs after a single 325 mg aspirin dose (Post, unshaded). The curves represent the probability density functions for the Pre (dashed) and Post (solid) PFS distributions, demonstrate the shift towards lower platelet function with a single dose of aspirin, and that variable pre-aspirin platelet function is largely retained post-aspirin.
Figure 3:
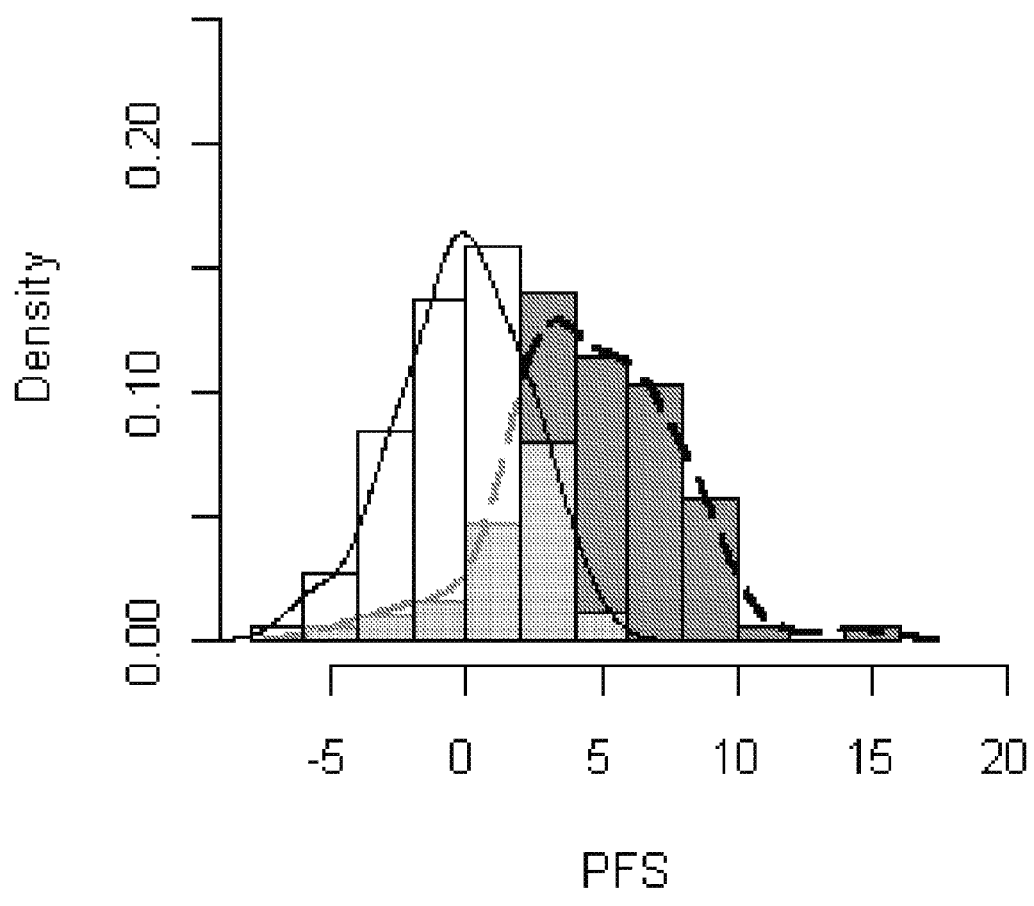
Figure 3:
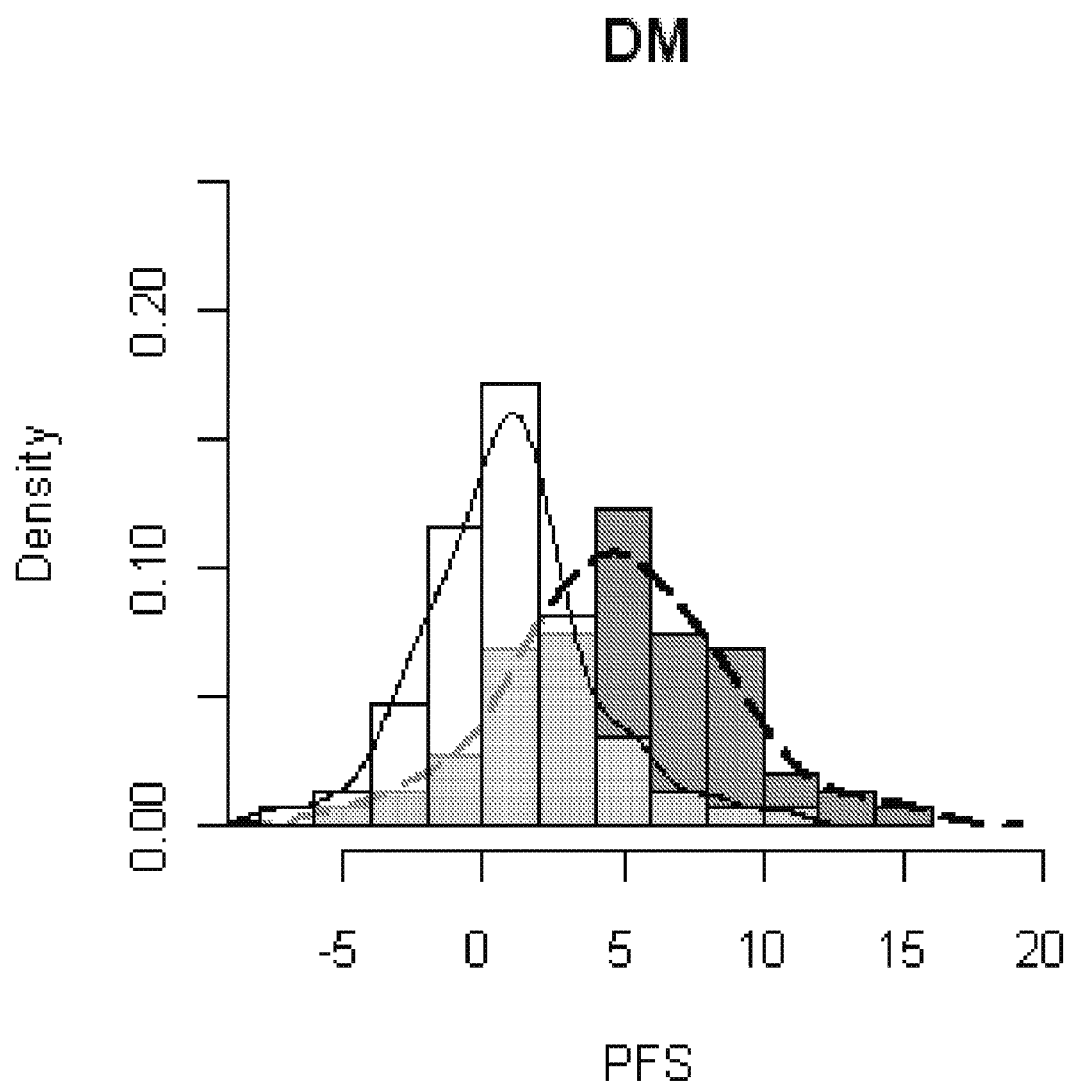
Figure 4:
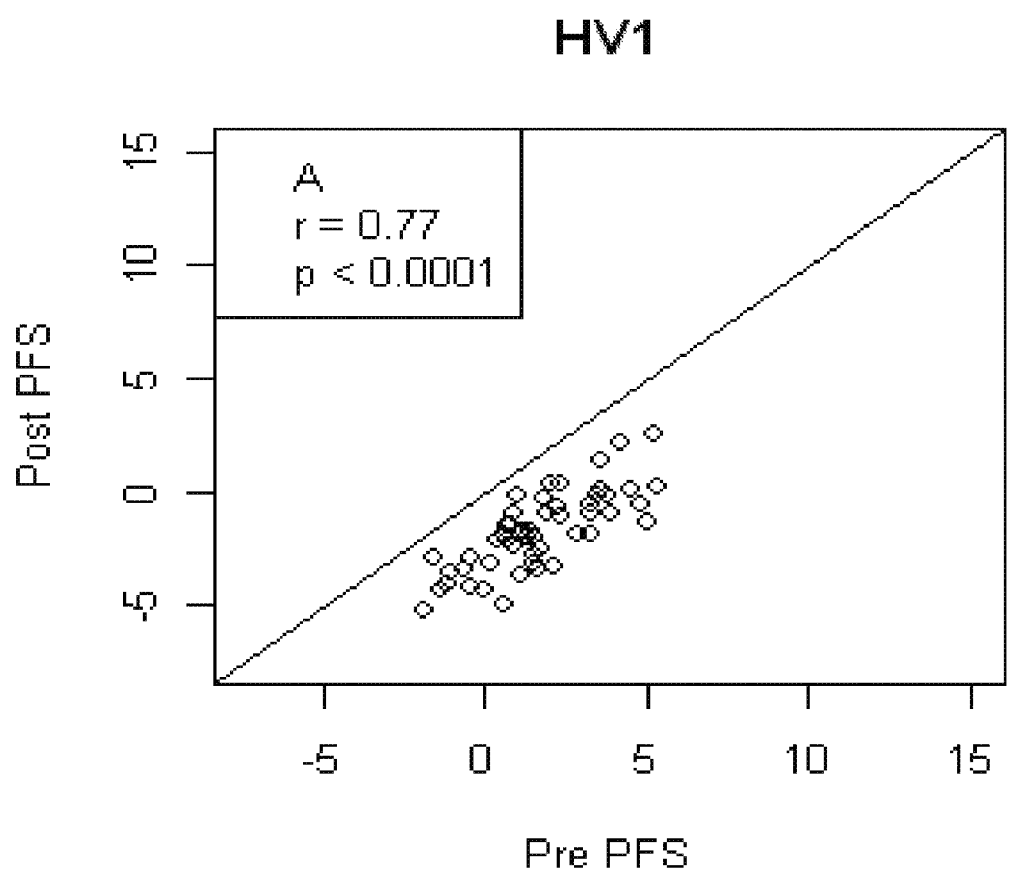
FIG. 4 shows that pre aspirin PFS predicted Post aspirin PFS. Relationship between non COX-1 dependent platelet function measured pre-aspirin (Pre PFS, on x-axis) and the immediately after the first 325 mg aspirin dose (Post PFS, on y-axis) in two cohorts of healthy volunteers (A and B) and diabetics (C). Although there is a strong correlation between pre- and post-PFS in each cohort, the effect of aspirin in each cohort is demonstrated by individual points lying below the solid line (slope=1, intercept=0)
Figure 4:
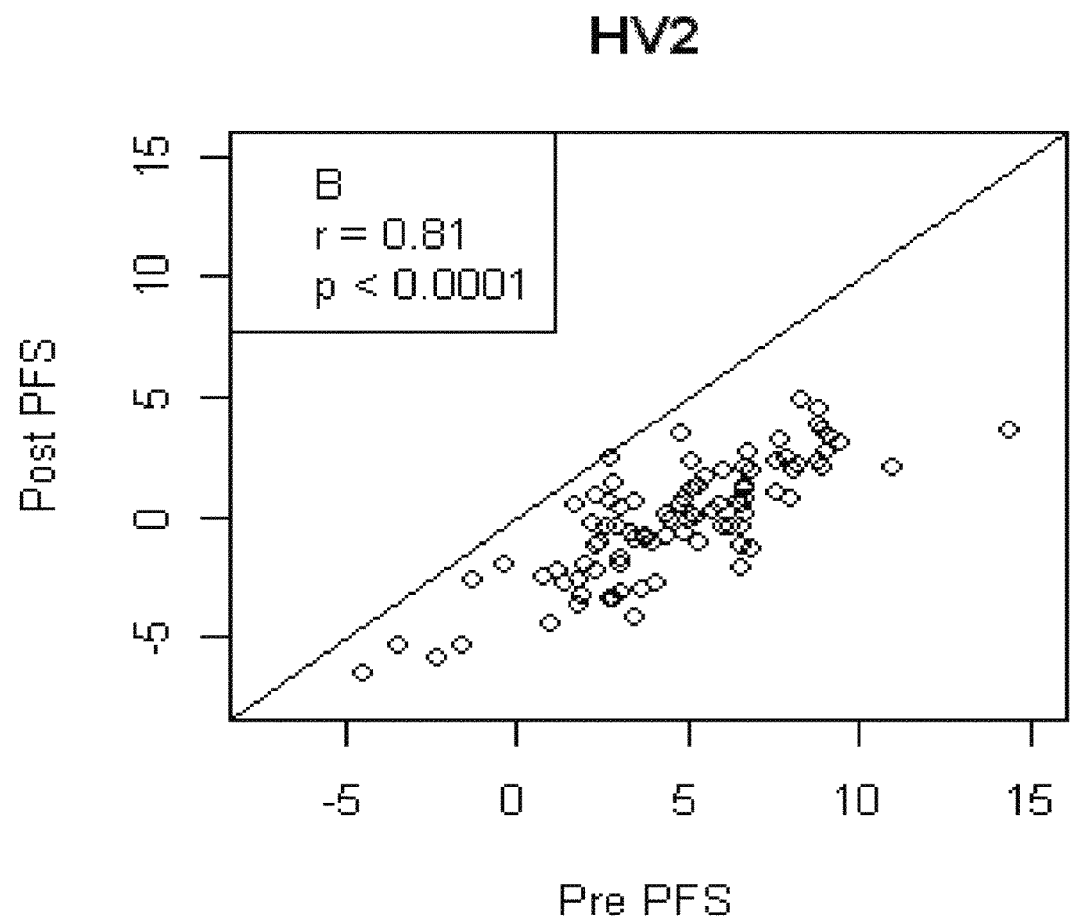
Figure 4:
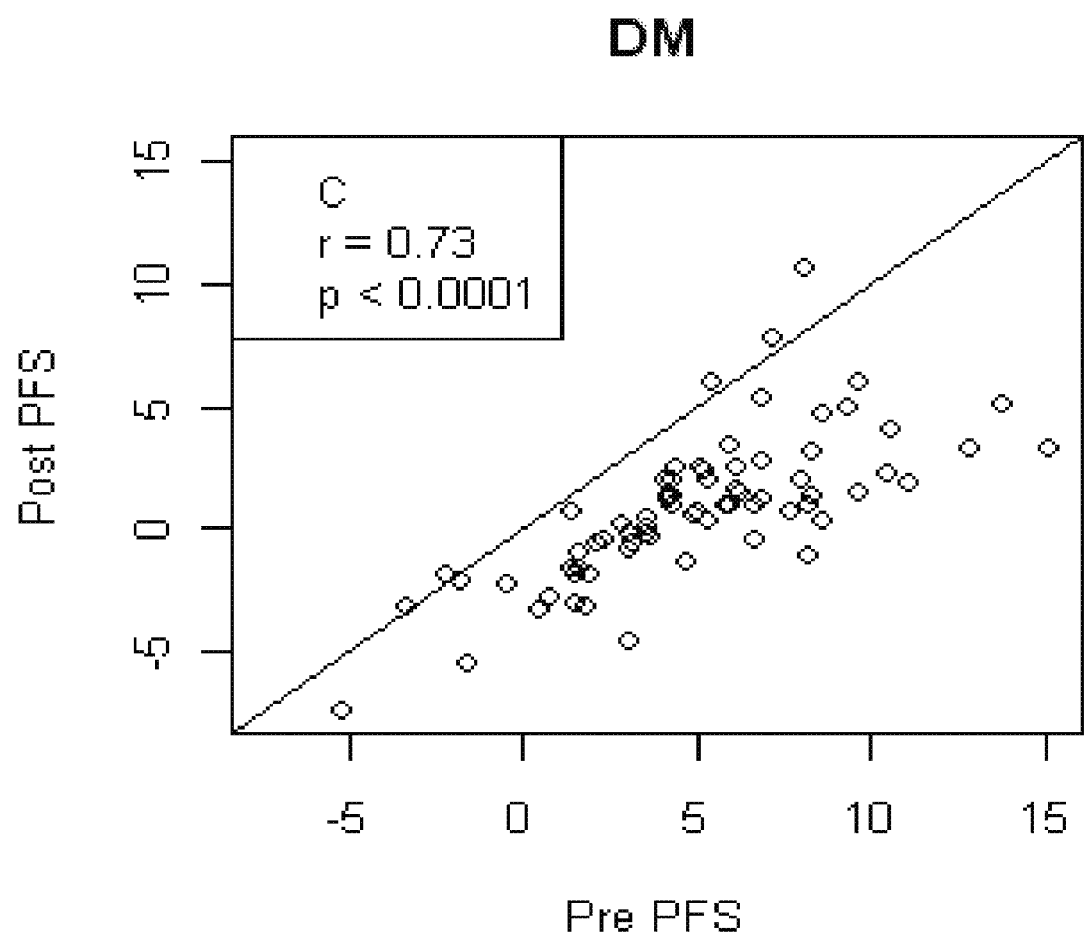

The main measure of NCDPF in this study, the PFS, was sensitive to the influence of aspirin as demonstrated by a significant shift in the PFS distribution to lower values (FIG. 3): mean difference in Pre vs. Post PFS, [95% confidence interval] for HV1, HV2, and DM: 3.4 [3.0-3.7], 4.8 [4.5-5.2], 4.2 [3.6-4.8], paired t-test p-value<0.0001 for all comparisons. In contrast to the uniform suppression of COX-1 dependent platelet function (FIG. 2) after a single 325 mg dose of aspirin, NCDPF persisted and demonstrated wide interindividual variation (FIG. 3). A significant and strong correlation between the Pre and Post PFS was found in all three cohorts (FIG. 4, r=0.77, 0.81, and 0.73 for HV1, HV2, and DM cohorts, respectively; p<0.0001 for all).

Figure 5:
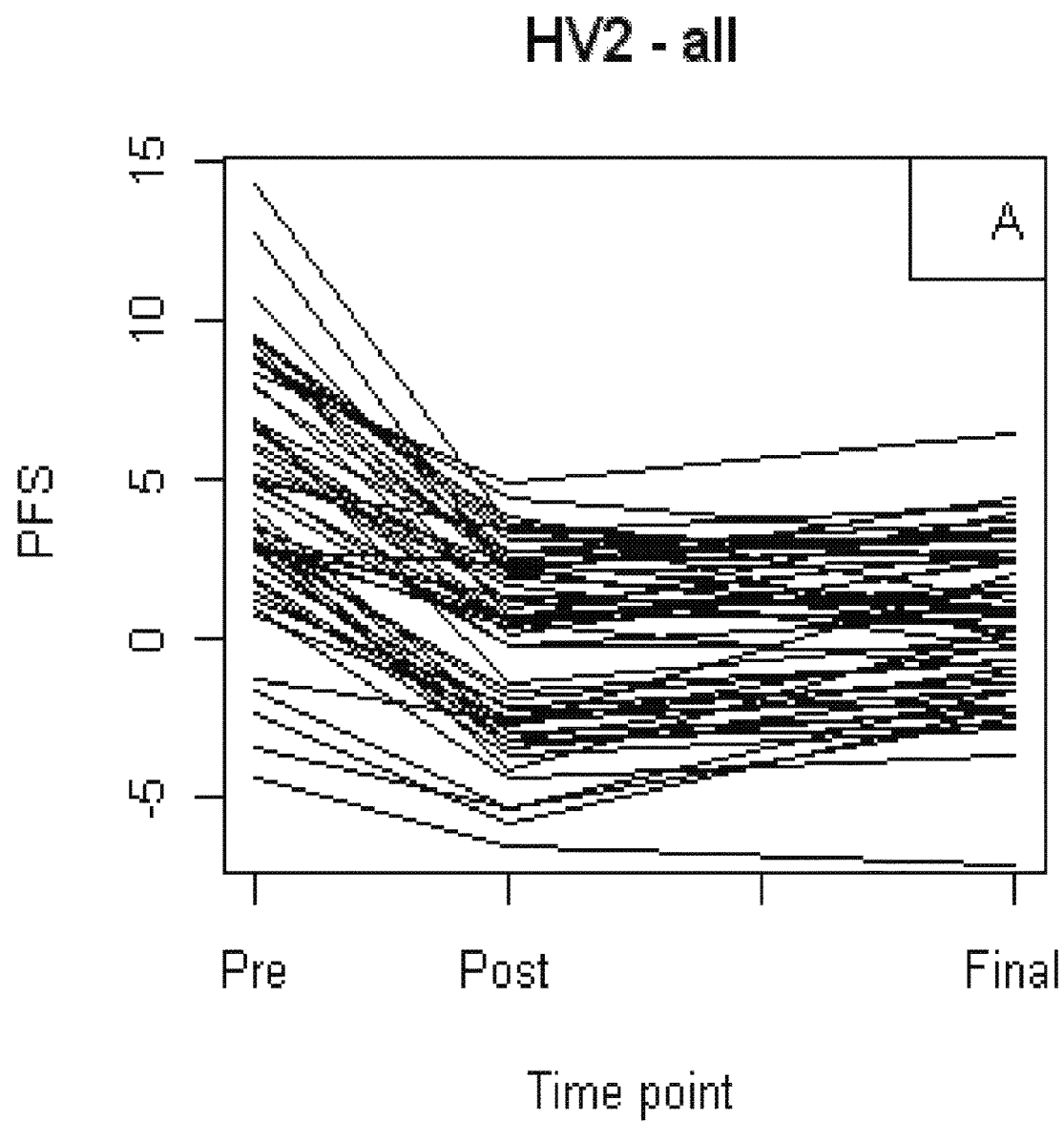
FIG. 5 shows the temporal changes in PFS during daily aspirin therapy. Non COX1 dependent platelet function as assessed by PFS at three time points in HV2 cohort (A): pre-aspirin (Pre), after the first 325 mg dose of aspirin (Post), and after 4 weeks of 325 mg/day aspirin (Final). The HV2 cohort was then divided based on an increase (B) or decrease (C) in PFS over time.
Figure 5:
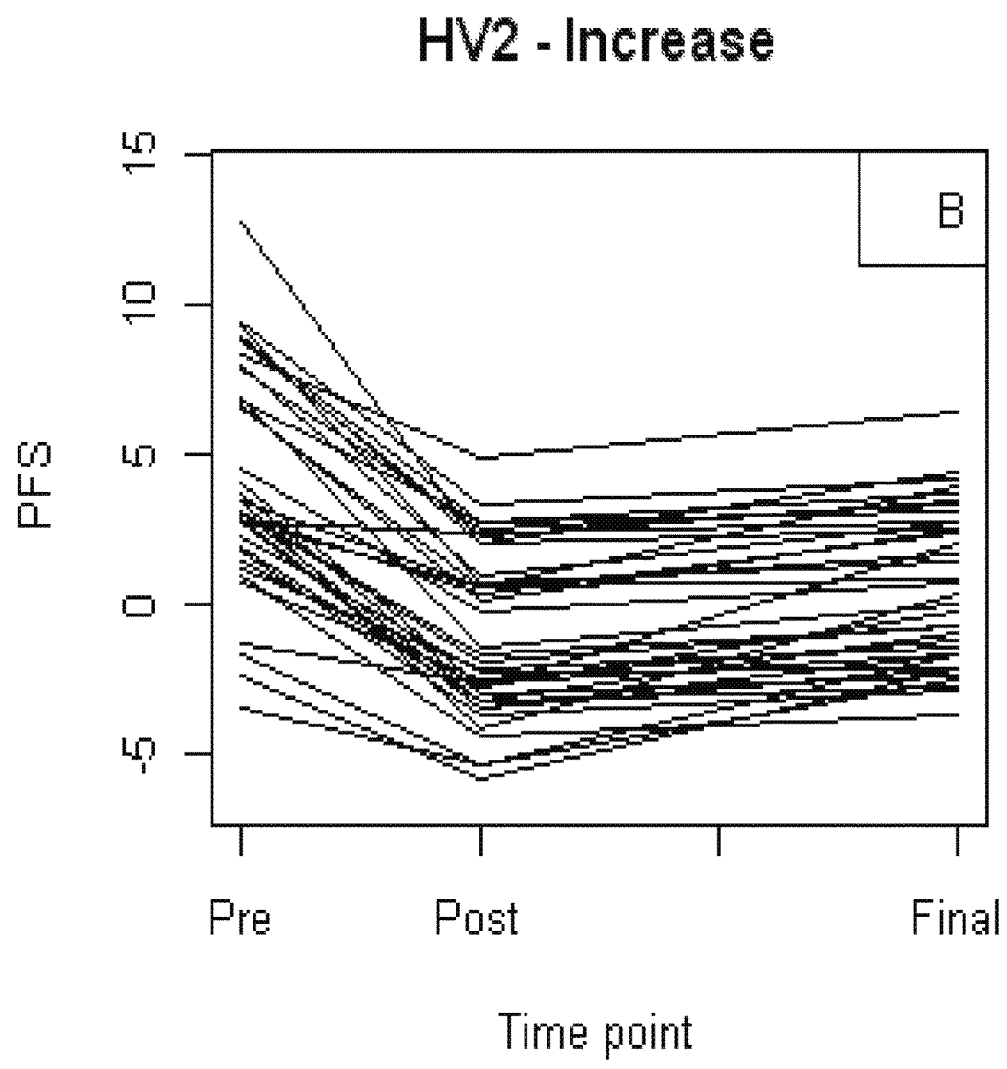
Figure 5:
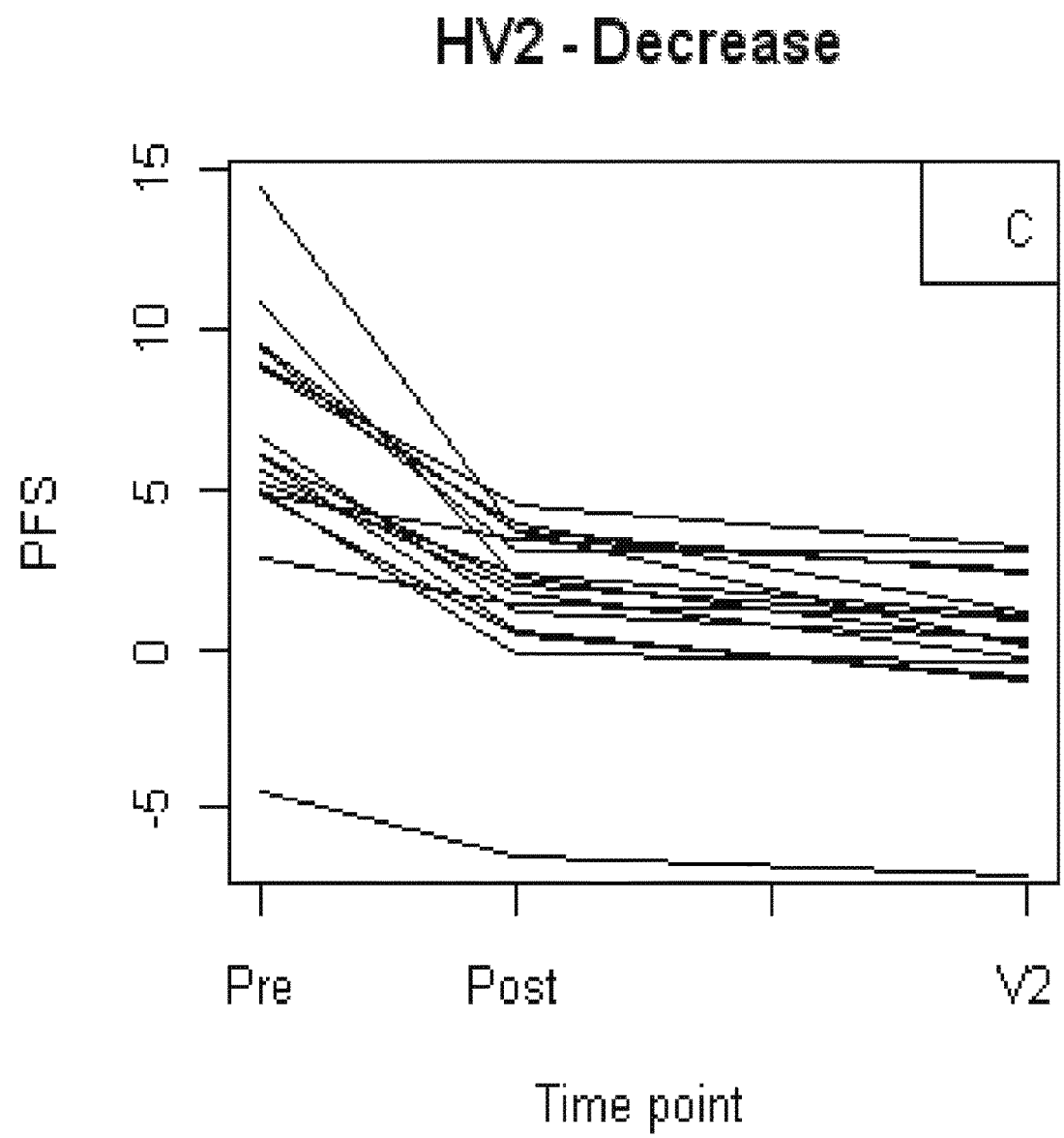

In healthy volunteers, daily aspirin therapy results in a time-dependent shift towards higher NCDPF. After two weeks of aspirin in HV1, a strong correlation was observed between the Post and Final PFS values (r=0.74, p<0.0001). Despite this high degree of correlation, the PFS measured after two weeks of aspirin was shifted higher (mean difference Post and Final PFS=0.5, [0.1-0.8], paired t-test p=0.01) towards pre-aspirin levels of platelet function. In the HV2 cohort, a similar shift to higher PFS after four weeks of aspirin was observed (FIG. 5A, mean difference between Post and Final PFS=0.7, [0.2-1.2], paired t-test p=0.004). This shift towards higher PFS over time was accompanied by a similar trend in most but not all of the individual components of the PFS (epinephrine: paired t-test p-values: <0.05 for 10 and 1 µM in HV1 and <0.008 for all concentrations in HV2; ADP: p=0.07 for µM in HV1, p=0.03 for µM in HV2; Collagen: p<0.005 for 2 µM in HV1 and p<0.07 for all concentrations in HV2; PFA100: p=0.01 for HV1). These observations demonstrate that there was a significant change in NCDPF induced by aspirin in healthy volunteers.

Figure 6:
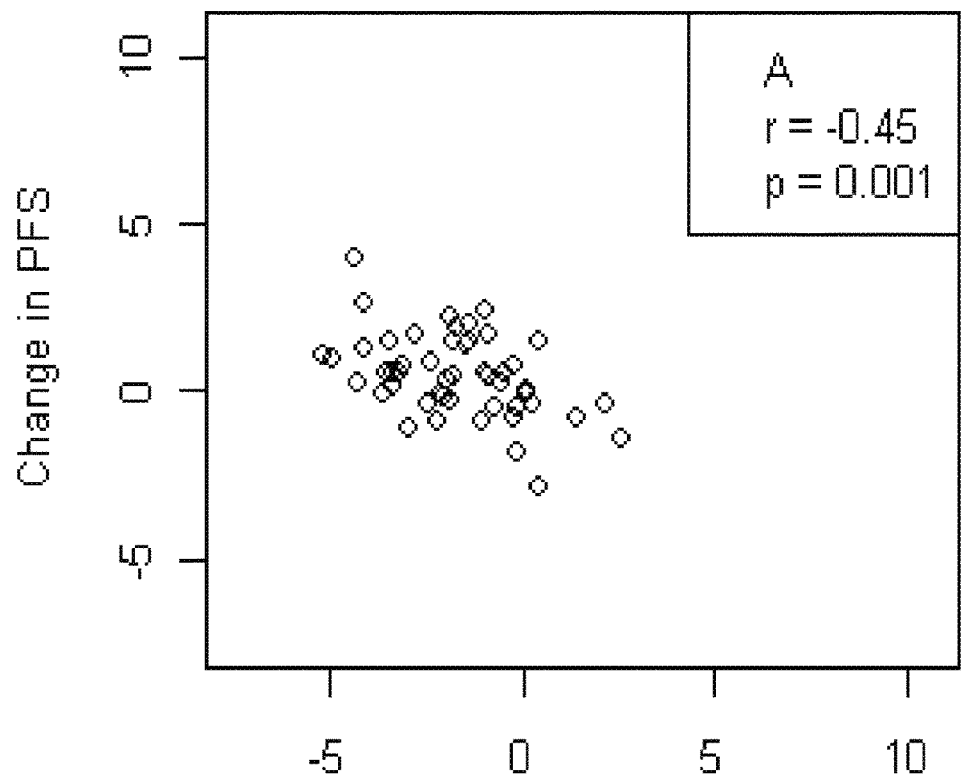
FIG. 6 shows the time-dependent change in PFS on aspirin was a function of acute response. Change in platelet function score (PFS) defined as Final-Post PFS (y-axis) vs. Post PFS (x-axis) in HV1 cohort (A), HV2 cohort (B), diabetics (DM, C), and in all subjects (D). Open circles=healthy volunteers. Crosses=diabetics. The magnitude and direction of the change in PFS over time is inversely proportional to the initial response to aspirin in each cohorts.
Figure 6:
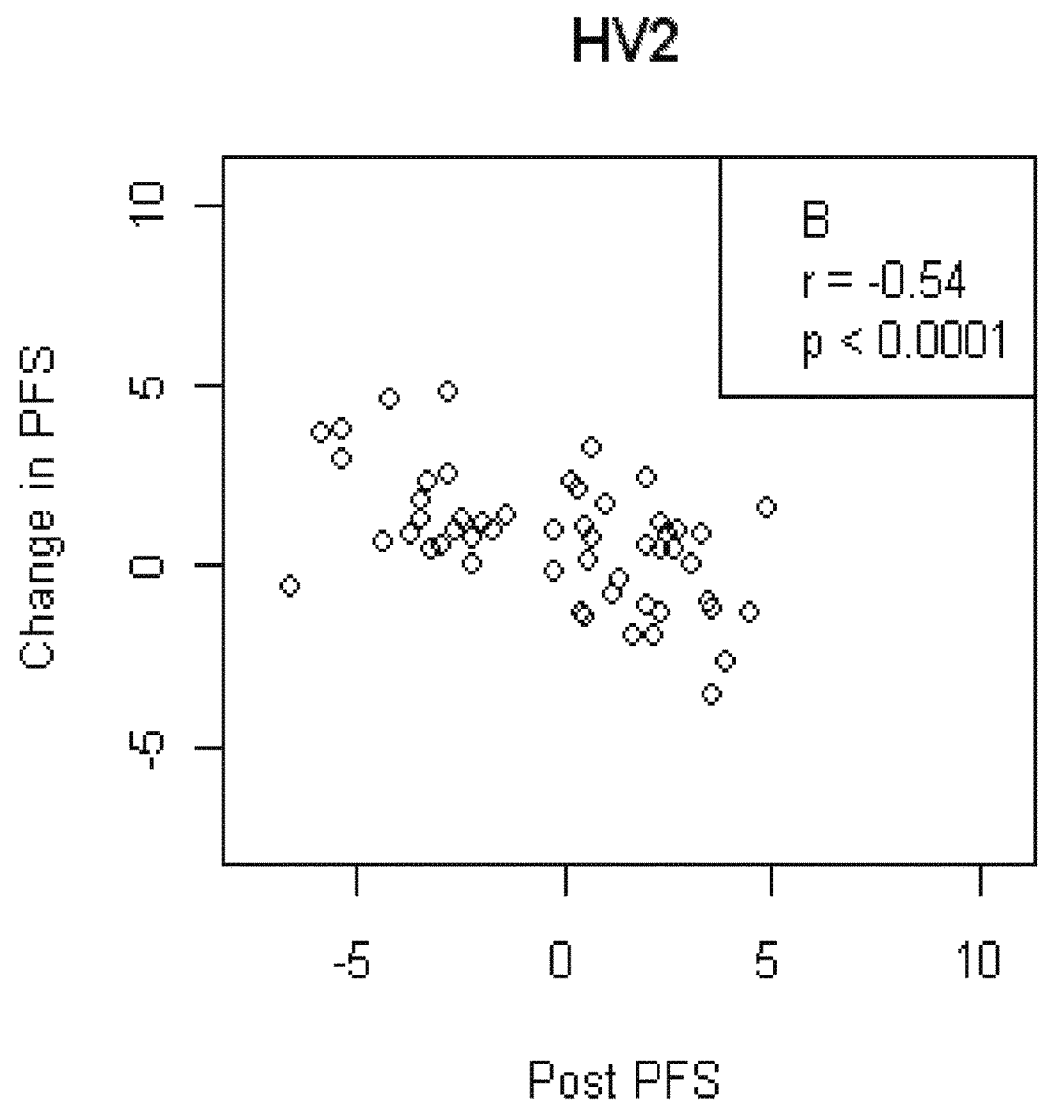
Figure 6:
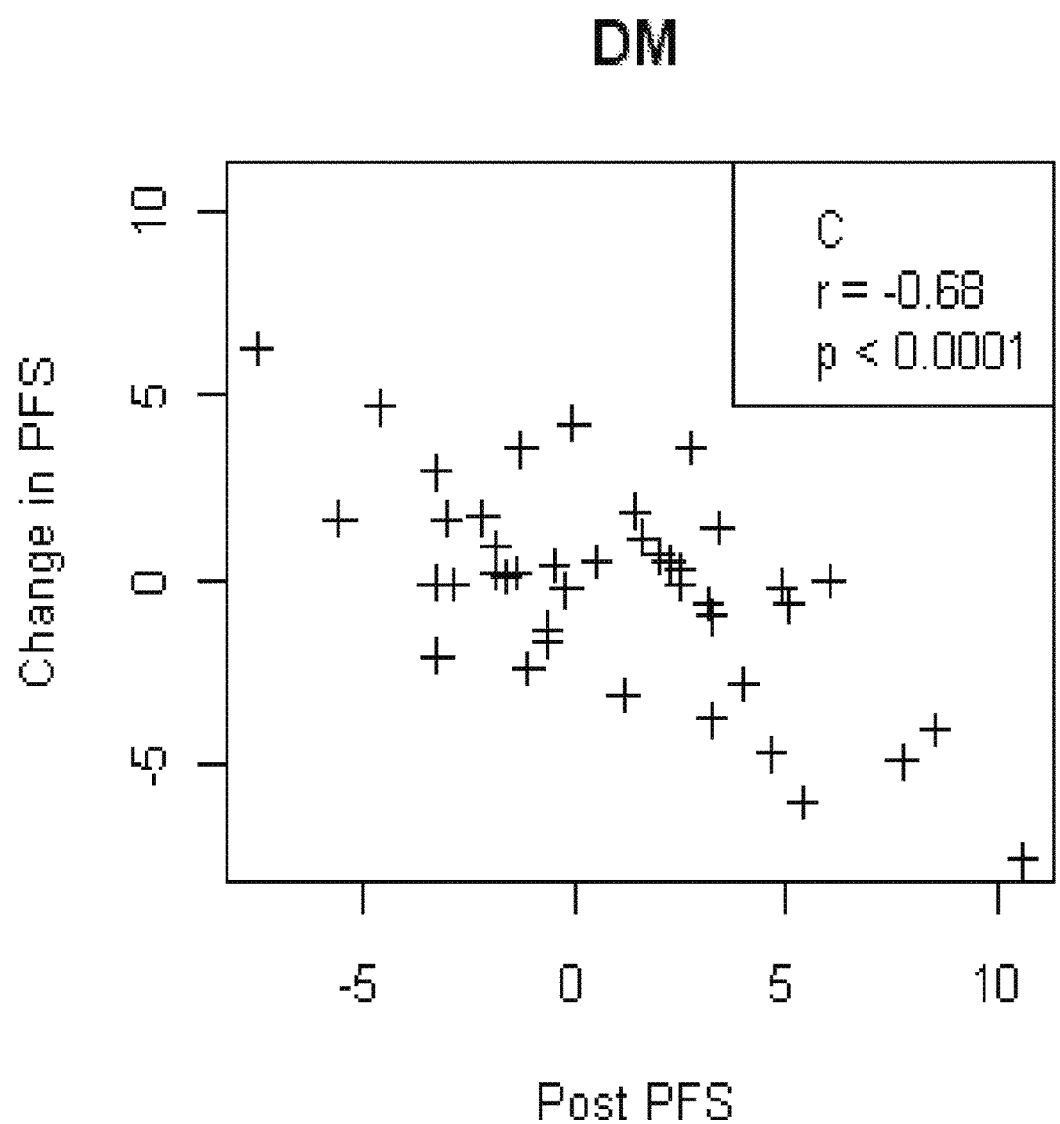
Figure 6:
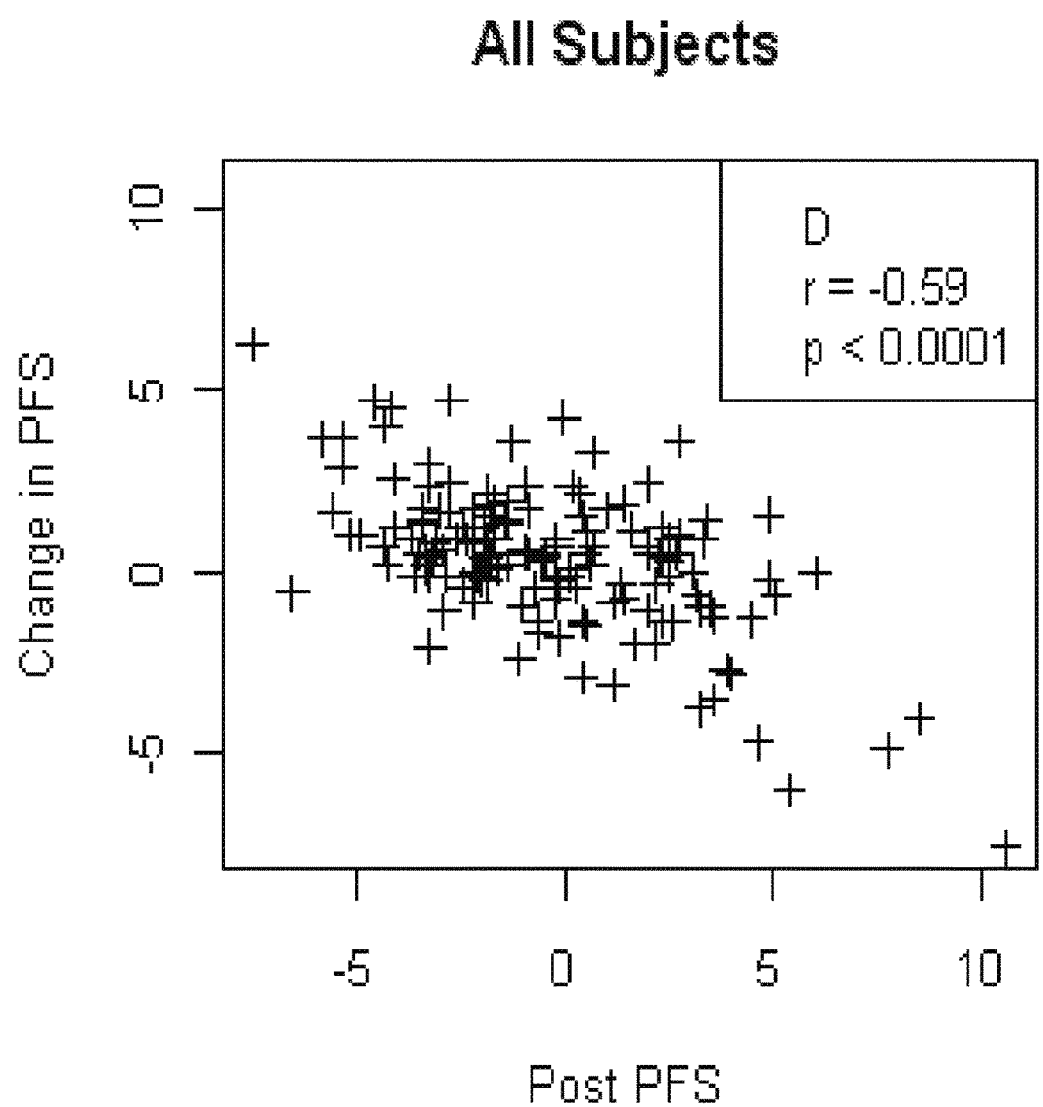

Heterogeneity in the change in NCDPF during aspirin exposure depended on initial response to aspirin. Although on average PFS increased during aspirin exposure in both groups of healthy volunteers, on inspection of the individual trends in HV2 (FIG. 5A) it was apparent that there was heterogeneity in these trends with some trending to higher Final PFS and others trending to lower Final PFS values. Stratifying the HV2 cohort based on those that increased their Final PFS (FIG. 5B) vs. those that decreased their Final PFS (FIG. 5C) demonstrated that the Post PFS was significantly different (Post PFS in those that increased vs. decreased PFS: —1.0 vs. 1.68, t-test p=0.002) between groups. To better characterize this heterogeneity, the change in PFS (Final-Post) and the Post PFS was correlated in the HV1 cohort and found an inverse correlation (r=−0.45, p=0.001, FIG. 6A), suggesting that the basis for the direction and magnitude of change in PFS during aspirin therapy was the initial response to aspirin. To validate this observation, an inverse correlation in HV2 and DM was hypothesized. A pattern in the same direction and with a greater strength as in the HV1 cohort was found (HV2: r=−0.54, p<0.0001, FIG. 6B; DM: r=−0.68, p<0.0001, FIG. 6C). Combining data from all three cohorts, the PFS after the first dose of aspirin was significantly correlated with the change in PFS during aspirin therapy (r=−0.59, p-value<0.0001, FIG. 6D).

The increase in NCDPF induced by aspirin is not due to uninhibited COX-1. In the HV2 and DM subjects, it was found that AAA (median % aggregation=3.0, range: 0-7%) and in HV2 serum thromboxane B2 concentration (mean concentration=0.3, range 0.1-2.0 ng/ml) remained suppressed and did not correlate with the Final PFS (r<0.2, p>0.3).

To demonstrate that the change in NCDPF induced by aspirin is not due to uninhibited COX1, in a subset of subjects (n=5 HV2 and n=15 DM subjects), the in vitro addition of aspirin was used to test if additional aspirin could further reduce NCDPF. It was found that the in vitro addition of aspirin caused no further reduction in NCDPF using epinephrine 0.5 µM (mean change aggregation with in vitro aspirin=2.0%, [−0.8-4.8%], paired t-test p=0.2), ADP 5 µM (mean change=−2.3% [−6.9-2.4%], paired t-test p=0.3), or collagen 2 mg/ml (mean change=1.5%, [−6.9, 10.0], paired t-test p=0.71).

Example 2

Platelet Function Genes and Cardiovascular Events

Platelet Function Outcomes in Healthy Volunteers Cohorts at Duke University Medical Center (DUMC).

Figure 7:
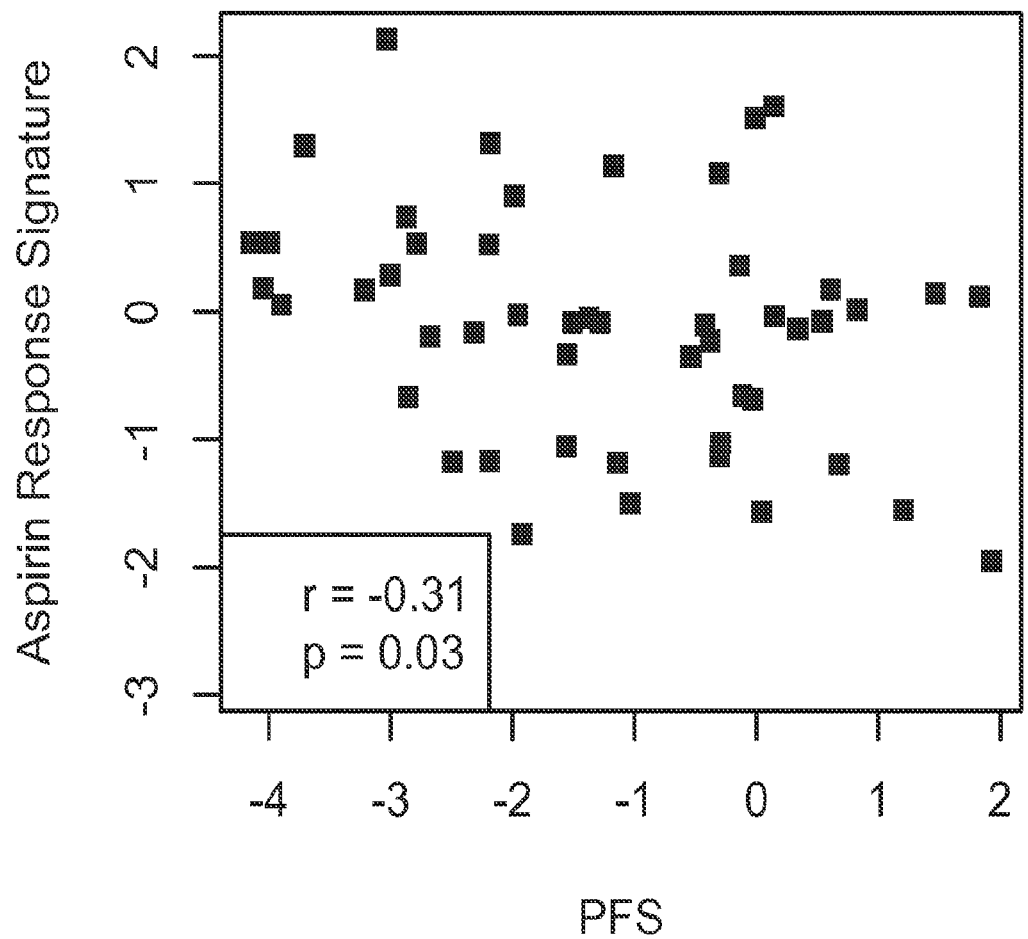
FIGS. 7A-7B shows the aggregate expression of a set of coexpressed, whole blood genes correlates with platelet function in response to aspirin. Two independent cohorts of healthy volunteers (FIG. 7A="Discovery Cohort") and (FIG. 7B="Validation Cohort #1") were exposed to 325 mg/day aspirin, followed by whole blood microarray profiling. Platelet function was assessed by the platelet function score (PFS). The aggregate expression of a set of coexpressed genes (aspirin response signature [ARS], y-axis), is plotted against the PFS (x-axis) after aspirin exposure. Pearson correlation coefficients and p-values are reported.
Figure 7:
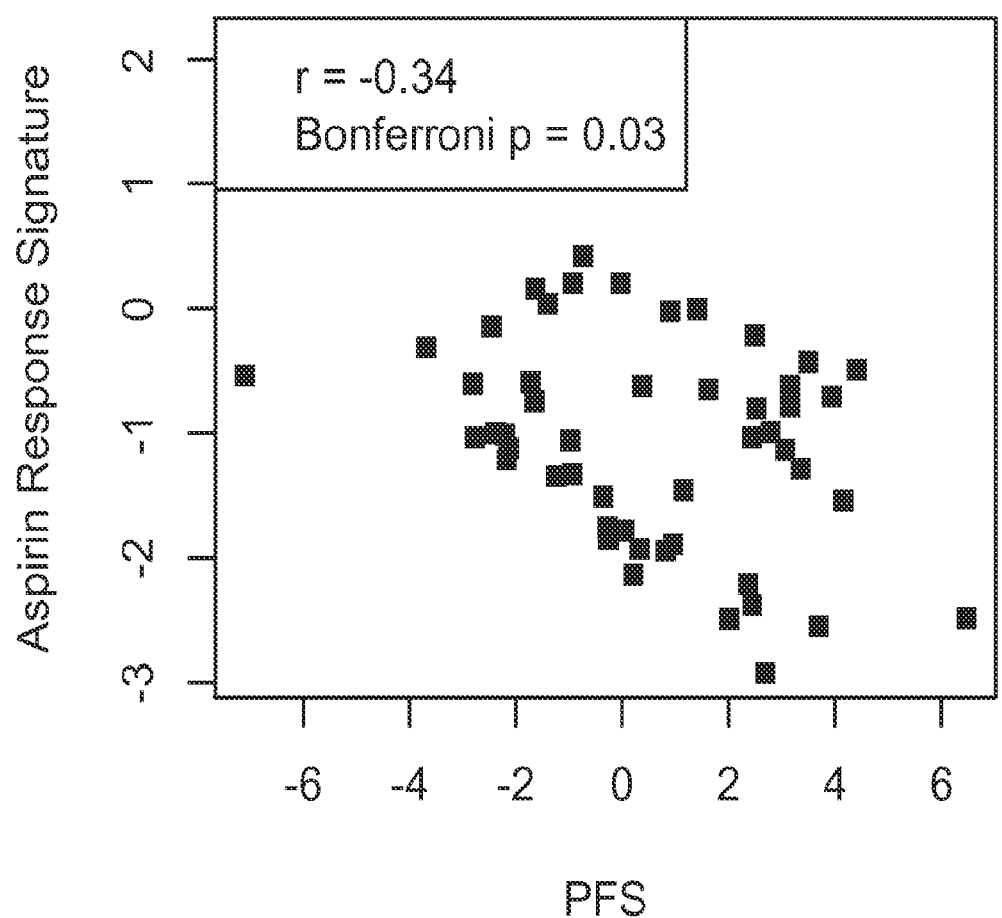

Example 1 describes discovery and validation healthy volunteer cohorts (HV1 and HV2, FIGS. 7A-7B) and the platelet function score (PFS)—a composite metric of the following platelet function assays: PFA100 (collagen/epinephrine) closure time and the areas under the optical aggregometry curve induced by adenosine diphosphate (10, 5, 1 µM), epinephrine (10, 1, 0.5 µM), and collagen (5, 2 mg/ml). The PFS and mean platelet volume (MPV) was measured in HV1 (n=50) after 2 weeks of dosing with 325 mg/day non-enteric coated, immediate release aspirin and HV2 (n=53) after 4 weeks of dosing with 325 mg/day aspirin. In both cohorts whole blood RNA was collected into PAXgene® Blood RNA tubes (Becton, Dickinson, N.J., USA) before after aspirin exposure and stored at −80° C. until microarray profiling. Platelet count was measured in platelet rich plasma in HV1. Because three subjects in HV2 had participated in HV1, these were dropped from HV2, leaving 50 unique HV2 subjects.

Platelet Function Outcomes in Patients at Risk for Cardiovascular Events at George Washington University (GWU).

Figure 16:
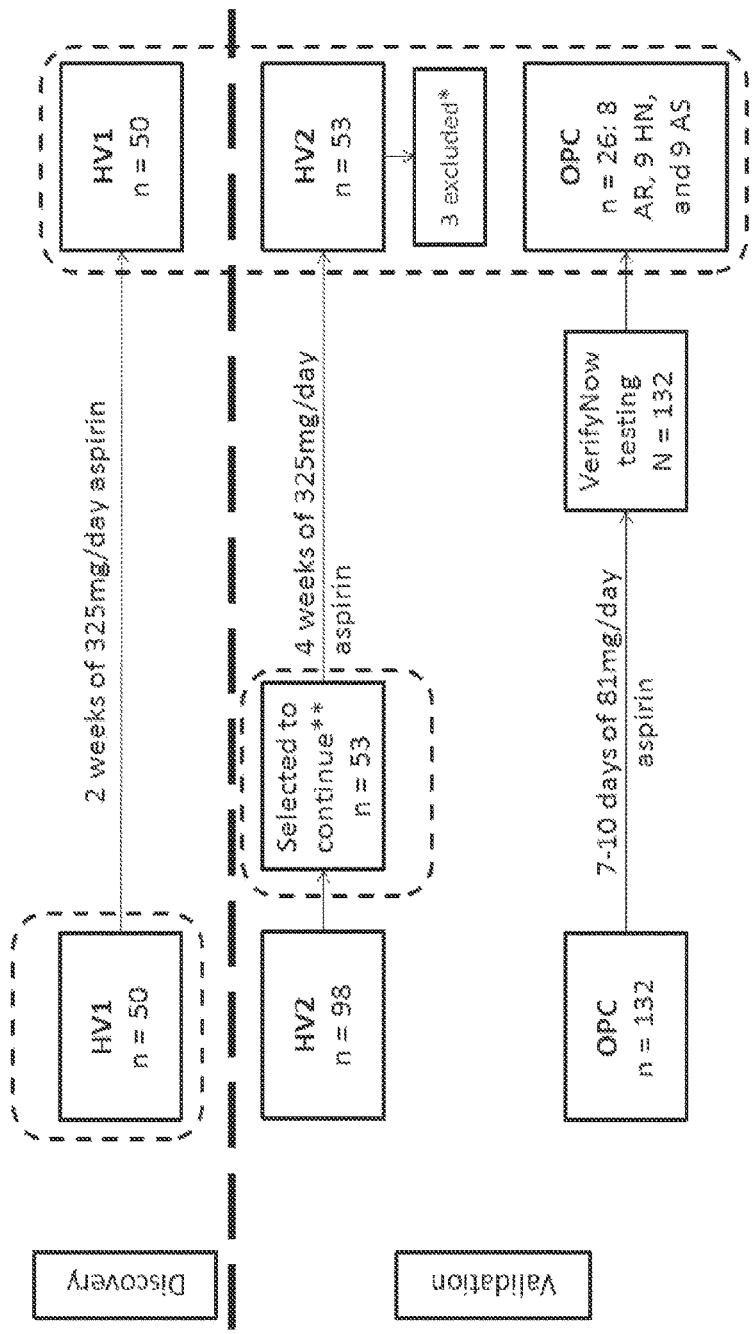
FIG. 16 shows an overview of the discovery and validation cohorts for platelet function outcomes and samples analyzed by microarray analysis (dashed outline). Healthy volunteers cohorts (HV1 and HV2) were challenged with 325 mg/day aspirin at Duke University Medical Center as previously described in Example 1. Outpatient cardiology (OPC) patients were treated with 81 mg/day aspirin at The George Washington University. Three subgroups within the OPC cohort were selected for microarray analysis based on VerifyNow Aspirin Response Units (ARU): aspirin resistant (AR, ARU>550), High normal (HN, 500<ARU<550); and Aspirin sensitive (AS, ARU<550). **HV2 subjects were screened with a test dose of 325 mg aspirin and those in the $1^{st}$ and $4^{th}$ quartile of the 3 hour platelet function score (PFS) were selected to continue through the study protocol. *Three HV2 subjects had participated in HV1 and were dropped from the HV2 cohort.

An outpatient cardiology cohort (OPC, FIG. 16) treated with 81 mg/day aspirin were assessed with the VerifyNow Aspirin device and whole blood RNA microarray analysis as previously described in (Fallahi et al., (2013) Gene 520(2): 131-138).

Example 3

Clinical Outcomes in DUMC Patients

Figure 17:
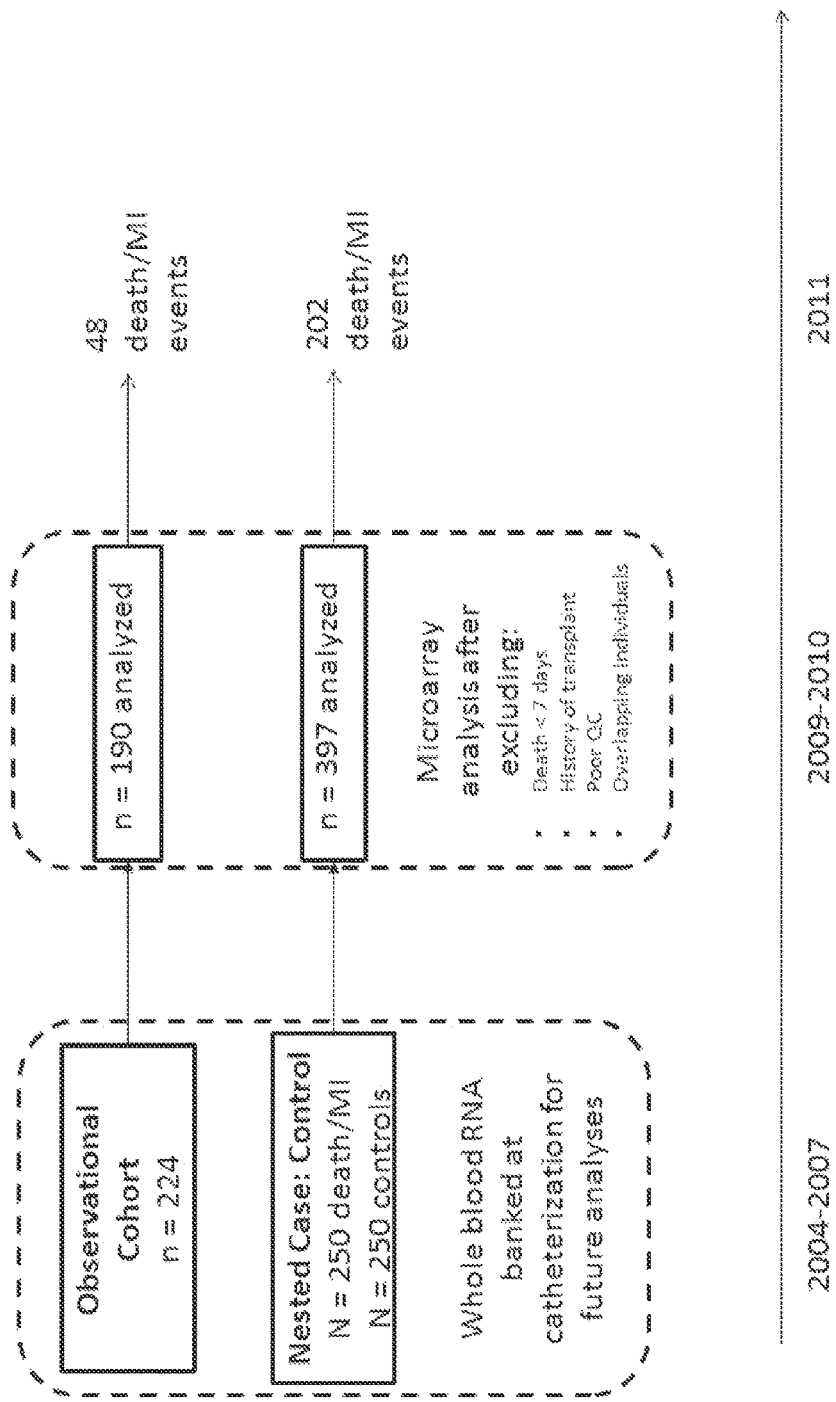
FIG. 17 shows two patient cohorts from within the CATHGEN biorepository were available for microarray analysis. In 2009, an observational cohort of 224 banked, sequential samples were selected, of which 190 were available for analysis. In 2010, a nested case:control cohort of 250 cases of death/myocardial infarction and 250 age-, sex-, and race-matched controls who were free of death/MI>2 years after cardiac catheterization was identified as part of the MURDOCK Horizon 1 Cardiovascular Disease Study (Shah et al., Am Heart J (2010) 160:371-379 e2), of which 397 were available for analysis. In 2011, dates for death, myocardial infarction, and last follow-up were ascertained from the Duke Databank for Cardiovascular Disease as previously described (Voora et al., Am Heart J (2011) 162:166-172 e1).
Figure 18:
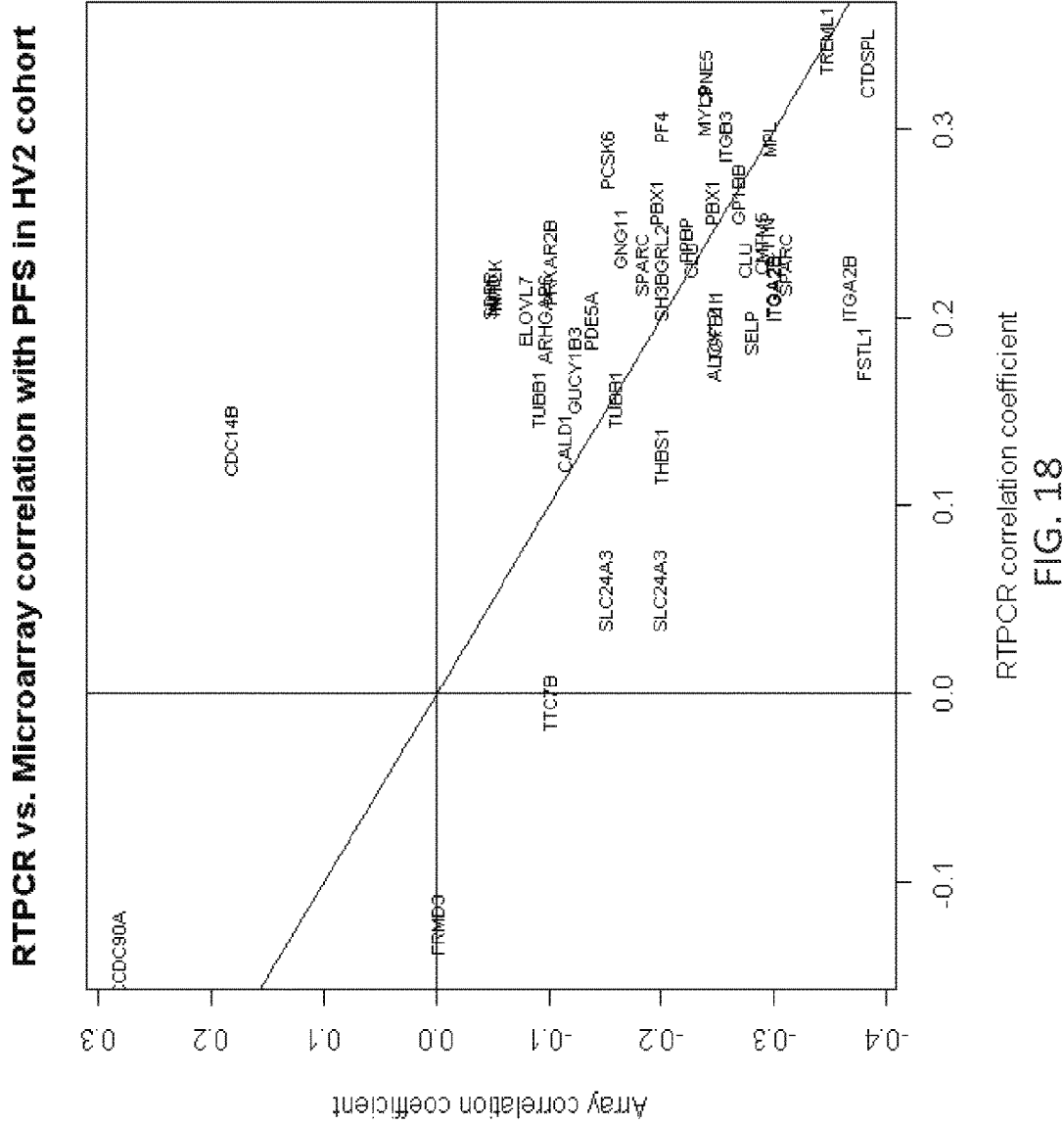
FIG. 18 shows concordance between RTPCR vs. microarray correlations with platelet function score (PFS). The correlation (Ct vs. PFS) of RT-PCR based gene expression of Factor 14 genes with PFS in HV2 whole blood RNA (x-axis) is plotted against the microarray based correlation (probe set expression vs. PFS) for the same genes (y-axis). For the vast majority of Factor 14 genes there is concordance such that the correlations using RT-PCR with PFS are in the same direction with microarray based correlations. Many RT-PCR correlations are stronger than microarray based correlations (i.e. point is above the line of unity)
Figure 19:
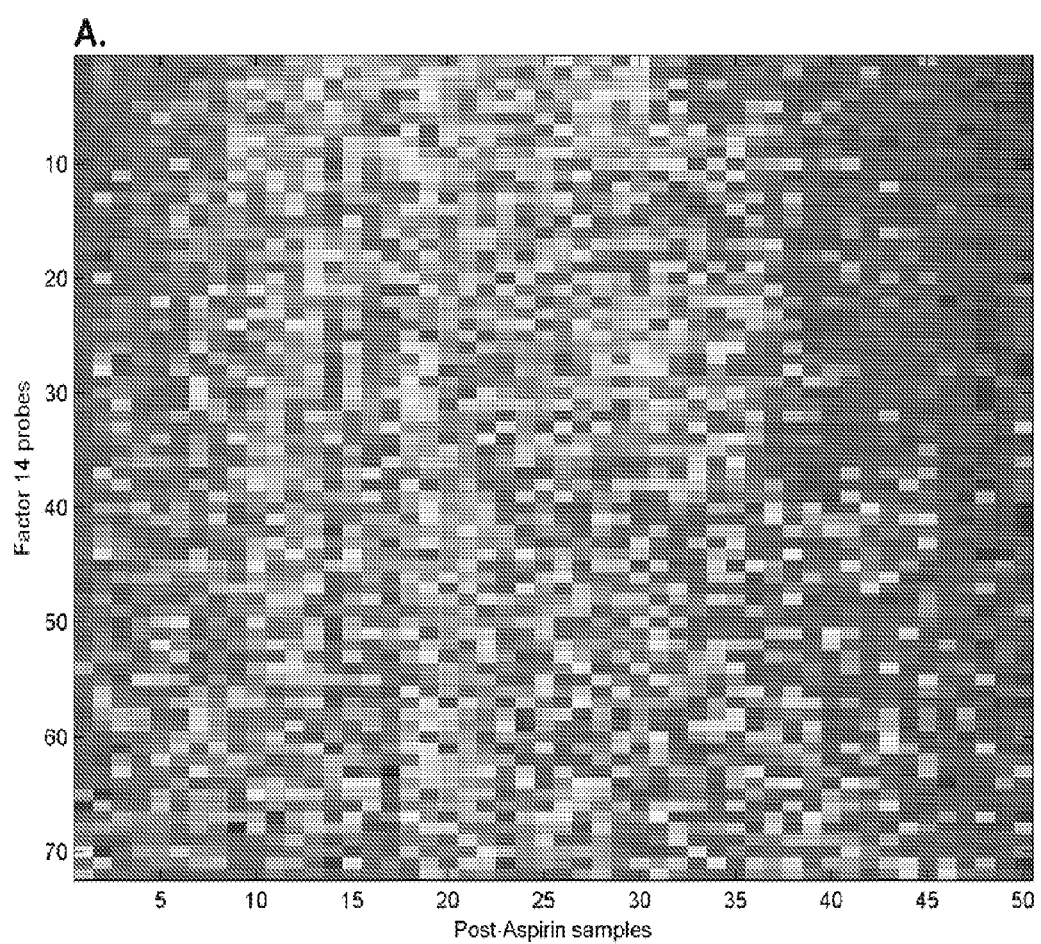
FIG. 19 shows that the genes represented by Factor 14 are tightly co-expressed before and after the administration of aspirin. The set of Factor 14 transcripts in the HV1, post-aspirin dataset were ordered based on their correlation with the first principal component of their expression values and visualized using a heatmap (panel A). The order of the probe sets was then used to generate a heatmap of the pre-aspirin set of transcripts from the same individuals (panel B). Within an individual (columns) there is a similar pattern of gene expression (i.e., predominatnly under or over expressed) both before and after aspirin exposure. Therefore, aspirin exposure is unrelated to the coordinated expression of this set of transcripts.
Figure 19:
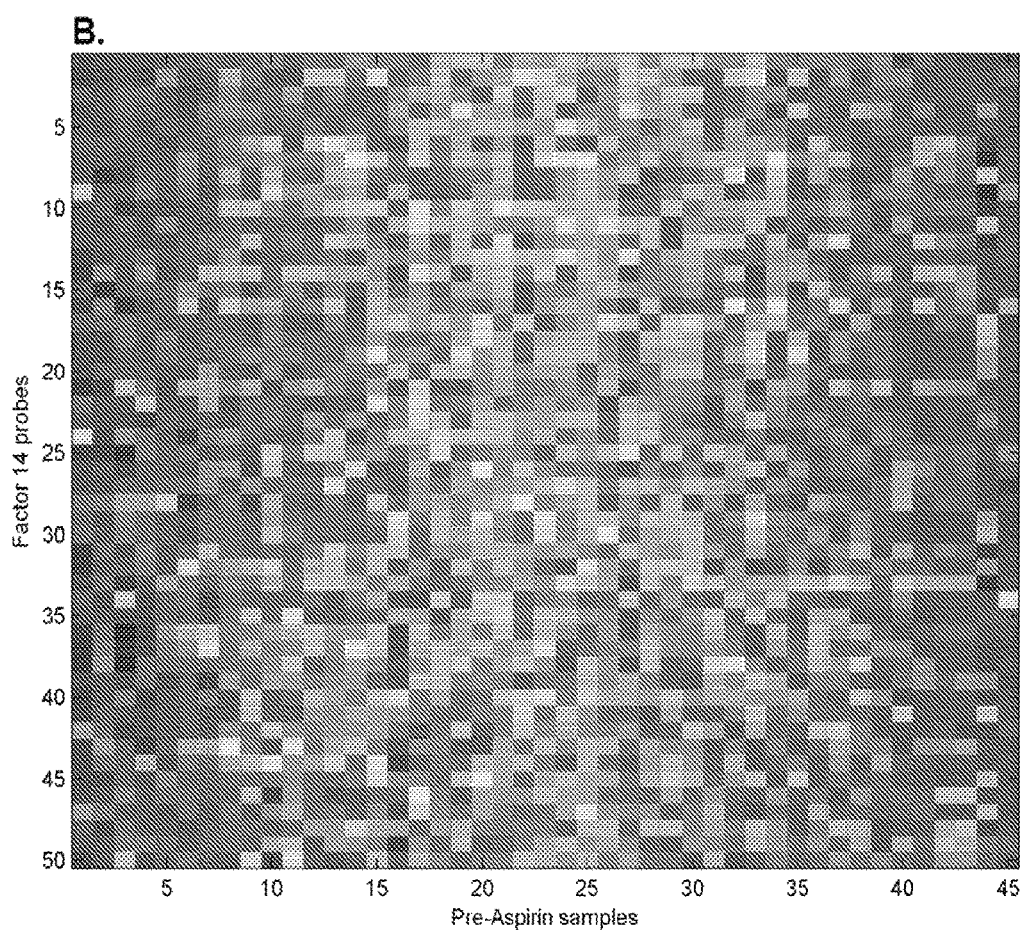

CATHGEN biorepository. The Catheterization Genetics (CATHGEN) biorepository at Duke University has banked, whole blood RNA in PAXgene® tubes (Qiagen; Valencia, Calif.) from DUMC patients from the time of cardiac catheterization, baseline medical history, and follow up for all-cause death and MI. Two cohorts had available microarray data (FIG. 17):

Observational Cohort:

224 sequential samples were selected for RNA analysis, of which, 191 had sufficient RNA for microarray analysis.

Case:Control Cohort:

A nested case:control cohort of participants who had experienced death or MI (n=250) after their index catheterization and age-, sex-, and race-matched controls (n=250) who were free of death/MI>2 years after cardiac catheterization was identified (Shah et al., Am Heart J (2010) 160:371-379 e2). 447 had sufficient RNA for microarray analysis; 44 overlapped with the observational cohort and were dropped, leaving 403 subjects for analysis.

Follow-up for death/MI was ascertained in both cohorts; the median follow-up was 3.8 years. Patients with incomplete follow-up were censored at the time of last contact. Patients who had a history of cardiac transplantation at the time of catheterization (n=5), died within seven days (n=1), or failed quality control (n=1) were excluded. The remaining datasets left 190 samples in the observational cohort (48 death/MI events) and 397 (202 death/MI events) in the case-control cohort.

RNA Extraction, Labeling, Microarray Hybridization, Quality Control, and Normalization.

Two microarray platforms were utilized: Affymetrix U133A2 array (HV-1, pre-aspirin) and U133 plus 2.0 array (all others). The Robust Multichip Average (RMA) method was used for normalization.

DUMC HV1 and HV2 Samples

RNA Extraction

Total RNA was extracted using the PAXgene® Blood RNA Kit (Qiagen, Valencia, Calif.) following the manufacturer's recommended protocol including DNase treatment. Following isolation, RNA quantity was determined via a Nanodrop UV-Vis Spectrophotometer (Thermo Fisher Scientific, Pittsburgh, Pa.) and quality via capillary electrophoresis using the Agilent 100 Bioanalyzer (Agilent, Santa Clara, Calif.).

Microarray Analysis

HV1 and HV2 samples were analyzed in three separate batches (June 2009, July 2010, and February 2011) at Expression Analysis (Durham, N.C.) using the GeneChip® Human Genome U133 2.0 array (Affymetrix, Santa Clara, Calif.) for the all HV2 and HV1 post-aspirin samples and the U133A2 array for the HV1 pre-aspirin samples. Target was prepared and hybridized according to the "Affymetrix Technical Manual". A set of four peptide nucleic acid (PNA) oligomers (Applied Biosystems, Foster City, Calif.) with sequences complimentary to globin mRNA were added to 2.5 µg of total RNA to reduce globin RNA transcription, then converted into cDNA using Reverse Transcriptase (Invitrogen) and a modified oligo(dT)24 primer that contains T7 promoter sequences (GenSet). After first strand synthesis, residual RNA was degraded by the addition of RNaseH and a double-stranded cDNA molecule was generated using DNA Polymerase I and DNA Ligase. The cDNA was then purified and concentrated using a phenol:chloroform extraction followed by ethanol precipitation. The cDNA products were incubated with T7 RNA Polymerase and biotinylated ribonucleotides using an In Vitro Transcription kit (Affymetrix). The resultant cRNA product was purified using an RNeasy column (Qiagen) and quantified with a spectrophotometer. The cRNA target (20 µg) was incubated at 94° C. for 35 minutes in fragmentation buffer (Tris, MgOAc, KOAc). The fragmented cRNA was diluted in hybridization buffer (MES, NaCl, EDTA, Tween 20, Herring Sperm DNA, Acetylated BSA) containing biotin-labeled OligoB2 and Eukaryotic Hybridization Controls (Affymetrix). The hybridization cocktail was denatured at 99° C. for 5 minutes, incubated at 45° C. for 5 minutes and then injected into a GeneChip cartridge. The GeneChip array was incubated at 42° C. for at least 16 hours in a rotating oven at 60 rpm. GeneChips were washed with a series of nonstringent (25° C.) and stringent (50° C.) solutions containing variable amounts of MES, Tween20 and SSPE. The microarrays were then stained with Streptavidin Phycoerythrin and the fluorescent signal was amplified using a biotinylated antibody solution. Fluorescent images were detected in a GeneChip® Scanner 3000 and expression data was extracted using the GeneChip Operating System v 1.1 (Affymetrix). All GeneChips were scaled to a median intensity setting of 500.

CATHGEN Samples

RNA Preparation

Peripheral blood samples in the CATHGEN repository were collected from participants in the catheterization laboratory using the PAXgene™ RNA tube collection and storage system (PreAnalytiX, Valencia, Calif.).

Microarray Analysis

The PAXgene™ RNA tubes were thawed for a minimum of 2 hours at room temperature. RNA extraction was performed with the Versagene™ RNA Purification Kit (Gentra Systems, Inc., Minneapolis, Minn.) using their blood extraction protocol. The quality of the RNA was evaluated by Agilent 2100 Bioanalyzer (Agilent Technologies). We performed globin reduction with a standard human GLOBIN-clear™ (Ambion, Austin, Tex.) protocol, confirmed by Agilent 2100 Bioanalyzer. The cRNA probes were produced with the Affymetrix GeneChip™ (Affymetrix, Santa Clara, Calif.) one-cycle in vitro transcription labeling protocol and were hybridized to the Affymetrix U133 2.0 Plus Human array that contains 54,613 transcripts. The microarray hybridization was performed by the Duke Microarray Core Facility (Expression Analysis, Research Triangle Park, N.C.).

Quality Analysis of Microarray Data

Prior to RMA normalization, each individual .CEL file was checked for poor quality and thus inclusion for analysis as described (McCall et al. (2011) BMC Bioinformatics 12:137).

Two quality control metrics were applied to each .CEL file: the normalized unscaled standard error (NUSE) and MA plot generation, i.e., application of a Bland-Altman plot. For a given gene, the NUSE provides a measure of the precision of its expression estimate on a given array relative to the other arrays in the batch. Problematic arrays result in higher standard errors (SEs) than the median SE; therefore, arrays are suspected to be of poor quality if either the median NUSE is greater than 1.0 or they have a larger inter-quartile range (IQR). The MA plots allow pairwise comparison of log-intensity of each array to a reference array. Specifically, the y-axis of each plot contains the log-ratio intensity of one array to the reference median (namely "M"); the x-axis contains the average log-intensity of both arrays (namely "A") and the plot is expected to be centered around the y=0 axis from low to high intensities. Lastly, a smooth Loess regression curve is plotted to facilitate comparison to the y=0 axis. Drastic departures in the smoothed regression curve from the y=0 axis is suggestive of intensity-dependent biases. The Bioconductor packages "affy" and "affyPLM" in the R software were used to perform these quality control metrics.

Of all arrays evaluated, only a single array from the CATHGEN case:control cohort was found to be of poor quality (1833_85195_H133+_19655 200514183.CEL) and was dropped from subsequent analysis. This particular array had a median NUSE of approximately 1.25 and its MA plot showed severe departure from the y=0 axis. The remaining arrays from each batch were then RMA normalized to log 2 form.

Real-Time PCR.

Forty-five transcripts were selected for verification in the original RNA samples based on two criteria: 1) the strength of correlation of the probe set with PFS and 2) the strength of membership between the probe set and the set of co-expressed genes of interest.

Assay Selection and UMapIt

Where possible, assays were selected with probes and primers that span exon boundaries and are located near 3' end of transcript. See Table 4. These assays were custom plated into a 384 well format TaqMan™ Low Density Array Card (TLDA; Life Technologies; Grand Island, N.Y.) for use in this PCR experiment.

TABLE 4

| Array Probe ID | Gene Symbol | Closest Inventoried TaqMan ® Assay to 3' end |
| --- | --- | --- |
| 207206_s_at | ALOX12 | Hs00167524_m1 |
| 212077_at | CALD1 | Hs00921982_m1 |
| 221556_at | CDC14B | Hs00269351_m1 |
| 208791_at | CLU | Hs00971656_m1 |
| 230942_at | CMTM5 | Hs00370784_m1 |
| 227189_at | CPNE5 | Hs00326218_m1 |
| 201906_s_at | CTDSPL | Hs00505109_m1 |
| 201059_at | CTTN | Hs01124225_m1 |
| 227180_at | ELOVL7 | Hs00405151_m1 |
| 230645_at | FRMD3 | Hs00604157_m1 |
| 208782_at | FSTL1 | Hs00907496_m1 |
| 208401_s_at | GLP1R | Hs01006332_m1 |
| 204115_at | GNG11 | Hs00914578_m1 |
| 206655_s_at | GP1BB | Hs00236857_m1 |
| 203819_s_at | IGF2BP3 | Hs00559907_g1 |
| 206493_at | ITGA2B | Hs01116228_m1 |
| 204628_s_at | ITGB3 | Hs01001469_m1 |
| 203414_at | MMD | Hs00948031_m1 |
| 207550_at | MPL | Hs00180489_m1 |
| 217071_s_at | MTHFR | Hs00293639_s1 |
| 201058_s_at | MYL9 | Hs00697086_m1 |
| 212148_at | PBX1 | Hs00295499_s1 |
| 207414_s_at | PCSK6 | Hs00159844_m1 |
| 227088_at | PDE5A | Hs00903251_m1 |
| 206390_x_at | PF4 | Hs00236998_m1 |
| 214146_s_at | PPBP | Hs00234077_m1 |
| 203680_at | PRKAR2B | Hs00176966_m1 |
| 222717_at | SDPR | Hs00190538_m1 |
| 206049_at | SELP | Hs00356351_m1 |
| 225354_s_at | SH3BGRL2 | Hs00230283_m1 |
| 57588_at | SLC24A3 | Hs00221141_m1 |
| 200665_s_at | SPARC | Hs00277762_m1 |
| 209651_at | TGFB1I1 | Hs00210887_m1 |
| 201108_s_at | THBS1 | Hs00962914_m1 |
| 1555659_a_at | TREML1 | Hs00698316_m1 |
| 226152_at | TTC7B | Hs00406077_m1 |
| 230690_at | TUBB1 | Hs00258236_m1 |
| 206167_s_at | ARHGAP6 | Hs00241801_m1 |
| 227451_s_at | CCDC90A | Hs00254417_m1 |
| 203817_at | GUCY1B3 | Hs00168336_m1 |
| 224823_at | MYLK | Hs00364926_m1 |

From the resulting list we selected TaqMan™ assays (Life Technologies; Grand Island, N.Y.) closest to the 3' end of each target transcript. Though the RNA tested was DNAse treated; we favored assays with probes that span exon boundaries (_m1) over those that did not (_g1, _s1) in an attempt to minimize the contribution of genomic DNA in the resulting data. There were some instances where selection of _s1 or _g1 assays was unavoidable due to the absence of available _m1 assays.

RNA Analysis and Quality Control

RNA Quality was assessed two different ways, each with their own quality metric emphasis. Concentration and A260/A280 ratio measurements were made using an appropriately blanked NanoDrop 2000 (Thermo Fisher Scientific; Waltham, Mass.). RNA Integrity Number (RIN) measurements were obtained using the Agilent 2100 Bioanalyzer (Agilent Technologies; Santa Clara, Calif.). Table 5. Prior to the study, a decision was made to exclude any RNA with RIN less than 6.0; none were excluded based on quality control criteria.

TABLE 5

| n = 106 | Average | SD | Max | Min |
| --- | --- | --- | --- | --- |
| RIN | 8.67 | 0.50 | 9.30 | 6.10 |
| Conc. [ng/µl] | 92.78 | 47.47 | 226.10 | 26.00 |
| 260/280 Ratio | 2.06 | 0.03 | 2.15 | 2.00 | cDNA Synthesis cDNA was synthesized using SuperScript VILO Master Mix (Life Technologies; Grand Island, N.Y.) in 40 µl reactions using 500 ng of RNA. The reactions were run according to the manufacturer's recommended protocol. Aliquots of RNA samples were diluted to matching concentrations prior to cDNA synthesis. This reaction generated cDNA at a final estimated concentration of 12.5 ng/µl.

Real-Time PCR

Figure 20:
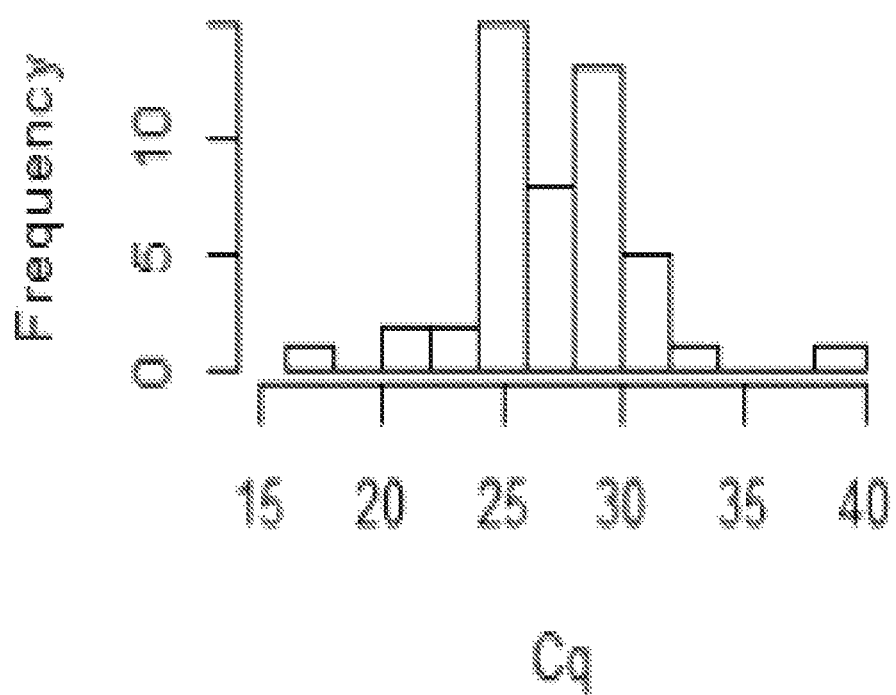
FIG. 20 shows the expression range and distribution of Cq values in 200 ng, 100 ng, 50 ng and 25 ng of cDNA for each representative sample.
Figure 20:
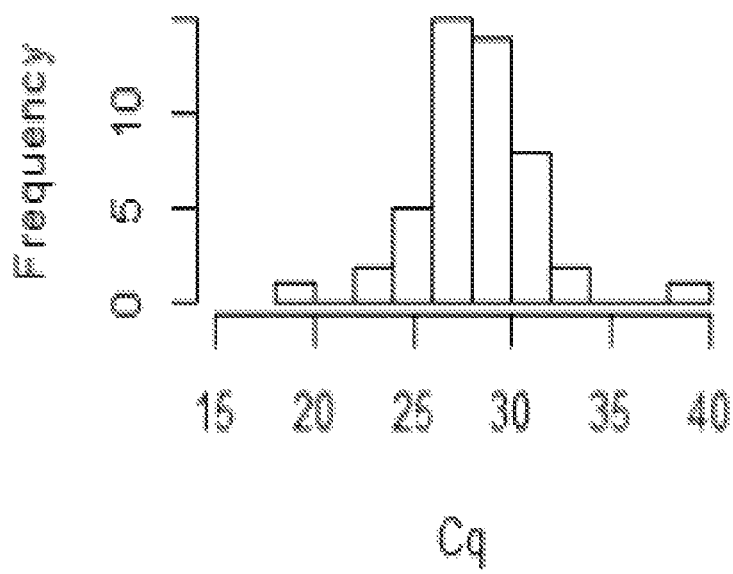
Figure 20:
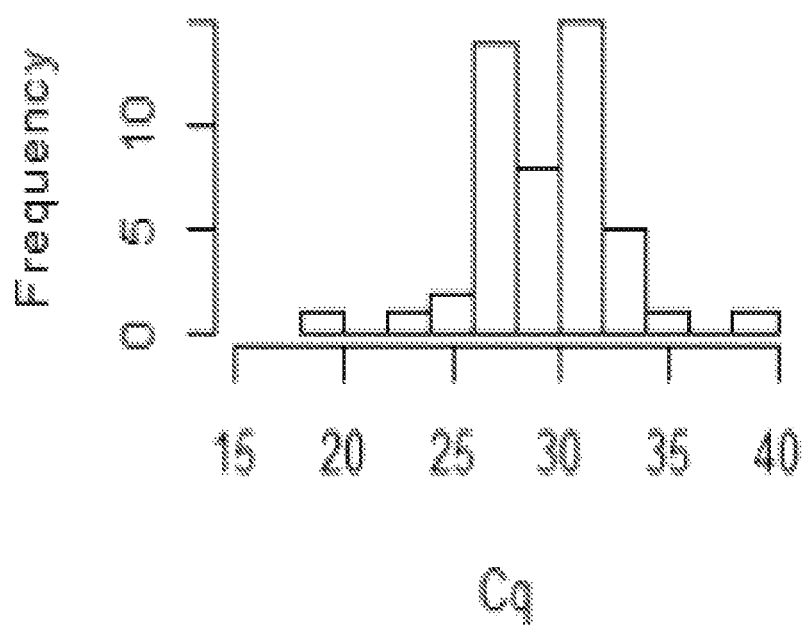
Figure 20:
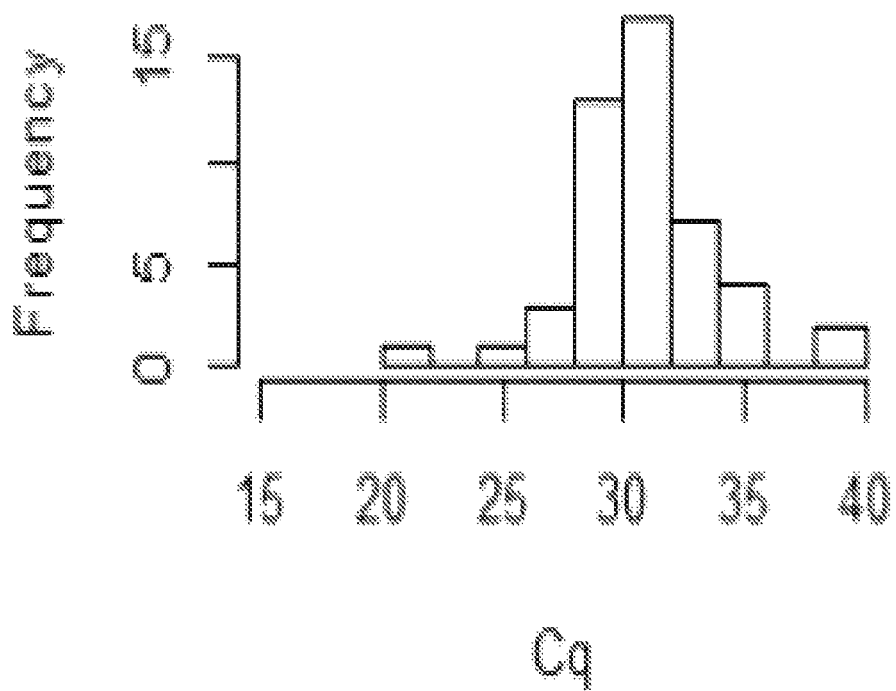

To determine the appropriate loading concentration of cDNA for the TaqMan™ Array cards (Life Technologies; Grand Island, N.Y.), a small loading test was run using cDNA from two samples; one from each group. This test was performed using conditions identical to those intended for the subsequent Real-Time PCR data collection. We examined the expression range and distribution of Cq values in 200 ng, 100 ng, 50 ng and 25 ng of cDNA for each representative sample (FIG. 20).

Final working amount of cDNA was selected to be 100 ng, based on these distributions. This was the lowest cDNA amount input that resulted in the maximum number of our transcripts crossing threshold between Cq 20 and Cq 35.

With the loading amount established, the remaining samples were assayed using RealTime PCR. Each well of the TagMan™ Array wells (Life Technologies; Grand Island, N.Y.) contained 50 µl of TagMan™ Gene Expression Master Mix (Life Technologies; Grand Island, N.Y.), 8 µl of 12.5 ng/µl cDNA, and 42 µl of RNase/DNase free Water. The Array Cards were loaded, centrifuged and sealed according to the manufacturer's specifications. These sealed plates were assayed using the ViiA7 Real-Time Detection System (Life Technologies; Grand Island, N.Y.) using a TagMan™ Array Card thermal block (Life Technologies; Grand Island, N.Y.) and FAM dye detection. The thermal cycling parameters were as shown in Table 6.

TABLE 6

| | Temp ° C. | Time (m) |
| --- | --- | --- |
| Step 1 | 50 | 2 |
| Step 2 | 95 | 10 |
| Cycle (40x) | 95 | 0:15 |
| | 60 | 1 |

All reactions used in downstream analysis passed quality control checks for proper exponential phase amplification and passed automatic threshold/baseline detection checks established by the ViiA7 Real-Time PCR software. Amplification curves were also inspected visually for abnormalities. All Cq values were less than 35.

PCR efficiencies for these TaqMan™ assays (Life Technologies; Grand Island, N.Y.) were previously determined to be near 100% based on Life Technologies quality control metric and in house testing. Per the testing of their internal labs and others, the ΔΔCq analysis method assuming 100% efficiency was determined to be more appropriate for the analysis of this data than methods incorporating efficiency correction (Livak et al. (2001) Methods 25:402-408). Had these assays been built in house and not previously tested for similar efficiency; efficiency calculation and correction would have been a necessity.

GeNorm Analysis of Potential Reference Assays

Potential reference targets were chosen based on previous GeNorm analysis of a panel of reference transcripts in PAXgene® (Qiagen; Valencia, Calif.) whole blood derived RNA (Stamova et al. (2009) BMC medical genomics 2:49). The GeNorm panel was partially replicated using PAXgene® (Qiagen; Valencia, Calif.) samples collected locally and was performed using the reagents intended for downstream use in our TaqMan™ Array (Life Technologies; Grand Island, N.Y.) PCR work. The results were highly congruent. Three of the most stable transcripts [PPIB, TRAP1, GAPDH] were chosen for inclusion on our TaqMan™ array (Life Technologies; Grand Island, N.Y.) along with ACTB.

Prior to analysis of the study data, the GeNorm selection process was repeated with the four included reference assays across all study samples. The M scores were as shown in Table 7.

TABLE 7

| Assay | Transcript | M |
|---|---|---|
| Hs99999903_m1 | ACTB | 0.54 |
| Hs00168719_m1 | PPIB | 0.46 |
| Hs00212474_m1 | TRAP1 | 0.42 |
| Hs99999905_m1 | GAPDH | 0.42 |

The geometric mean of all reference transcripts with M-scores of less than 0.5 was used as the representative reference assay for all subsequent normalizations (Bustin et al., Clinical Chemistry (2009) 55:611-622).

Real-Time Statminer Analysis

Data exported form the ViiA7 as formatted for import into Real-Time Statminer Analysis software (Integromics; Madison, Wis.). This software provided a pipeline for rapid analysis of the total set of Real-Time PCR data generated in this study. Data were normalized based on the geometric mean of the most stable set of reference targets as determined by the GeNorm stability analysis algorithm in Statminer. This normalization was used to generate tables of Cq and ΔCq for subsequent analysis.

Platelet purification, Protein Sample Preparation, and Proteomics Analysis by LC-MS/MS.

Platelets were purified from 40 cc of whole blood from HV2 subjects according to a previously described protocol (Schedel et al., Methods Mol Biol (2009) 496:273-283; Rox et al., Methods Mol Biol (2009) 496:285-292) at the same time as whole blood RNA collection. Briefly, this protocol filters PRP through a high-efficiency leukocyte reduction filter (PL1B, Pall Medical). This method achieves $10^3$ reduction in CD45 RNA (9), absence of platelets by cell-counter or by flow cytometry using CD45 specific antibodies (>99.9% platelet purity). Platelets were subsequently pelleted at 1500×g for 10 minutes, lysed with 800 µl Denaturing Solution (Ambion, Catalog # AM8540G) and followed by organic extraction with 800 µl Acid-Phenol:Chloroform. The organic phase and interphase suspension was carried forward for protein extraction.

To 0.5 mL of platelet lysate, 1.0 mL of ice cold methanol was added in a 1.5 mL Eppendorf tube to precipitate the protein. The sample was vortexed briefly, stored at 30° C. while gently shaking for 10 minutes, then cooled on ice and protein was subsequently sedimented by centrifuging at 12,000 rcf for 10 minutes at 4° C. Supernatant was removed and the remaining pellet was washed with 1.0 mL of ice cold MeOH and spun again at 12,000 rcf for 2 minutes. Supernatant was removed and another 1.0 mL of ice cold MeOH was added followed by burst sonication of the protein pellet to generate a fine protein powder suspension. Protein was settled by centrifuging at low speed of 2,000 rcf for 1 minute. Supernatant was removed and excess MeOH was allowed to evaporate from the protein pellet while carefully avoiding taking the pellet to dryness. 0.4 mL of 0.5% w/v Rapigest surfactant (Waters Corporation) in 50 mM ammonium bicarbonate was added to solubilize the protein followed by vortexing briefly, and heating at 60° C. for 45 minutes. 25% by volume was pipetted out and diluted 10× with 0.25% w/v Rapigest to approximately 1 mg/mL. Pre-digestion concentration was measured by total protein assay (mini Bradford, Bio-Rad, Inc), and total protein recovery was >3.5 mg. Samples were stored at −80 Celsius until LC-MS analysis.

Purified platelet protein lysates were sonicated using a Qsonica sonicator (Newton, Conn.) to disrupt the cell membranes. Total protein content was measured using a Thermo Scientific Micro BCA Protein Assay kit (ThermoFisher Scientific) using the manufacturer's instructions. For each sample, a sample volume corresponding to 35 µg of protein was normalized to a total volume of 110 µL with 50 mM ammonium bicarbonate. This was reduced with 10 mM DTT for 15 min at 70° C., and free sulfhydryls were alkylated with 20 mM iodoacetamide for 30 min at room temperature. Proteolytic digestion was accomplished by the addition of 700 ng of sequencing grade trypsin (Promega) and incubation at 37° C. for 18 hours. Samples were then acidified to pH2.5 with a mixture of 10% trifluoroacetic acid (TFA)/20% acetonitrile/70% water and incubated at 60° C. for 2 hours to hydrolyze remaining RapiGest surfactant. Insoluble hydrolyzed surfactant was cleared by centrifugation at 15,000 rpm for 5 min. The mobile phase consisted of (A) 0.1% formic acid in water and (B) 0.1% formic acid in acetonitrile. After a 2-µl injection (1 µg of total protein), peptides were trapped for 15 min on a 5-mm Symmetry C18 trap column (180 mm ID×20 mm) at 5 µl/min in 99% A. Chromatographic separation of the peptides was made with a Waters nanoACQUITY UPLC equipped with a 1.7-mm BEH130 C18 reversed-phase column [75 µm inside diameter (ID)×250 mm]. After loading the sample, the analytical column was then switched inline and a linear elution gradient of 5% B to 40% B was performed over 120 min at 400 nl/min. Chromatographic separation of peptide mixtures was performed. The analytical column was connected to a fused silica PicoTip emitter (New Objective) with a 10-mm tip orifice and coupled to the mass spectrometer through a nano-electrospray interface. MS data were acquired on an LTQ Orbitrap XL (Thermo Scientific). The instrument was set to acquire a precursor MS scan in the Orbitrap from mass/charge ratio (m/z) 375 to 2000 with r=60,000 at m/z 400 and a target AGC setting of 5×105 ions. In a data-dependent mode of acquisition, MS/MS spectra of the five most abundant precursor ions were acquired in the Orbitrap at r=7500 at m/z 400 with a target AGC setting of 3×104 ions. Maximum fill times were set to 500 ms for full MS scans and 50 ms for MS/MS scans with a minimum MS/MS triggering thresholds of 5000 counts. For all experiments, fragmentation occurred in the LTQ linear ion trap with a collision-induced dissociation (CID) energy setting of 35% and a dynamic exclusion of 30 s was used for previously fragmented precursor ions.

The MS data were processed in Elucidator (Rosetta Biosoftware) to align the chromatograms and identify features in the samples. A search using MASCOT (Matrix Sciences) with a Uniprot database (human database appended with yeast alcohol dehydrogenase (ADH), Jul. 15, 2012) was performed on each of the samples. The aligned mass features were annotated with the database search results using a predicted false discovery rate of 1%.

Statistical Analysis.

The raw and normalized microarray data are available in the Gene Expression Omnibus for the OPC cohort (GSE38511). The data for the HV1, HV2, and CATHGEN cohorts is available through the database of Genotypes and Phenotypes (phs000548.v1.p1 and phs000551.v1.p1). Unless stated otherwise, all tests were two-sided and were performed in R (2.10.0) or Matlab (R2010b); a p-value of <0.05 was considered significant.

Discovery of Coexpressed Gene Sets Associated with PFS—Factor Modeling.

The HV1, post-aspirin RMA normalized data were non-specifically filtered (i.e., without regard to PFS) to remove probes with mean expression less than 2.0 (i.e., the gene was not expressed in whole blood) or with variance less than 0.25 (i.e., the gene was homogenously expressed), resulting in 2,929 probe sets for subsequent analysis. To discover "Factors" or sets of coexpressed genes representative of biological pathways, Bayesian factor regression modeling was used (BFRM; Wang et al., Bulletin of the International Society of Bayesian Analysis (2007) 14:4-5; Carvalho et al., Journal of the American Statistical Association (2008) 103: 1438-1456)(in an unsupervised fashion (i.e., without regard to PFS). Each of the probe sets used to estimate a particular Factor can be interpreted as a measurement of the activity of some (potentially unknown) biological pathway. Each sample can then be assigned a "Factor score", which represents the aggregate expression of the transcripts within a Factor. The Factor scores can then be used for association with the phenotype of interest in subsequent analyses.

Factor Projection, Gene Membership within a Factor, Comparison of Factor Gene Lists with Selected Gene Sets, and Co-Expression of Transcripts Represented by a Factor Before and after Aspirin Exposure.

To measure Factor scores in the remaining datasets, the factor model derived in the HV1 post-aspirin dataset was projected onto the microarray data from the remaining cohorts. The projected Factor scores were then used in downstream analyses (Lucas et al., PLoS Computational Biology (2010) 6:e1000920)).

To identify probe sets belonging to a particular Factor, the BFRM algorithm also generates a matrix of posterior means for inclusion probabilities ($\pi$) for each probe set, which provides a probability that a given probe set is a member of a given Factor. Using these probabilities, we assigned a given probe set as a member of a Factor if the if $\pi > 0.99$.

Correlations Between Factor Scores and Platelet Function.

Pearson correlation was used to test for association between a Factor and PFS in HV1 and HV2. In the second validation cohort, OPC, a one-sided t-test was chosen as it was hypothesized that a lower factor score in the aspirin-resistant vs. aspirin-sensitive groups. Linear regression was used to assess the independent association of Factor scores and PFS after accounting for log-transformed MPV and/or platelet count.

Correction for Multiple Hypotheses Testing.

As HV1 was a hypothesis-generating pilot study p-values were not adjusted. In the first validation cohort, HV2, the p-values were adjusted using Bonferonni correction. In the second validation cohort, only one hypothesis test was performed.

Analyses of RT-PCR Data.

The expression of each selected transcript relative to the three reference genes was expressed as $\Delta$ Cq (or "deltaCq") and correlated with the corresponding microarray probe set or platelet function score using Pearson tests of correlation.

Co-Expression of Transcripts Represented by a Factor Before and after Aspirin Exposure For the HV1 post-aspirin exposure dataset the first principle component of a given set of probe sets within a Factor was computed. The samples (columns) were then reordered to make the first principal component increasing and the probe sets (rows) were reordered from highest to lowest correlation with the first principal component. To determine if a similar pattern of co-expression existed in the pre-aspirin dataset, the row ordering determined above was applied to the pre-aspirin HV1 data and the columns were reordered as above. A heatmap was used to visualize the two resulting, reordered datasets.

Comparison of Factor Gene Lists with Selected Gene Sets

To infer the cell type(s) contributing to a Factor, we used publically available data to generate gene lists specific to platelets, megakaryocytes, and other non-platelet blood cell types and two complementary methods: 1) comparison of the proportion of genes in a Factor also in a gene set of interest using a Fischer's exact test and 2) enrichment of selected gene sets in the Factor score using Gene Set Enrichment Analysis (GSEA) (Wang et al., Bulletin of the International Society of Bayesian Analysis (2007) 14:4-5). For the latter we combined the HV1 and HV2 microarray datasets and converted each probe set into a gene symbol. The median expression of the representative Affymetrix probes for each gene was selected and a Pearson correlation with the factor score of interest generated a ranked list after 1000 permutations.

Platelet Proteomic Dataset Analysis.

Data sets were aligned with a previously described approach (Lucas et al., BMC Bioinformatics (2012) 13:74). After alignment, all peptides from a list of known plasma proteins were excluded (Table 8). Intensities from the remaining ~28,000 peptides were scaled and log transformed so that average log-transformed intensity from each sample was equal. Analyses were performed on the ~130 peptides identified as originating from proteins from a given Factor (Table 8). Relative protein expression was computed as the first principal component of all peptides from that protein. P-values reported are from Pearson tests of correlation with PFS.

TABLE 8

| Plasma proteins excluded from analysis | | Factor 14 proteins included in analysis | |
|---|---|---|---|
| Protein Name | Gene Name | Protein Name | Gene Name |
| ALBU_HUMAN | ALB | A3KPC7_HUMAN | HIST1H2AG |
| APOA1_HUMAN | APOA1 | A3KPC7_HUMAN | HIST1H2AI |
| APOA2_HUMAN | APOA2 | A3KPC7_HUMAN | HIST1H2AH |
| APOA4_HUMAN | APOA4 | A3KPC7_HUMAN | HIST1H2AK |
| APOB_HUMAN | APOB | A3KPC7_HUMAN | HIST1H2AM |
| APOC3_HUMAN | APOC3 | A3KPC7_HUMAN | HIST1H2AL |
| APOE_HUMAN | APOE | A4FTV9_HUMAN | HIST1H2AG |
| APOE_HUMAN | LOC100129500 | A4FTV9_HUMAN | HIST1H2AI |
| APOH_HUMAN | APOH | A4FTV9_HUMAN | HIST1H2AH |
| IGHA1_HUMAN | IGHA1 | A4FTV9_HUMAN | HIST1H2AK |
| IGHA2_HUMAN | IGHA2 | A4FTV9_HUMAN | HIST1H2AM |
| IGHG1_HUMAN | IGHV3-11 | A4FTV9_HUMAN | HIST1H2AL |
| IGHG1_HUMAN | IGHV3-7 | A8K0X1_HUMAN | CALD1 |
| IGHG1_HUMAN | IGHG3 | A8K5V0_HUMAN | PBX1 |
| IGHG1_HUMAN | IGHG1 | A8MQ20_HUMAN | CDC14B |
| IGHG1_HUMAN | IGHG1 | B0QYN1_HUMAN | PARVB |
| IGHG1_HUMAN | IGHM | B2R4S9_HUMAN | HIST1H2BC |
| IGHG1_HUMAN | IGHV4-31 | B2R4S9_HUMAN | HIST1H2BE |
| IGHG2_HUMAN | IGHG2 | B2R4S9_HUMAN | HIST1H2BF |
| IGHG3_HUMAN | IGHV3-11 | B2R4S9_HUMAN | HIST1H2BI |
| IGHG3_HUMAN | IGHV3-7 | B2R4S9_HUMAN | HIST1H2BG |
| IGHG3_HUMAN | IGHG3 | B2R5B3_HUMAN | HIST1H2AG |
| IGHG3_HUMAN | IGHG1 | B2R5B3_HUMAN | HIST1H2AI |
| IGHG3_HUMAN | IGH3 | B2R5B3_HUMAN | HIST1H2AH |
| IGHG3_HUMAN | IGHM | B2R5B3_HUMAN | HIST1H2AK |
| IGHG3_HUMAN | IGHV4-31 | B2R5B3_HUMAN | HIST1H2AM |
| IGHG4_HUMAN | IGHG4 | B2R5B3_HUMAN | HIST1H2AL |
| IGHM_HUMAN | IGHV3-11 | B3KRC2_HUMAN | MGLL |
| IGHM_HUMAN | IGHV3-7 | B3KXX8_HUMAN | BEND2 |
| IGHM_HUMAN | IGHG3 | B3KY43_HUMAN | PRKAR2B |
| IGHM_HUMAN | IGHG1 | B4DUC0_HUMAN | TMEM64 |
| IGHM_HUMAN | IGHM | BEND2_HUMAN | BEND2 |
| IGHM_HUMAN | IGHM | CALD1_HUMAN | CALD1 |
| IGHM_HUMAN | IGHV4-31 | CC14B_HUMAN | CDC14B |
| IGJ_HUMAN | IGJ | CC90A_HUMAN | CCDC90A |
| IGKC_HUMAN | IGKC | CKLF5_HUMAN | CMTM5 |
| IGKC_HUMAN | LOC652493 | CLC1B_HUMAN | CLEC1B |
| IGKC_HUMAN | LOC650405 | CLC4D_HUMAN | CLEC4D |
| IGKC_HUMAN | LOC100130100 | CLUS_HUMAN | CLU |
| ITIH1_HUMAN | ITIH1 | CPNE5_HUMAN | CPNE5 |
| ITIH2_HUMAN | ITIH2 | CTDSL_HUMAN | CTDSPL |
| ITIH4_HUMAN | ITIH4 | CXCL5_HUMAN | CXCL5 |
| KV309_HUMAN | IGKV3D-11 | CXCL7_HUMAN | PPBP |
| KV312_HUMAN | IGKV3-20 | ELOV7_HUMAN | ELOVL7 |
| | | ENDD1_HUMAN | ENDOD1 |
| | | FRMD3_HUMAN | FRMD3 |
| | | FSTL1_HUMAN | FSTL1 |
| | | GBG11_HUMAN | GNG11 |
| | | GCYB1_HUMAN | GUCY1B3 |
| | | GP1BB_HUMAN | GP1BB |
| | | H2A1_HUMAN | HIST1H2AG |
| | | H2A1_HUMAN | HIST1H2AI |
| | | H2A1_HUMAN | HIST1H2AH |
| | | H2A1_HUMAN | HIST1H2AK |
| | | H2A1_HUMAN | HIST1H2AM |
| | | H2A1_HUMAN | HIST1H2AL |
| | | H2A1D_HUMAN | HIST2H3A |
| | | H2A1D_HUMAN | HIST1H3J |
| | | H2A1D_HUMAN | HIST1H2AD |
| | | H2A1D_HUMAN | HIST1H3G |
| | | H2A1D_HUMAN | HIST1H3I |
| | | H2A1D_HUMAN | HIST2H3C |
| | | H2A1D_HUMAN | HIST2H3D |
| | | H2A1D_HUMAN | HIST1H3A |
| | | H2A1D_HUMAN | HIST1H3B |
| | | H2A1D_HUMAN | HIST1H3C |
| | | H2A1D_HUMAN | HIST1H3D |
| | | H2A1D_HUMAN | HIST1H3E |
| | | H2A1D_HUMAN | HIST1H3F |
| | | H2A1D_HUMAN | HIST1H3H |
| | | H2A1H_HUMAN | HIST1H2AG |
| | | H2A1H_HUMAN | HIST1H2AI |
| | | H2A1H_HUMAN | HIST1H2AH |
| | | H2A1H_HUMAN | HIST1H2AK |
| | | H2A1H_HUMAN | HIST1H2AM |
| | | H2A1H_HUMAN | HIST1H2AL |

TABLE 8-continued

| Plasma proteins excluded from analysis | | Factor 14 proteins included in analysis | |
|---|---|---|---|
| Protein Name | Gene Name | Protein Name | Gene Name |
| | | H2A1J_HUMAN | HIST1H2AJ |
| | | H2A1J_HUMAN | HIST1H2AG |
| | | H2A1J_HUMAN | HIST1H2AI |
| | | H2A1J_HUMAN | HIST1H2AH |
| | | H2A1J_HUMAN | HIST1H2AK |
| | | H2A1J_HUMAN | HIST1H2AM |
| | | H2A1J_HUMAN | HIST1H2AL |
| | | H2B1C_HUMAN | HIST1H2BC |
| | | H2B1C_HUMAN | HIST1H2BE |
| | | H2B1C_HUMAN | HIST1H2BF |
| | | H2B1C_HUMAN | HIST1H2BI |
| | | H2B1C_HUMAN | HIST1H2BG |
| | | H31_HUMAN | HIST2H3A |
| | | H31_HUMAN | HIST1H3J |
| | | H31_HUMAN | HIST1H2AD |
| | | H31_HUMAN | HIST1H3G |
| | | H31_HUMAN | HIST1H3I |
| | | H31_HUMAN | HIST2H3C |
| | | H31_HUMAN | HIST2H3D |
| | | H31_HUMAN | HIST1H3A |
| | | H31_HUMAN | HIST1H3B |
| | | H31_HUMAN | HIST1H3C |
| | | H31_HUMAN | HIST1H3D |
| | | H31_HUMAN | HIST1H3E |
| | | H31_HUMAN | HIST1H3F |
| | | H31_HUMAN | HIST1H3H |
| | | H32_HUMAN | HIST2H3A |
| | | H32_HUMAN | HIST1H3J |
| | | H32_HUMAN | HIST1H2AD |
| | | H32_HUMAN | HIST1H3G |
| | | H32_HUMAN | HIST1H3I |
| | | H32_HUMAN | HIST2H3C |
| | | H32_HUMAN | HIST2H3D |
| | | H32_HUMAN | HIST1H3A |
| | | H32_HUMAN | HIST1H3B |
| | | H32_HUMAN | HIST1H3C |
| | | H32_HUMAN | HIST1H3D |
| | | H32_HUMAN | HIST1H3E |
| | | H32_HUMAN | HIST1H3F |
| | | H32_HUMAN | HIST1H3H |
| | | IF2B3_HUMAN | IGF2BP3 |
| | | ITA2B_HUMAN | ITGA2B |
| | | ITB3_HUMAN | ITGB3 |
| | | JAM3_HUMAN | JAM3 |
| | | KAP3_HUMAN | PRKAR2B |
| | | LEGL_HUMAN | HSPC159 |
| | | LOX12_HUMAN | ALOX12 |
| | | LRC32_HUMAN | LRRC32 |
| | | LYAM3_HUMAN | SELP |
| | | MFA3L_HUMAN | MFAP3L |
| | | MGLL_HUMAN | MGLL |
| | | MYL9_HUMAN | MYL9 |
| | | MYLK_HUMAN | MYLK |
| | | NCKX3_HUMAN | SLC24A3 |
| | | O15513_HUMAN | TPM1 |
| | | PAQRB_HUMAN | MMD |
| | | PARVB_HUMAN | PARVB |
| | | PBX1_HUMAN | PBX1 |
| | | PCGF5_HUMAN | PCGF5 |
| | | PCSK6_HUMAN | PCSK6 |
| | | PDE5A_HUMAN | PDE5A |
| | | PF4V_HUMAN | PF4V1 |
| | | PLF4_HUMAN | PF4 |
| | | PROS_HUMAN | PROS1 |
| | | Q05B97_HUMAN | MYLK |
| | | Q05B98_HUMAN | MYLK |
| | | Q05D81_HUMAN | MYLK |
| | | Q05DR4_HUMAN | CALD1 |
| | | Q06F34_HUMAN | PROS1 |
| | | Q06F35_HUMAN | PROS1 |
| | | Q06S79_HUMAN | MYLK |
| | | Q07413_HUMAN | TPM1 |
| | | Q07414_HUMAN | TPM1 |
| | | Q0MVN7_HUMAN | ITGA2B |
| | | Q15657_HUMAN | TPM1 |
| | | Q16120_HUMAN | ALOX12 |

TABLE 8-continued

| Plasma proteins excluded from analysis | | Factor 14 proteins included in analysis | |
|---|---|---|---|
| Protein Name | Gene Name | Protein Name | Gene Name |
| | | Q16157_HUMAN | ITGB3 |
| | | Q16441_HUMAN | PROS1 |
| | | Q16519_HUMAN | PROS1 |
| | | Q1PBM2_HUMAN | ITGB3 |
| | | Q1W146_HUMAN | PROS1 |
| | | Q1W147_HUMAN | PROS1 |
| | | Q1W148_HUMAN | PROS1 |
| | | Q1ZYL5_HUMAN | TPM1 |
| | | Q2VYF8_HUMAN | MGLL |
| | | Q2YFE1_HUMAN | ITGB3 |
| | | Q308M1_HUMAN | MPL |
| | | Q3B765_HUMAN | MYLK |
| | | Q4V9S2_HUMAN | BEND2 |
| | | Q4W5L4_HUMAN | PDE5A |
| | | Q4W5N7_HUMAN | MFAP3L |
| | | Q53HG7_HUMAN | CTTN |
| | | Q53Y01_HUMAN | GNG11 |
| | | Q567T3_HUMAN | RHOBTB1 |
| | | Q59E99_HUMAN | THBS1 |
| | | Q59FA8_HUMAN | ITGA2B |
| | | Q59GR8_HUMAN | TPM1 |
| | | Q59H04_HUMAN | PCSK6 |
| | | Q59HG6_HUMAN | ARHGAP6 |
| | | Q5HY93_HUMAN | CALD1 |
| | | Q5JU06_HUMAN | CDC14B |
| | | Q5JUY5_HUMAN | MPL |
| | | Q5PY48_HUMAN | CMTM5 |
| | | Q5R349_HUMAN | SELP |
| | | Q658T3_HUMAN | CPNE5 |
| | | Q68DD6_HUMAN | PBX1 |
| | | Q68DK3_HUMAN | MYLK |
| | | Q6DHZ2_HUMAN | PRKAR2B |
| | | Q6I9S7_HUMAN | CXCL5 |
| | | Q6IBG1_HUMAN | MYL9 |
| | | Q6IBG9_HUMAN | MGLL |
| | | Q6J1N0_HUMAN | PROS1 |
| | | Q6LAL4_HUMAN | MYLK |
| | | Q6LDK5_HUMAN | ITGA2B |
| | | Q6LDQ3_HUMAN | CLU |
| | | Q6NUL9_HUMAN | SELP |
| | | Q6P2N0_HUMAN | MYLK |
| | | Q6P707_HUMAN | CALD1 |
| | | Q6PIF1_HUMAN | TTC7B |
| | | Q6PJM5_HUMAN | CALD1 |
| | | Q6QE20_HUMAN | SPARC |
| | | Q6ULR6_HUMAN | SELP |
| | | Q6ZN40_HUMAN | TPM1 |
| | | Q6ZNP1_HUMAN | MYLK |
| | | Q6ZP76_HUMAN | TPM1 |
| | | Q71U02_HUMAN | MYL9 |
| | | Q75MP1_HUMAN | PRKAR2B |
| | | Q76MU0_HUMAN | CTTN |
| | | Q7KYY3_HUMAN | THBS1 |

Example 4

Analyses of CATHGEN Cohorts

Logistic or Cox proportional hazards regression models were created in the case:control or observational cohorts, respectively, to test for association between the Factor and death/MI. Each model tested the Factor alone as well as after controlling for baseline variables (Table 9) associated with the Factor of interest. The assumption of proportional hazards for each Cox model was met. Odds (or hazards) ratios, 95% confidence intervals, and p-values are reported.

TABLE 9

Baseline characteristics in CATHGEN cohorts and their association with Factor 14 levels

| Variable | Case:Control Cohort (n = 397) | Observational cohort (n = 190) | P-value for association with Factor 14* |
|---|---|---|---|
| Age (years; median, [IQR]) | 65 [57-73] | 56 [47-67] | 0.15 |
| Hypertension (%) | 70.3% | 70.5% | 0.23 |
| CAD | 26% | 78% | 0.47 |
| Diabetes (%) | 34.3% | 23.2% | 0.14 |

TABLE 9-continued

Baseline characteristics in CATHGEN cohorts and their association with Factor 14 levels

| Variable | Case:Control Cohort (n = 397) | Observational cohort (n = 190) | P-value for association with Factor 14* |
|---|---|---|---|
| RACE (%) | | | |
| White | 74.3% | 66.8% | Reference |
| African-American | 21.7% | 26.8% | 2.13e−06 |
| Other | 4.0% | 6.3% | 0.53 |
| Female (%) | 32.2% | 41.1% | 7.37e−06 |
| Smoking history (%) | 47.9% | 53.7% | 0.06 |
| Hyperlipidemia (%) | 61.0% | 61.6% | 0.37 |

*The combined Case:Control and Observational cohorts were used to test for associations with Factor 14 levels, while controlling for cohort using linear regression.

To assess the independent association between the Factor and death/MI, logistic regression models were built on the combined CATHGEN cohorts by forcing Framingham risk factors (age, sex, smoking, diabetes, hypertension, hyperlipidemia), African-American [AA] race, cohort, platelet count, and the presence of CAD (defined as a CAD index (Mark et al., (1994) Circulation 89:2015-2025)>32 or history of coronary artery bypass surgery/MI/percutaneous coronary intervention), into the model and adding the Factor score or individual probe set gene expression. To assess the incremental prognostic value of gene expression, the performance of competing models (risk factors±Factor/probe set expression) was compared using the areas under the receiver operating characteristics curve (ROC), the net reclassification index (NRI, using risk categories of <10%, 10-20%, or >20% or category-free NRI, and the integrated discrimination improvement [IDI]) (Table 10).

TABLE 10

Net Reclassification Table for combined CATHGEN cohorts

| | 10% | 10-20% | >20% | % Reclassified |
|---|---|---|---|---|
| Factor 14 (ARS) | | | | |
| 10% | 10 | 4 | 0 | 29 |
| 10-20% | 4 | 55 | 6 | 15 |
| >20% | 0 | 14 | 474 | 3 |
| Net Reclassification Index | | | | 4.6% (p = 0 007) |
| ITGA2B | | | | |
| 10% | 8 | 5 | 1 | 43 |
| 10-20% | 13 | 42 | 10 | 35 |
| >20% | 1 | 24 | 463 | 5 |
| Net Reclassification Index | | | | 7.5% (p = 0.002) |

Example 5

Discovery and Validation of a Set of Co-Expressed Genes in Whole Blood that Correlate with Platelet Function on Aspirin In the discovery cohort (HV1) 20 Factors (numbered 1-20, Table 11) were identified representing sets of highly correlated, co-expressed genes.

TABLE 11

Factors identified using Bayesian factor regression modeling of peripheral blood gene expression data and their characteristics

| Factor Number | Number of genes within Factor | GO terms | KEGG terms |
|---|---|---|---|
| 1 | 521 | protein modification, cellular physiological process, protein transport, establishment of protein localization, protein localization organismal physiological process ubiquitin cycle, G-protein coupled receptor protein signaling pathway neurophysiological process, cell surface receptor linked signal transduction, protein metabolism intracellular protein transport, response to external stimulus, cellular protein metabolism, intracellular transport, cellular macromolecule metabolism, macromolecule metabolism, response to stimulus | NS |
| 2 | 142 | cellular physiological process | NS |
| 3 | 16 | NS | NS |
| 4 | 58 | protein biosynthesis, macromolecule biosynthesis, cellular biosynthesis biosynthesis, cellular protein metabolism, protein metabolism macromolecule metabolism, cellular macromolecule metabolism | oxidative phosphorylation |
| 5 | 29 | response to biotic stimulus, immune response, defense response, deoxyribonucleotide metabolism | NS |
| 6 | 91 | response to biotic stimulus, immune response, defense response, response to stimulus, organismal physiological process, progesterone metabolism | NS |
| 7 | 120 | NS | NS |
| 8 | 291 | immune response, response to external biotic stimulus, response to pest, pathogen or parasite, response to biotic stimulus, defense response, inflammatory response, response to wounding | NS |
| 9 | 153 | NS | NS |
| 10 | 68 | NS | NS |
| 11 | 11 | NS | NS |

TABLE 11-continued

Factors identified using Bayesian factor regression modeling of peripheral blood gene expression data and their characteristics

| Factor Number | Number of genes within Factor | GO terms | KEGG terms |
|---|---|---|---|
| 12 | 248 | cellular physiological process | NS |
| 13 | 53 | gas transport, oxygen transport | NS |
| 14 | 62 | blood coagulation, coagulation hemostasis, regulation of body fluids, platelet activation | NS |
| 15 | 99 | NS | NS |
| 16 | 32 | response to biotic stimulus | Nicotinate and nicotinamide metabolism |
| 17 | 115 | NS | NS |
| 18 | 49 | NS | NS |
| 19 | 52 | NS | S |
| 20 | 73 | NS | S |

GO = Gene Ontology;
KEGG = Kyoto Encyclopedia of Genes and Genomes;
NS = no significantly associated terms/pathways (see Methods for significance level)

Figure 8:
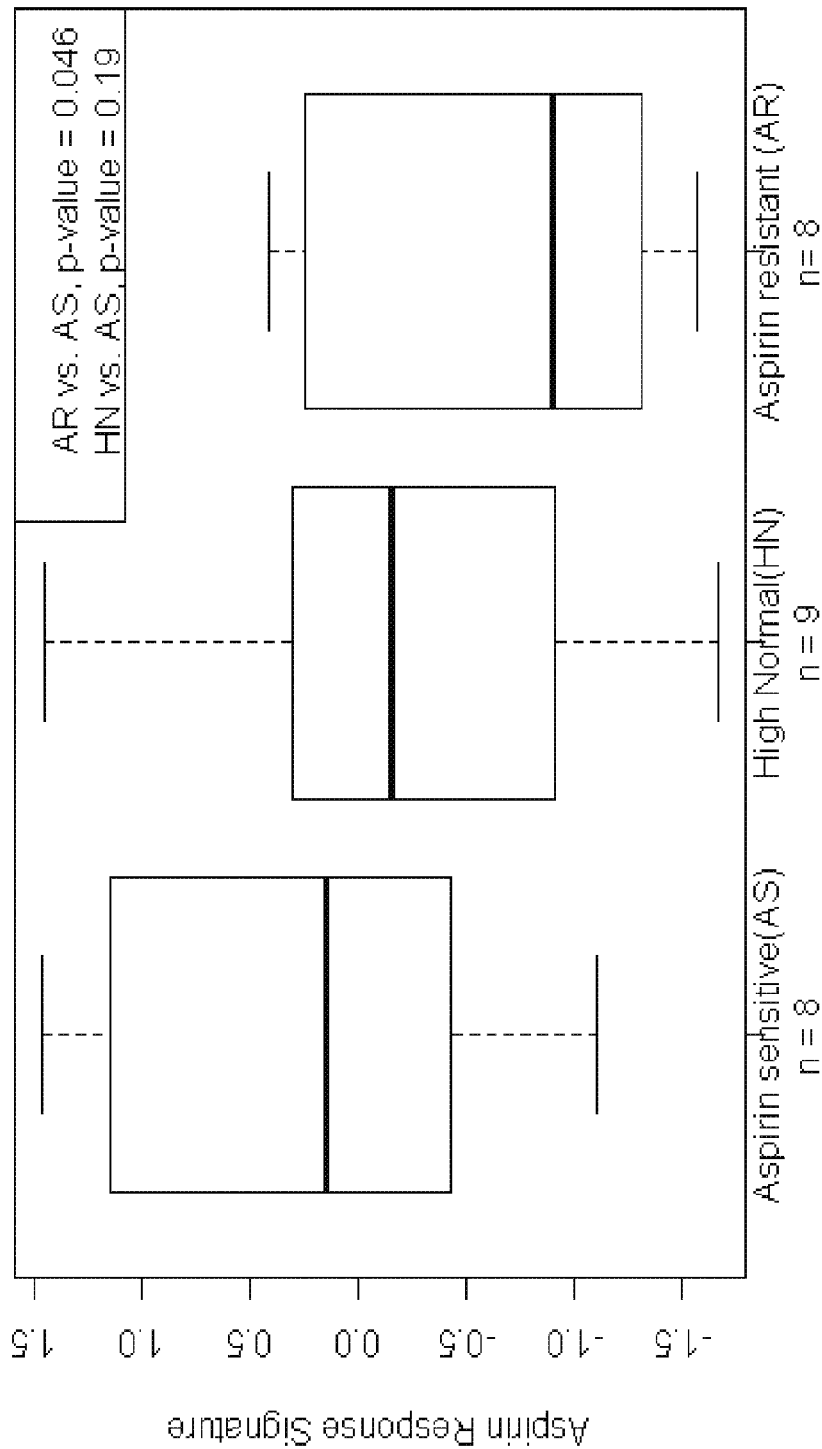
FIG. 8 shows that ARS was associated with platelet function in patients at risk for cardiovascular disease. Patients treated with 81 mg/day aspirin were assessed with the VerifyNow Aspirin device. Three categories of individuals were profiled by microarray based on their aspirin response units (ARU): Aspirin resistant (AR, ARU>550); High normal (HN, 500<ARU<550); Aspirin sensitive (AS, ARU<550). ARS values are for each group are plotted and compared using two-sample t-tests. P-values are one-sided.

To test the hypothesis that one or more of these gene sets were associated with PFS on aspirin, each set was correlated with PFS in HV1 and identified "Factor 14" (FIG. 7A) and "Factor 3" (r=0.27, p-value=0.05). In the first validation cohort (HV2), a significant association was found between Factor 14 and PFS, with the same strength and direction as observed in HV1 (FIG. 7B, Bonferroni adjusted p-value=0.03), thus validating this association, however Factor 3 was not associated with PFS in HV2. Factor 14 was further validated with VerifyNow test results in the OPC cohort (FIG. 8). Thus Factor 14, which was named the "aspirin response signature" (ARS), was validated in two independent cohorts as a set of co-expressed genes associated with platelet function on aspirin.

Figure 9:
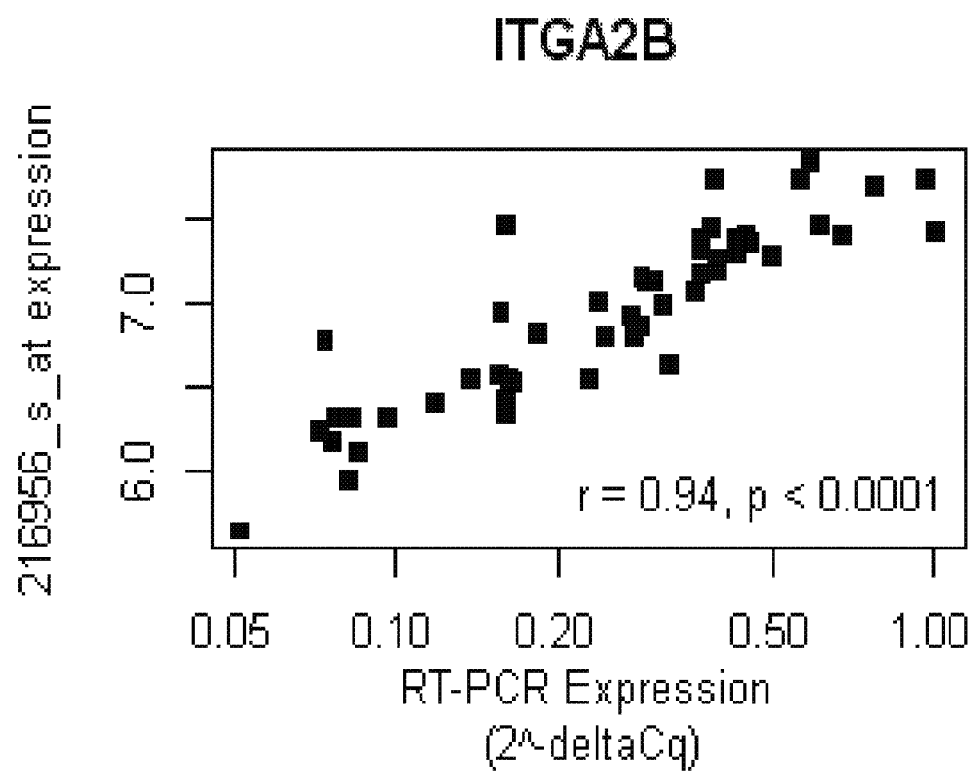
FIG. 9 shows that PCR-based assays verified the microarray-based gene expression values for ARS genes. Real-time PCR assays were designed to verify selected transcripts represented by the ARS in the HV2 cohort. The deltaCq for each assay was correlated with the RMA normalized, probe set expression for the corresponding ARS gene using Pearson correlation (see Table 12). For the four genes with the highest PCR vs. microarray-based correlation (ITGA2B, MYL9, TREML1, and MPL), the relative quantity ($2^{-delt\_aCq}$, x-axis, log-scale) vs. the corresponding probe set expression (y-axis), correlation coefficient, and p-value were plotted.
Figure 9:
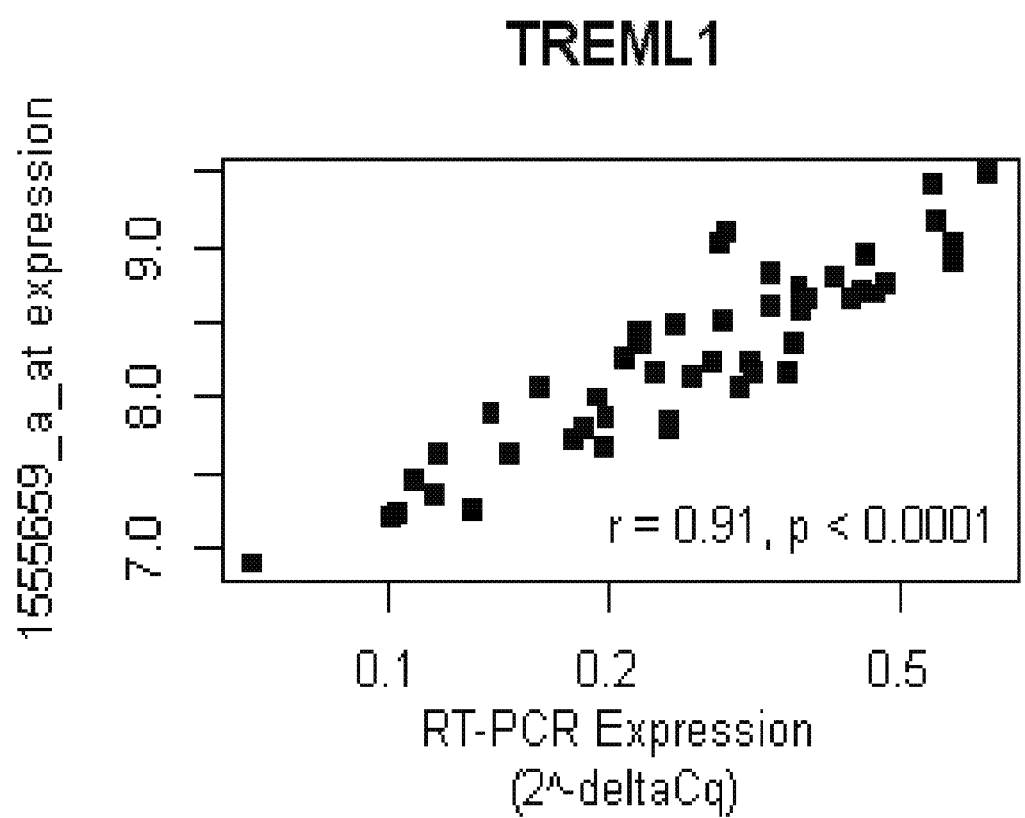
Figure 9:
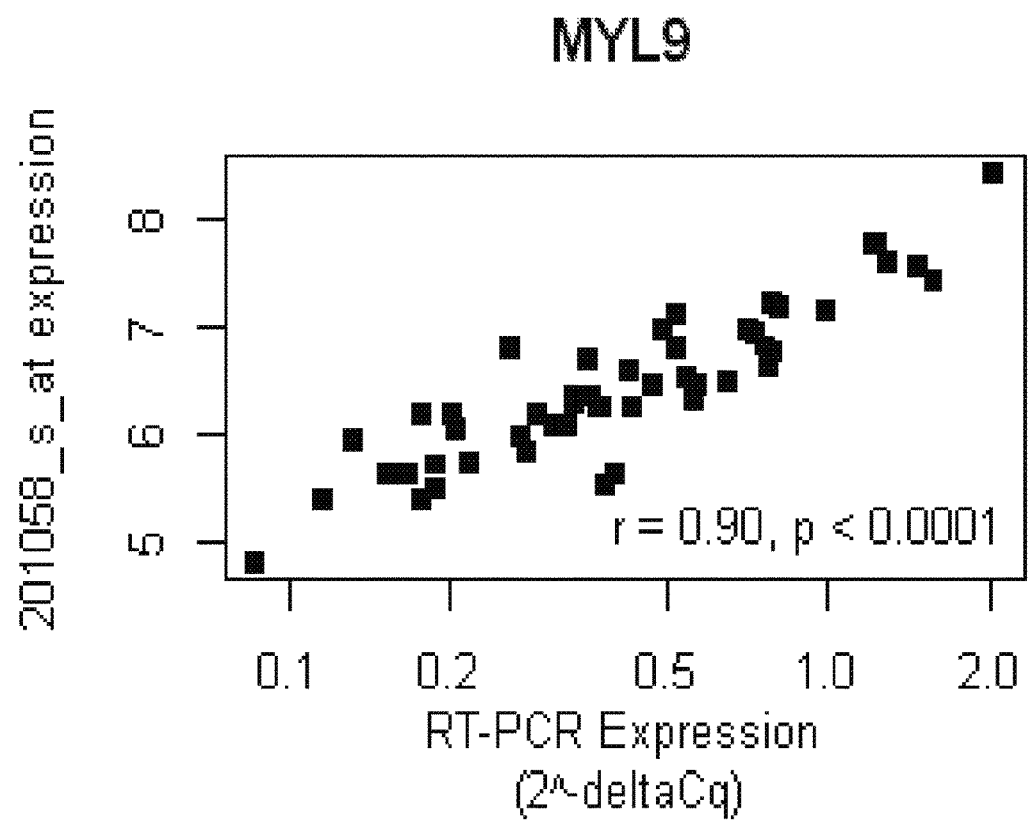
Figure 9:
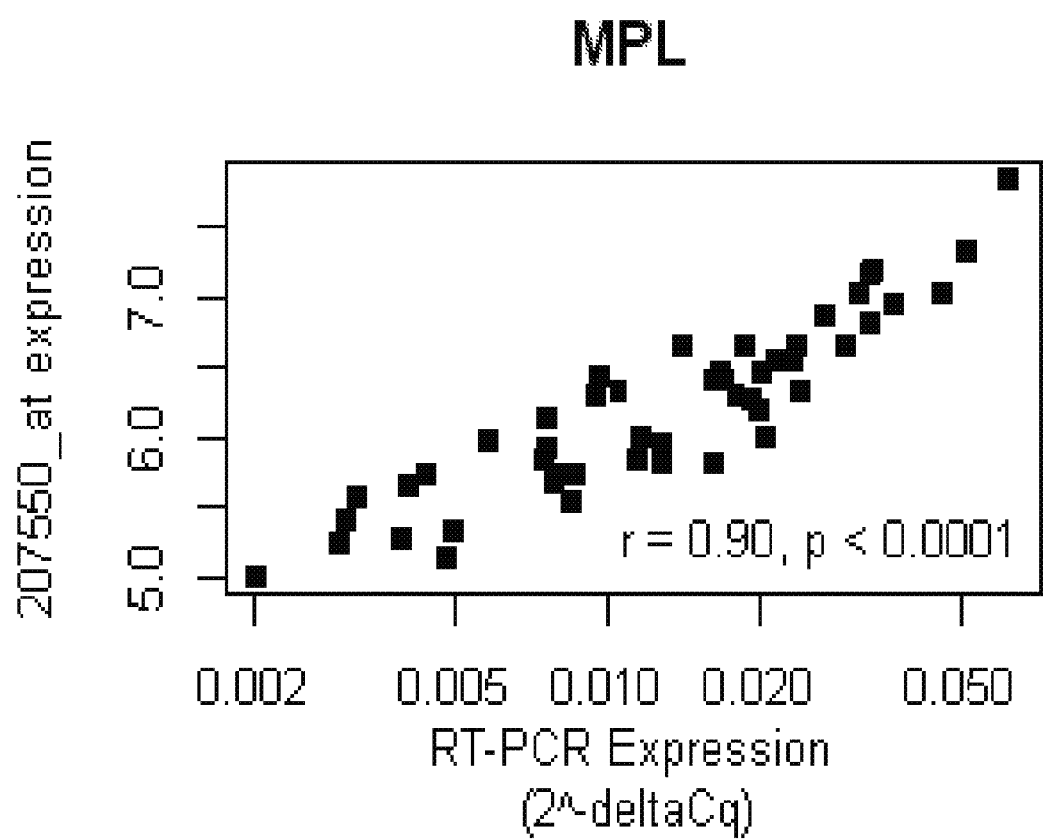

To verify the microarray-based expression of the ARS transcripts, 45 of the 64 genes (see Example 3 for selection criteria) were selected for verification in whole blood RNA from the HV2 cohort. Using RT-PCR, 42/45 transcripts significantly correlated with their microarray-based expression with 16/42 transcripts, including ITGA2B, TREML1, MYL9, and MPL, strongly (r>0.80) correlating with microarray based gene expression (FIG. 9 and Table 12). For the majority of transcripts there was concordance between both the RT-PCR and microarray correlations with PFS (Table 13 and FIG. 7). Therefore, RT-PCR assays validate the microarray-based expression associations with PFS for most ARS transcripts.

TABLE 12

Validation of microarray based gene expression for Factor 14 probe sets with RT-PCR in HV2 cohort whole blood RNA

| Gene name | Taqman RTPCR assay name | Affymetrix microarray probe set name | Correlation coefficient | Correlation p-value |
|---|---|---|---|---|
| ITGA2B | Hs01116228_m1 | 206494_s_at | −0.94421 | 9.05E−26 |
| TREML1 | Hs00698316_m1 | 1555659_a_at | −0.90545 | 3.04E−20 |
| ITGA2B | Hs01116228_m1 | 206493_at | −0.90253 | 6.28E−20 |
| MPL | Hs00180489_m1 | 207550_at | −0.89971 | 1.24E−19 |
| MYL9 | Hs00697086_m1 | 201058_s_at | −0.89826 | 1.74E−19 |
| PCSK6 | Hs00159844_m1 | 207414_s_at | −0.893 | 5.76E−19 |
| ITGA2B | Hs01116228_m1 | 216956_s_at | −0.88851 | 1.53E−18 |
| CLU | Hs00971656_m1 | 208791_at | −0.88747 | 1.90E−18 |
| CLU | Hs00971656_m1 | 208792_s_at | −0.88153 | 6.40E−18 |
| SPARC | Hs00277762_m1 | 200665_s_at | −0.87198 | 3.95E−17 |
| ALOX12 | Hs00167524_m1 | 207206_s_at | −0.86138 | 2.53E−16 |
| CMTM5 | Hs00370784_m1 | 230942_at | −0.85545 | 6.71E−16 |
| SH3BGRL2 | Hs00230283_m1 | 225354_s_at | −0.85496 | 7.26E−16 |
| CTDSPL | Hs00505109_m1 | 201906_s_at | −0.84553 | 3.12E−15 |
| PPBP | Hs00234077_m1 | 214146_s_at | −0.84171 | 5.48E−15 |
| PF4 | Hs00236998_m1 | 206390_x_at | −0.83419 | 1.59E−14 |
| PBX1 | Hs00295499_s1 | 212151_at | −0.82951 | 3.01E−14 |
| CTTN | Hs01124225_m1 | 201059_at | −0.82216 | 7.89E−14 |
| SPARC | Hs00277762_m1 | 212667_at | −0.80984 | 3.60E−13 |
| ITGB3 | Hs01001469_m1 | 204628_s_at | −0.79402 | 2.17E−12 |
| TUBB1 | Hs00258236_m1 | 230690_at | −0.79401 | 2.17E−12 |
| GNG11 | Hs00914578_m1 | 204115_at | −0.78661 | 4.78E−12 |
| TGFB1I1 | Hs00210887_m1 | 209651_at | −0.76354 | 4.63E−11 |
| PBX1 | Hs00295499_s1 | 212148_at | −0.76222 | 5.23E−11 |
| GP1BB | Hs00236857_m1 | 206655_s_at | −0.74866 | 1.75E−10 |

TABLE 12-continued

Validation of microarray based gene expression for Factor 14 probe sets with RT-PCR in HV2 cohort whole blood RNA

| Gene name | Taqman RTPCR assay name | Affymetrix microarray probe set name | Correlation coefficient | Correlation p-value |
|---|---|---|---|---|
| TUBB1 | Hs00258236_m1 | 208601_s_at | −0.74411 | 2.59E−10 |
| ELOVL7 | Hs00405151_m1 | 227180_at | −0.72899 | 8.91E−10 |
| THBS1 | Hs00962914_m1 | 201108_s_at | −0.70496 | 5.42E−09 |
| SELP | Hs00356351_m1 | 206049_at | −0.69728 | 9.30E−09 |
| SLC24A3 | Hs00221141_m1 | 57588_at | −0.65927 | 1.07E−07 |
| CALD1 | Hs00921982_m1 | 212077_at | −0.64826 | 2.04E−07 |
| SLC24A3 | Hs00221141_m1 | 219090_at | −0.63347 | 4.65E−07 |
| MYLK | Hs00364926_m1 | 224823_at | −0.6135 | 1.33E−06 |
| ARHGAP6 | Hs00241801_m1 | 206167_s_at | −0.60772 | 1.77E−06 |
| PRKAR2B | Hs00176966_m1 | 203680_at | −0.57731 | 7.45E−06 |
| PDE5A | Hs00903251_m1 | 227088_at | −0.55683 | 1.81E−05 |
| FSTL1 | Hs00907496_m1 | 208782_at | −0.53538 | 4.32E−05 |
| TTC7B | Hs00406077_m1 | 226152_at | −0.52431 | 6.62E−05 |
| GUCY1B3 | Hs00168336_m1 | 203817_at | −0.52258 | 7.07E−05 |
| MMD | Hs00948031_m1 | 203414_at | −0.39744 | 0.003528 |
| FRMD3 | Hs00604157_m1 | 230645_at | −0.21862 | 0.119455 |
| SDPR | Hs00190538_m1 | 222717_at | −0.18796 | 0.182072 |
| CPNE5 | Hs00326218_m1 | 227189_at | −0.07961 | 0.574802 |
| CCDC90A | Hs00254417_m1 | 227451_s_at | −0.06118 | 0.666593 |
| CDC14B | Hs00269351_m1 | 221556_at | −0.04119 | 0.771874 |

*coefficient and p-value correspond to Pearson correlation test between RMA normalized microarray expression for a given probe set and delta Ct (where higher values represent lower transcript abundance) for the corresponding RT-PCR assay.

TABLE 13

Concordance of correlations with PFS between microarray and RT-PCR based gene expression for Factor 14 genes in HV2 cohort

| Gene Name | Affymetrix probe set ID | RT-PCR based Correlation coefficient* | Microarray based Correlation coefficient* |
|---|---|---|---|
| CTDSPL | 201906_s_at | 0.34 | −0.38 |
| FSTL1 | 208782_at | 0.18 | −0.38 |
| ITGA2B | 216956_s_at | 0.22 | −0.37 |
| TREML1 | 1555659_a_at | 0.35 | −0.35 |
| SPARC | 212667_at | 0.23 | −0.31 |
| ITGA2B | 206494_s_at | 0.22 | −0.30 |
| ITGA2B | 206493_at | 0.22 | −0.30 |
| MPL | 207550_at | 0.30 | −0.29 |
| CTTN | 201059_at | 0.24 | −0.29 |
| CMTM5 | 230942_at | 0.24 | −0.29 |
| SELP | 206049_at | 0.19 | −0.28 |
| CLU | 208791_at | 0.23 | −0.27 |
| GP1BB | 206655_s_at | 0.27 | −0.27 |
| ITGB3 | 204628_s_at | 0.30 | −0.26 |
| TGFB1I1 | 209651_at | 0.20 | −0.25 |
| ALOX12 | 207206_s_at | 0.19 | −0.24 |
| PBX1 | 212151_at | 0.26 | −0.24 |
| CPNE5 | 227189_at | 0.33 | −0.24 |
| MYL9 | 201058_s_at | 0.31 | −0.24 |
| CLU | 208792_s_at | 0.23 | −0.22 |
| PPBP | 214146_s_at | 0.24 | −0.22 |
| SH3BGRL2 | 225354_s_at | 0.22 | −0.20 |
| PF4 | 206390_x_at | 0.30 | −0.20 |
| THBS1 | 201108_s_at | 0.13 | −0.20 |
| SLC24A3 | 57588_at | 0.06 | −0.20 |
| PBX1 | 212148_at | 0.26 | −0.19 |
| SPARC | 200665_s_at | 0.23 | −0.18 |
| GNG11 | 204115_at | 0.24 | −0.16 |
| TUBB1 | 208601_s_at | 0.16 | −0.16 |
| PCSK6 | 207414_s_at | 0.28 | −0.15 |
| SLC24A3 | 219090_at | 0.06 | −0.15 |
| PDE5A | 227088_at | 0.20 | −0.14 |
| GUCY1B3 | 203817_at | 0.17 | −0.12 |
| CALD1 | 212077_at | 0.13 | −0.11 |
| PRKAR2B | 203680_at | 0.23 | −0.10 |
| TTC7B | 226152_at | 0.00 | −0.10 |
| ARHGAP6 | 206167_s_at | 0.20 | −0.10 |
| TUBB1 | 230690_at | 0.16 | −0.09 |
| ELOVL7 | 227180_at | 0.20 | −0.08 |
| MYLK | 224823_at | 0.22 | −0.05 |
| MMD | 203414_at | 0.21 | −0.05 |
| SDPR | 222717_at | 0.21 | −0.05 |
| FRMD3 | 230645_at | −0.12 | 0.00 |
| CDC14B | 221556_at | 0.13 | 0.18 |
| CCDC90A | 227451_s_at | −0.14 | 0.28 |

*Correlation coefficients represent Pearson correlations between gene expression based on microarray or RTPCR for Factor 14 transcripts and post-aspirin platelet function score (PFS) in HV2 cohort.

Example 6

ARS Transcripts are Primarily of Platelet Origin

Genes represented by the ARS were ranked by the strength of their correlation with platelet function in response to aspirin. See Table 14. The bolded genes are those that could be used as a subset in lieu of all of the genes in the ARS to identify those with an appropriate platelet function response (or not) to antiplatelet therapy. The transcripts with the strongest correlation with PFS mapped to several well-known platelet transcripts: ITGA2B, CLU, IGF2BP3, GP1BB, and SPARC.

TABLE 14

Genes represented by the ARS and their correlation with platelet function with aspirin*

| | Gene Symbol | Gene Description | Combined PFS beta coefficient* | Combined P-value |
|---|---|---|---|---|
| Affymetrix Probe ID | | | | |
| Factor 14 | n/a | n/a Individual Factor 14 transcript | −0.76088 | 0.0017 |
| Rank | | | | |
| 1 | FSTL1 | follistatin-like 1 | −1.6579 | 0.0003 |
| 2 | CTTN | cortactin | −1.2817 | 0.0015 |
| 3 | CTDSPL | CTD (carboxy-terminal domain, RNA polymerase II, polypeptide A) small phosphatase-like | −1.3795 | 0.0025 |
| 4 | TREML1 | triggering receptor expressed on myeloid cells-like 1 | −1.0767 | 0.0034 |
| 5 | SPARC | secreted protein, acidic, cysteine-rich (osteonectin) | −1.214 | 0.0048 |
| 6 | ITGA2B | integrin, alpha 2b (platelet glycoprotein IIb of IIb/IIIa complex, antigen CD41) | −1.0689 | 0.0048 |
| 7 | CMTM5 | CKLF-like MARVEL transmembrane domain containing 5 | −1.1641 | 0.0061 |
| 8 | SLC24A3 | solute carrier family 24 (sodium/potassium/calcium exchanger), member 3 | −1.3053 | 0.0063 |
| 9 | MPL | myeloproliferative leukemia virus oncogene | −0.931 | 0.0066 |
| 10 | SLC24A3 | solute carrier family 24 (sodium/potassium/calcium exchanger), member 3 | −1.1123 | 0.008 |
| 11 | CLU | clusterin | −0.9584 | 0.0085 |
| 12 | ITGA2B | integrin, alpha 2b (platelet glycoprotein IIb of IIb/IIIa complex, antigen CD41) | −0.7279 | 0.0087 |
| 13 | CPNE5 | copine V | −1.2062 | 0.0088 |
| 14 | CLEC1B | C-type lectin domain family 1, member B | −1.2077 | 0.009 |
| 15 | ITGA2B | integrin, alpha 2b (platelet glycoprotein IIb of IIb/IIIa complex, antigen CD41) | −0.8966 | 0.0094 |
| 16 | SELP | selectin P (granule membrane protein 140 kDa, antigen CD62) | −1.1642 | 0.0104 |
| 17 | IGF2BP3 | insulin-like growth factor 2 mRNA binding protein 3 | −1.2947 | 0.0123 |
| 18 | SH3BGRL2 | SH3 domain binding glutamic acid-rich protein like 2 | −1.0895 | 0.0146 |
| 19 | PROS1 | protein S (alpha) | −1.1049 | 0.0174 |
| 20 | ALOX12 | arachidonate 12-lipoxygenase | −0.8756 | 0.0207 |
| 21 | JAM3 | junctional adhesion molecule 3 | −1.0454 | 0.0215 |
| 22 | LRRC32 | leucine rich repeat containing 32 | −0.9376 | 0.0226 |
| 23 | ITGB3 | integrin, beta 3 (platelet glycoprotein IIIa, antigen CD61) | −0.968 | 0.0242 |
| 24 | PPBP | pro-platelet basic protein (chemokine (C—X—C motif) ligand 7) | −0.713 | 0.0243 |
| 25 | MGLL | monoglyceride lipase | −1.0027 | 0.0249 |
| 26 | CLU | clusterin | −0.8122 | 0.0266 |
| 27 | THBS1 | thrombospondin 1 | −0.9169 | 0.0276 |
| 28 | MYL9 | myosin, light chain 9, regulatory | −0.5909 | 0.0287 |
| 29 | PF4 | platelet factor 4 (chemokine (C—X—C motif) ligand 4) | −0.9017 | 0.0296 |
| 30 | GP1BB | glycoprotein Ib (platelet), beta polypeptide | −0.8934 | 0.0317 |
| 31 | TGFB1I1 | transforming growth factor beta 1 induced transcript 1 | −0.7618 | 0.0326 |
| 32 | PCSK6 | proprotein convertase subtilisin/kexin type 6 | −0.8566 | 0.0351 |
| 33 | SPARC | secreted protein, acidic, cysteine-rich (osteonectin) | −0.8261 | 0.041 |
| 34 | CALD1 | caldesmon 1 | −0.5688 | 0.0505 |
| 35 | GUCY1B3 | guanylate cyclase 1, soluble, beta 3 | −0.8511 | 0.0546 |
| 36 | PDE5A | phosphodiesterase 5A, cGMP-specific | −0.918 | 0.0571 |
| 37 | TTC7B | tetratricopeptide repeat domain 7B | −0.7986 | 0.0594 |
| 38 | ARHGAP6 | Rho GTPase activating protein 6 | −0.8437 | 0.0677 |

TABLE 14-continued

Genes represented by the ARS and their correlation with platelet function with aspirin*

|    | Gene Symbol | Gene Description | Combined PFS beta coefficient* | Combined P-value |
|----|-------------|------------------|-------------------------------|------------------|
| 39 | PARVB | parvin, beta | −0.7708 | 0.0717 |
| 40 | TUBB1 | tubulin, beta 1 | −0.5959 | 0.0736 |
| 41 | GNG11 | guanine nucleotide binding protein (G protein), gamma 11 | −0.5622 | 0.1229 |
| 42 | PRSS1 | protease, serine, 1 (trypsin 1) | −0.4814 | 0.1243 |
| 43 | PRKAR2B | protein kinase, cAMP-dependent, regulatory, type II, beta | −0.5049 | 0.1365 |
| 44 | MFAP3L | microfibrillar-associated protein 3-like | −0.4724 | 0.1385 |
| 45 | PBX1 | pre-B-cell leukemia transcription factor 1 | −0.6059 | 0.1729 |
| 46 | ENDOD1 | endonuclease domain containing 1 | −0.7276 | 0.1735 |
| 47 | TUBB1 | tubulin, beta 1 | −0.578 | 0.1864 |
| 48 | FRMD3 | FERM domain containing 3 | −0.6391 | 0.2102 |
| 49 | TMEM64 | transmembrane protein 64 | 0.38321 | 0.2227 |
| 50 | BEND2 | chromosome X open reading frame 20 | −0.5657 | 0.2258 |
| 51 | RAB27B | RAB27B, member RAS oncogene family | −0.4836 | 0.2512 |
| 52 | ELOVL7 | ELOVL family member 7, elongation of long chain fatty acids (yeast) | −0.3943 | 0.2823 |
| 53 | PBX1 | pre-B-cell leukemia transcription factor 1 | −0.3139 | 0.297 |
| 54 | MMD | monocyte to macrophage differentiation-associated | −0.4287 | 0.3236 |
| 55 | CLEC4D | C-type lectin domain family 4, member D | 0.37545 | 0.3543 |
| 56 | SDPR | serum deprivation response (phosphatidylserine binding protein) | −0.3009 | 0.383 |
| 57 | MYLK | myosin, light chain kinase | −0.2911 | 0.4644 |
| 58 | CXCL5 | chemokine (C—X—C motif) ligand 5 | −0.1621 | 0.5011 |
| 59 | C12ORF39 | chromosome 12 open reading frame 39 | −0.2032 | 0.502 |
| 60 | PCGF5 | polycomb group ring finger 5 | 0.22781 | 0.547 |
| 61 | RHOBTB1 | Rho-related BTB domain containing 1 | −0.2395 | 0.5755 |
| 62 | HIST1H3H | histone cluster 1, H3h | −0.2021 | 0.5827 |
| 63 | HIST1H2BG | histone cluster 1, H2bg | −0.2623 | 0.5896 |
| 64 | PF4V1 | platelet factor 4 variant 1 | −0.0927 | 0.6139 |
| 65 | LGALSL | lectin, galactoside-binding-like- | 0.23728 | 0.6142 |
| 66 | CDC14B | CDC14 cell division cycle 14 homolog B (S. cerevisiae) | −0.2127 | 0.653 |
| 67 | HIST1H2AG | histone cluster 1, H2ag | −0.1534 | 0.6882 |
| 68 | HIST1H2BG | histone cluster 1, H2bg | −0.1494 | 0.6906 |
| 69 | ARHGAP18 | Rho GTPase activating protein 18 | 0.15541 | 0.7353 |
| 70 | RAB4A | RAB4A, member RAS oncogene family | 0.09962 | 0.7967 |
| 71 | TPM1 | tropomyosin 1 (alpha) | 0.08749 | 0.8404 |
| 72 | C6ORF79 | chromosome 6 open reading frame 79 | −0.0134 | 0.9791 |

*= the beta coefficient for the expression of either the aggregate expression of the ARS or each probe set represented by the ARS using the combined HV1 and HV2 datasets from a regression model containing gene expression and cohort (HV1 vs. HV2) with corresponding p-value; PFS = platelet function score.

Based on this observation it was hypothesized that transcripts represented by the ARS were of platelet origin. To test this hypothesis, the overlap and enrichment of the 64 genes represented by the ARS were examined with pre-defined gene sets specific to various peripheral blood cell types. Up to 24 of the 64 ARS genes significantly overlapped with platelet- or megakaryocyte-specific genes, whereas none overlapped with non-platelet peripheral blood cell type genes (Tables 15 and 16). Further, in the CATHGEN cohorts, the strongest correlation was found between expression of the ARS and platelet count ($r=0.41$, $p<2e^{-16}$) with no strong, positive correlations with any other peripheral blood cell type counts: white blood cells ($r=-0.01$, $p=0.87$), lymphocytes ($r=-0.25$, $p=1.2e-05$), neutrophils ($r=0.16$, $p=0.01$), or monocytes ($r=0.06$, $p=0.27$).

TABLE 15

Comparison of platelet and megakaryocyte genes with Factor 14

| Gene set description* | Number of features | Number of overlapping genes with Factor 14*** | GSEA NES | GSEA P-value | GSEA Q-value** | Reference |
|---|---|---|---|---|---|---|
| Factor 14 genes (reference) | 62 | 62 | 2.23 | <0.0001 | <0.0001 | N/A |

TABLE 15-continued

Comparison of platelet and megakaryocyte genes with Factor 14

| Gene set description* | Number of features | Number of overlapping genes with Factor 14*** | GSEA NES | GSEA P-value | GSEA Q-value** | Reference |
|---|---|---|---|---|---|---|
| Platelet genes (A) | 248 | 25 | 2.18 | <0.0001 | <0.0001 | 1 |
| Platelets specific genes (B) | 36 | 12 | 2.12 | <0.0001 | 0.001 | 2 |
| Megakaryocytes genes (C) | 261 | 20 | 2.06 | <0.0001 | 0.001 | 3 |
| Platelet genes (D) | 196 | 14 | 1.97 | <0.0001 | 0.008 | 4 |
| Platelet proteins (E) | 99 | 31 | 1.84 | <0.0001 | 0.01 | 5 |
| Platelet genes (F) | 36 | 6 | 1.73 | 0.004 | 0.02 | 6 |

GSEA = Gene Set Enrichment Analysis (GSEA);
NES = Normalized enrichment score;
*The gene lists were as follows: A) the abundant platelet transcripts identified by RNA-sequencing1; B) platelet-specific transcripts identified in platelets of sickle cell disease patients or controls2; C) megakaryocyte-specific genes3; D) abundant platelet genes identified in platelets of patients with systemic lupus or controls4; or E) platelet proteins from healthy donors5; F) the top 50 genes identified in purified platelets from healthy volunteers6;
**refers to false discovery rate q-value;
***p ≤ 0.001 for all overlaps.

TABLE 16

Comparison of Factor 14 genes with non-platelet derived peripheral blood cell-type genes*.

| Gene set description* | Number of features | Number of overlapping genes with Factor 14* | GSEA NES | GSEA P-value** | GSEA Q-value*** |
|---|---|---|---|---|---|
| CD4+ Th lymphocytes | 36 | 0 | −0.7 | 0.7 | 0.7 |
| CD8+ Tc lymphocytes | 4 | 0 | 0.7 | 0.7 | 0.8 |
| CD14+ Monocytes | 164 | 0 | 0.6 | 0.8 | 0.9 |
| CD19+ B lymphocytes | 53 | 0 | 0.5 | 1.0 | 0.9 |
| CD56+ NK cells | 605 | 0 | 1.4 | 0.2 | 0.2 |
| CD66+ granulocytes | 257 | 0 | 1.7 | 0.03 | 0.03 |
| Erythroblasts | 38 | 0 | 1.3 | 0.2 | 0.2 |

*Cell-type specific gene lists were obtained from Watkins et al. (2009) 113: e1-e9; Abbreviations and footnotes are per Table 2.

To confirm the platelet origin of the ARS genes, purified platelet lysates were analyzed by label-free proteomics in the HV2 cohort. 17 proteins from the ARS gene set were identified in the proteomics dataset, of which, six were associated with PFS including ITGA2B, ITGB3, and MYL9 (Table 17), all in the same direction their corresponding transcripts. Therefore, from these data it was concluded that a large number of ARS transcripts originate in platelets and are thus reporting on a coexpressed pathway of platelet transcripts and proteins associated with platelet function on aspirin.

TABLE 17

ARS proteins identified in platelet protein and their correlations with PFS on aspirin

| Protein Name | Correlation with PFS | p-value |
|---|---|---|
| TBB1 | −0.32 | 0.02 |
| GP1BB | −0.29 | 0.03 |
| ITA2B | −0.29 | 0.03 |
| ITB3 | −0.28 | 0.04 |
| MYL9 | −0.27 | 0.05 |
| RB27B | −0.26 | 0.06 |
| LEGL | −0.24 | 0.08 |
| TSP1 | −0.24 | 0.08 |
| CALD1 | −0.22 | 0.11 |
| SRC8 | −0.21 | 0.12 |
| SH3L2 | −0.20 | 0.16 |

TABLE 17-continued

ARS proteins identified in platelet protein and their correlations with PFS on aspirin

| Protein Name | Correlation with PFS | p-value |
|---|---|---|
| CXCL7 | −0.20 | 0.15 |
| SDPR | −0.18 | 0.19 |
| PLF4 | −0.18 | 0.20 |
| SPRC | −0.14 | 0.31 |
| PDE5A | −0.09 | 0.49 |
| CLUS | 0.06 | 0.67 |

Because mean platelet volume (MPV) is associated with platelet function and the platelet origin of ARS transcripts, the extent to which the association between ARS and PFS was confounded by platelet volume or count was assessed. After controlling for MPV, the ARS remained significantly (adjusted regression coefficient for ARS=−0.5, standard error=0.2, and p-value=0.05 for HV1; and −0.87, 0.4, and p-value=0.03 for HV2) associated with PFS. Further, in HV1, where platelet count and volume were both measured, the ARS remained significantly (−0.5±0.2, p=0.04) associated with PFS after their inclusion. Therefore, the association between ARS and platelet function is independent of other readily available platelet parameters such as count and MPV.

Prior to the Administration of Aspirin, the ARS is not Associated with Platelet Function.

Figure 10:
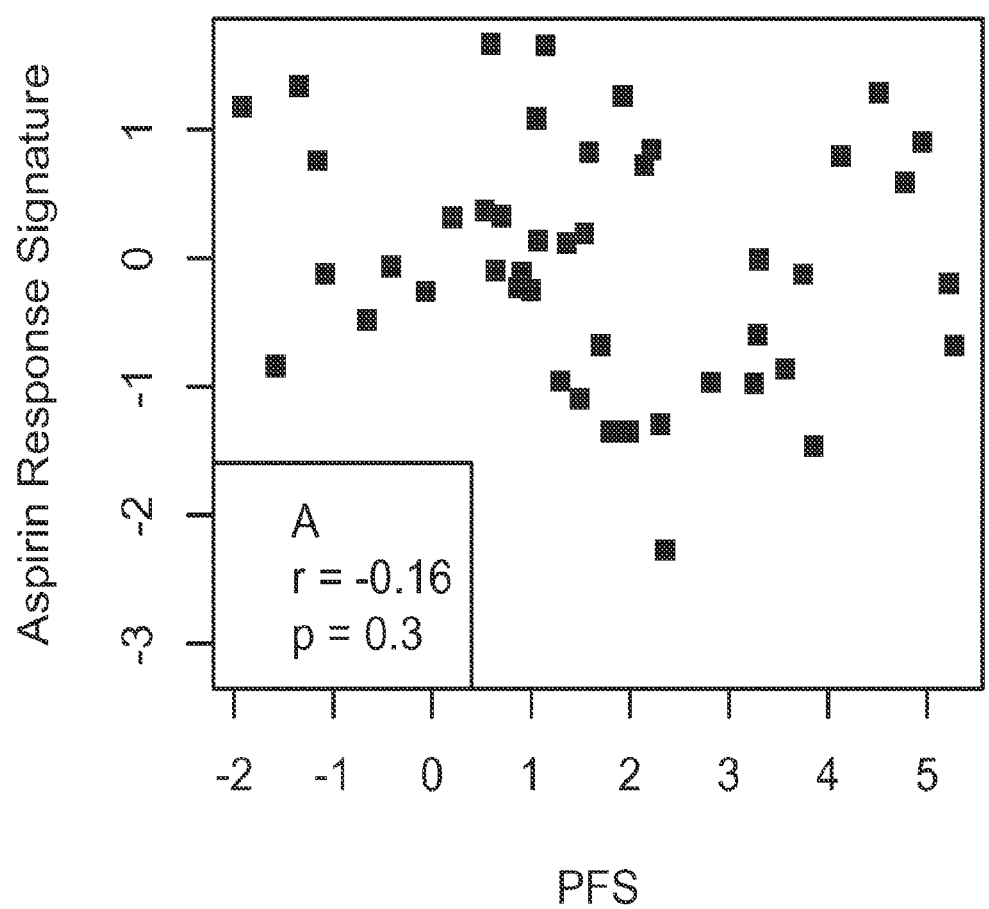
FIG. 10 shows that a set of coexpressed peripheral blood genes does not correlate with native, pre-aspirin platelet function. The aggregate expression of coexpressed genes was plotted against the platelet function before the administration of aspirin in the discovery cohort (HV1, A, n=45) and validation cohort (HV2, B, n=50) healthy volunteers. Pearson correlation coefficients and p-values are reported. ARS=aspirin response signature; PFS=platelet function score.
Figure 10:
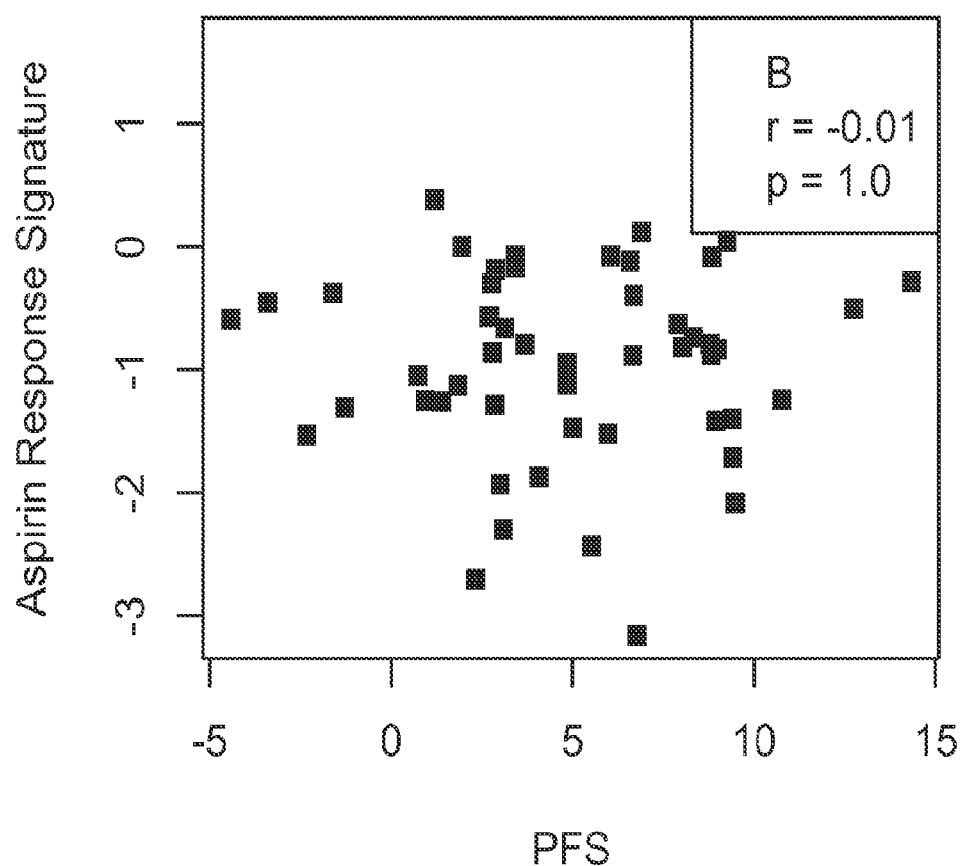

Because pre-aspirin platelet function is a strong predictor of post-aspirin platelet function, the hypothesis that the aggregate expression of the ARS genes was correlated with native, pre-aspirin PFS was tested. In neither HV1 nor HV2 was a correlation between the ARS and pre-aspirin PFS observed (FIG. 10). Despite the absence of a correlation with PFS prior to aspirin, the ARS genes were similarly co-expressed before and after aspirin exposure (FIG. 8). Therefore, although the set of ARS genes are highly correlated with one another prior to aspirin exposure, their aggregate expression does not appear to contribute to native, pre-aspirin platelet function. Instead, the expression of the ARS genes specifically reflects platelet function on aspirin.

The ARS is an Independent Prognostic Biomarker for Cardiovascular Events.

Because of the association of the ARS with platelet function on aspirin and aspirin's role in preventing cardiovascular events, the hypothesis that the ARS was associated with the risk of death/MI in two independent patient cohorts was tested. ARS individual probe sets are associated with death or myocardial infarction in two independent datasets. Genes are ranked based on strength of association with death/MI. Bolded genes are those that may be used as a subset of genes in lieu of all of the genes in the ARS. In both case-control and observational cohorts, the ARS was significantly associated with death/MI in univariate analyses (odds ratio [OR]=1.2, 95% confidence interval [CI]=1.04-1.4, p=0.04 and hazard ratio [HR]=1.4, [CI]=1.1-1.7, p=0.002, respectively). The majority of the individual transcripts represented by the ARS were also associated with death/MI in both cohorts. (Table 18).

TABLE 18

Factor 14 individual probe sets are associated with death or myocardial infarction in two independent datasets.

| | Gene name | Odds Ratio* | Odds Ratio p-value | Hazard Ratio* | Hazard Ratio p-value |
|---|---|---|---|---|---|
| Probe set ID | | | | | |
| Factor 14 | n/a | 1.21 | 0.028036541 | 1.47 | 0.001454 |
| Factor 14 individual probe set associations | | | | | |
| Ranking | | | | | |
| 1 | MYL9 | 1.3 | 0.00400748 | 1.75 | 7.65E−06 |
| 2 | ITGA2B | 1.37 | 0.00351754 | 1.83 | 1.88E−05 |
| 3 | ITGA2B | 1.52 | 0.000531982 | 1.82 | 3.09E−05 |
| 4 | CMTM5 | 1.31 | 0.066298986 | 2.52 | 3.50E−05 |
| 5 | TREML1 | 1.36 | 0.010689841 | 1.89 | 5.63E−05 |
| 6 | ENDOD1 | 1.94 | 4.95E−05 | 2.1 | 0.000188 |
| 7 | PBX1 | 1.46 | 2.45E−06 | 1.47 | 0.0002 |
| 8 | LGALSL | 1.38 | 0.071992059 | 2.62 | 0.000206 |
| 9 | PBX1 | 1.65 | 1.48E−05 | 1.73 | 0.000281 |
| 10 | ITGA2B | 1.46 | 0.002887947 | 1.83 | 0.000351 |
| 11 | TPM1 | 1.87 | 1.45E−05 | 1.83 | 0.000422 |
| 12 | SLC24A3 | 1.15 | 0.440525089 | 2.19 | 0.000472 |
| 13 | TGFB1I1 | 1.32 | 0.015158949 | 1.63 | 0.000616 |
| 14 | IGF2BP3 | 1.45 | 0.033315085 | 1.86 | 0.000619 |
| 15 | SELP | 1.46 | 0.021063226 | 2.01 | 0.000636 |
| 16 | CLEC4D | 1.48 | 0.00175683 | 1.74 | 0.000708 |
| 17 | TTC7B | 1.43 | 0.029162426 | 2.06 | 0.000931 |
| 18 | ITGB3 | 1.41 | 0.059389555 | 1.81 | 0.00112 |
| 19 | CLU | 1.56 | 0.002006075 | 1.84 | 0.001166 |
| 20 | GP1BB | 1.32 | 0.043694557 | 1.69 | 0.001235 |
| 21 | HIST1H2BG | 1.74 | 0.000124728 | 1.98 | 0.001269 |
| 22 | THBS1 | 1.39 | 0.02328534 | 1.87 | 0.001633 |
| 23 | CLU | 1.51 | 0.003791609 | 1.8 | 0.001869 |
| 24 | SLC24A3 | 1.16 | 0.373804241 | 2.01 | 0.001907 |
| 25 | TMEM64 | 0.59 | 0.008235562 | 0.41 | 0.002877 |

TABLE 18-continued

Factor 14 individual probe sets are associated with death or myocardial infarction in two independent datasets.

| | Gene name | Odds Ratio* | Odds Ratio p-value | Hazard Ratio* | Hazard Ratio p-value |
|---|---|---|---|---|---|
| 26 | ALOX12 | 1.21 | 0.138154505 | 1.74 | 0.003564 |
| 27 | C12orf39 | 1.39 | 0.004259803 | 1.58 | 0.005073 |
| 28 | HIST1H2BG | 1.68 | 0.002837678 | 1.81 | 0.005208 |
| 29 | PARVB | 1.04 | 0.771921449 | 1.81 | 0.005396 |
| 30 | SH3BGRL2 | 1.34 | 0.049135136 | 1.79 | 0.00551 |
| 31 | SPARC | 1.25 | 0.167170138 | 1.78 | 0.005604 |
| 32 | PCSK6 | 1.23 | 0.150039721 | 1.72 | 0.006252 |
| 33 | PCGF5 | 1.93 | 5.27E−06 | 1.42 | 0.006562 |
| 34 | SPARC | 1.44 | 0.008859476 | 1.72 | 0.006808 |
| 35 | PROS1 | 1.45 | 0.018336331 | 1.58 | 0.006933 |
| 36 | CALD1 | 1.11 | 0.338890694 | 1.52 | 0.006972 |
| 37 | CTDSPL | 1.3 | 0.11440241 | 1.9 | 0.007299 |
| 38 | TRBV27 | 1.28 | 0.019888406 | 1.52 | 0.011429 |
| 39 | PF4 | 1.13 | 0.398156787 | 1.85 | 0.0117 |
| 40 | MGLL | 1.16 | 0.327461963 | 1.85 | 0.012801 |
| 41 | FRMD3 | 1.85 | 0.000131807 | 1.79 | 0.014483 |
| 42 | HIST1H3H | 1.72 | 3.26E−05 | 1.57 | 0.018138 |
| 43 | TUBB1 | 1.16 | 0.201369942 | 1.5 | 0.01831 |
| 44 | PRKAR2B | 1.43 | 0.005278287 | 1.54 | 0.025644 |
| 45 | ELOVL7 | 1.25 | 0.070697319 | 1.49 | 0.032551 |
| 46 | PPBP | 1.55 | 0.000423437 | 1.83 | 0.037707 |
| 47 | CPNE5 | 0.71 | 0.079532372 | 1.63 | 0.03795 |
| 48 | FSTL1 | 1.28 | 0.086692126 | 1.53 | 0.039651 |
| 49 | LRRC32 | 1.24 | 0.155422462 | 1.55 | 0.050918 |
| 50 | CTTN | 1.16 | 0.299273772 | 1.53 | 0.057153 |
| 51 | CLEC1B | 1.5 | 0.002955397 | 1.43 | 0.079647 |
| 52 | RHOBTB1 | 1.32 | 0.08218736 | 1.43 | 0.096564 |
| 53 | GNG11 | 1.41 | 0.004779687 | 1.45 | 0.118268 |
| 54 | ARHGAP6 | 1.14 | 0.422952376 | 1.36 | 0.151355 |
| 55 | PDE5A | 1.35 | 0.046937627 | 1.37 | 0.151501 |
| 56 | GUCY1B3 | 1.28 | 0.098280545 | 1.35 | 0.160362 |
| 57 | MPL | 1.05 | 0.717720328 | 1.28 | 0.210728 |
| 58 | BEND2 | 1.42 | 0.079659139 | 1.33 | 0.233 |
| 59 | JAM3 | 0.97 | 0.872083306 | 1.34 | 0.240894 |
| 60 | TUBB1 | 1.09 | 0.589122948 | 1.31 | 0.265404 |
| 61 | HIST1H2AG | 1.54 | 0.004128653 | 1.27 | 0.303256 |
| 62 | ARHGAP18 | 1.53 | 0.034773026 | 1.3 | 0.338505 |
| 63 | MYLK | 1.24 | 0.099105304 | 1.21 | 0.357528 |
| 64 | CCDC90A | 1.07 | 0.751398281 | 0.76 | 0.381367 |
| 65 | RAB27B | 1.21 | 0.257379973 | 0.84 | 0.546707 |
| 66 | PF4V1 | 1.07 | 0.397575492 | 1.07 | 0.581265 |
| 67 | CDC14B | 0.78 | 0.197214947 | 0.86 | 0.60266 |
| 68 | SDPR | 1.08 | 0.545883997 | 1.1 | 0.679631 |
| 69 | RAB4A | 1.54 | 0.020878373 | 0.91 | 0.803266 |
| 70 | CXCL5 | 0.88 | 0.201323204 | 0.97 | 0.867518 |
| 71 | MFAP3L | 0.9 | 0.409405359 | 1.01 | 0.968416 |
| 72 | MMD | 1.19 | 0.292053865 | 1.01 | 0.985414 |

*Individual Factor 14 probe sets were associated with death or myocardial infarction in the case control and observational cohorts, yielding odds ratios and hazards ratios, respectively. For each probe set analyses were adjusted for log(platelet count), race, and sex.

To determine the extent to which the ARS or an individual probe set for ITGA2B was an independent prognostic biomarker for events, the CATHGEN cohorts were combined and it was found that the ARS (OR=1.3, CI=[1.1, 1.5], p=0.001) or the microarray-based expression of ITGA2B (probe set=206494_s_at, OR=1.5, CI=[1.2, 1.8], p=0.0001) were independently associated with death/MI after adjustment for Framingham risk factors, race, platelet count, and presence of angiographic CAD.

Figure 11:
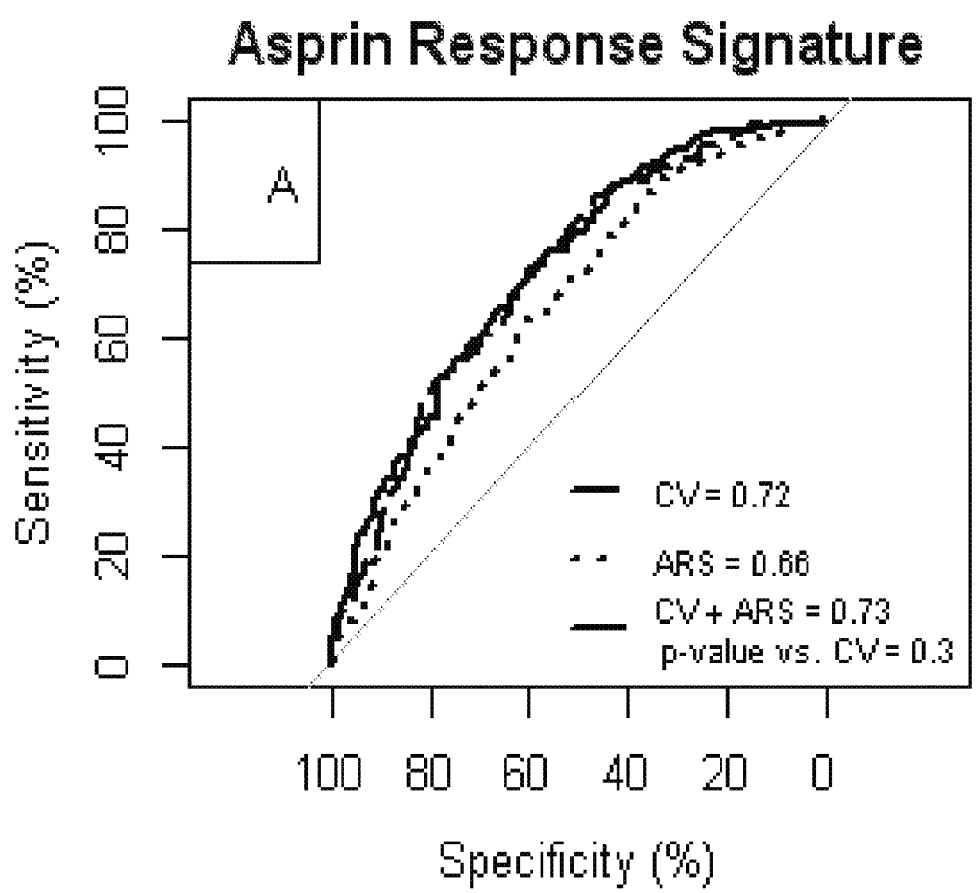
FIG. 11 shows that peripheral blood gene expression adds additional prognostic information for death or myocardial infarction. Patients in the case:control and observational cohorts were combined and analyzed with respect to death/myocardial infarction (MI) outcomes. The receiver operating characteristics curves were plotted for predictive models containing cardiovascular risk factors, platelet count, presence of coronary artery disease, cohort (collectively, CV) and gene expression, or both were compared. ARS=aspirin response signature. The probe set, 216956_s_at represents ITGA2B gene expression.
Figure 11:
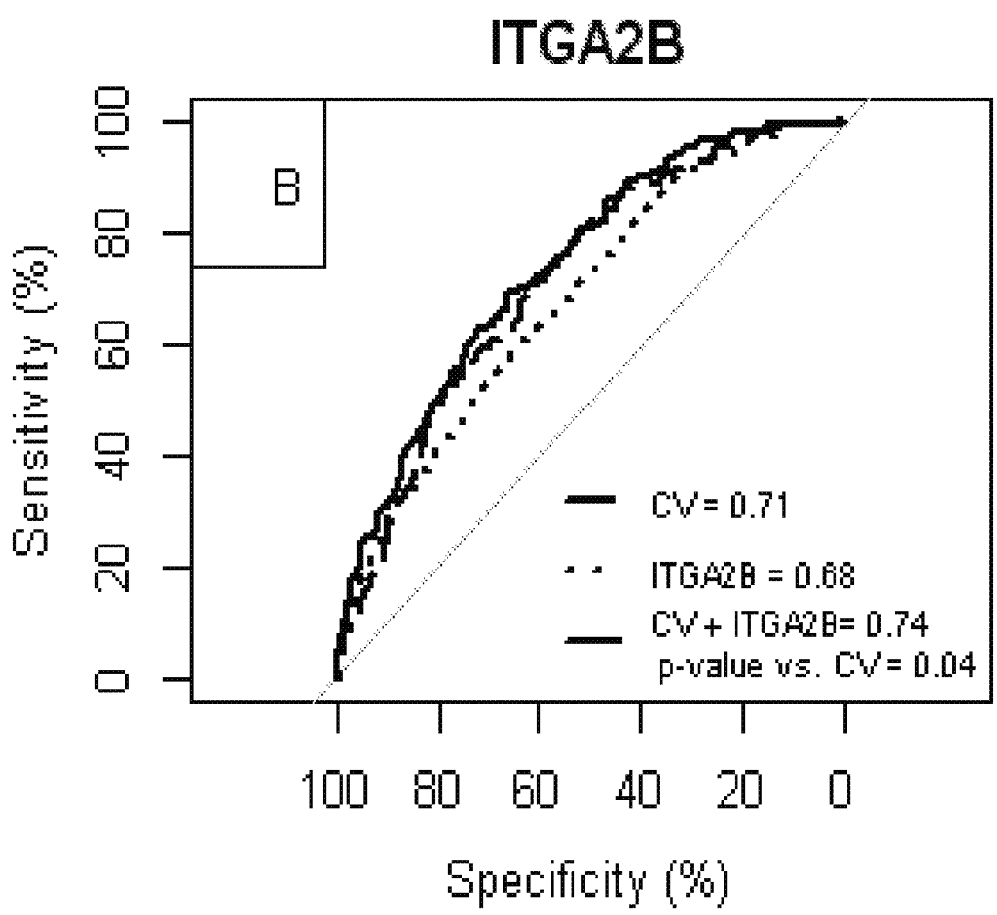

To further assess the potential use of the ARS as a risk biomarker, the hypothesis that the ARS or ITGA2B probe set expression would improve measures of discrimination was tested. Compared with a model using clinical risk factors alone, the inclusion of the ARS improved most measures of risk discrimination (Table 19, FIG. 11A). Inclusion of ITGA2B probe set expression significantly improved all measures of discrimination (Table 19, FIG. 11B). Thus, the ARS and/or the expression of an individual ARS transcript, such as ITGA2B, were independent prognostic biomarkers for risk of death/MI.

TABLE 19

Measures of discrimination with and without inclusion of gene expression profiles

| Measure | Traditional Risk Factors | Traditional Risk Factors + ARS | Traditional Risk Factors + 216956_s_at** (ITGA2B) |
|---|---|---|---|
| Area under ROC curve | 0.72 | 0.73 | 0.74 |
| 95% confidence interval [CI] | [0.68-0.76] | [0.69-0.77] | [0.70-0.78] |
| p-value* | n/a | 0.3 | 0.04 |
| Net reclassification index (<10%, 10-20%, >20%) | — | 0.06 | 0.12 |
| CI | | [0.02-0.10] | [0.07-0.17] |
| p-value | | 0.005 | <1e−05 |
| Net reclassification index (category-free) | — | 0.31 | 0.37 |
| CI | | [0.15-0.47] | [0.21-0.54] |
| p-value | | 2e−04 | 8.7e−06 |
| Integrated discrimination improvement | — | 0.01 | 0.03 |
| CI | | [0.002-0.02] | [0.02-0.05] |
| p-value | | 0.006 | 2e−05 |

*all p-values are for comparisons with 'Traditional Risk Factors' model which includes: age, sex, African-American race, smoking, diabetes, hypertension, hyperlipidemia, cohort, and the presence of coronary artery disease;
**The 216956_s_at probe set represents ITGA2B gene expression on the Affymetrix microarray; ARS = aspirin response signature; ROC = receiver operating characteristic Example 7

Aspirin and RUNX1

Description of Available Cohorts with Peripheral Blood Microarray Data.

Patients with cardiovascular disease and long term outcomes from CATHGEN cohort (observational cohort and case-control cohort) studied as described in the Examples above.

Platelet Purification and RNA Isolation.

Platelets were purified from 40 cc of whole blood from HV2 subjects according to a previously described protocol (Schedel et al. (2009) Methods Mol Biol 496:273-283; Rox et al. (2009) Methods Mol Biol 496:285-292).

Platelet RNA RT-PCR for RUNX1 Transcripts from Healthy Volunteer Cohort.

The transcripts were selected and the TagMan™ low density array methods (Life Technologies; Grand Island, N.Y.) used were similar to the methods described in the "Real-Time PCR" section of Example 3.

Selection of RUNX1 Probe Sets for Microarray Studies.

RUNX1 is transcribed from two promoters (distal P1 and proximal P2). The subsequent transcripts share a common Runt DNA binding domain, though differ in their 5' untranslated regions, N-terminal domains, and initial exon composition. Using four available datasets of whole blood gene expression data generated on the Affymetrix U133 plus 2.0 microarray, 12 probe sets that mapped to the RUNX1 locus were selected (208129_x_at, 209359_x_at, 210365_at, 210805_x_at, 211179_at, 211180_x_at, 211181_x_at, 211182_x_at, 217263_x_at, 209360_s_at, 233690_at, 220918_at)

The 12 probe sets cover transcripts derived from the P1 and P2 promoters, of which three (220918_at, 233690_at, and 209360_s_at) map to P1-specific transcripts, while the remainder are non-specific.

Figure 12:
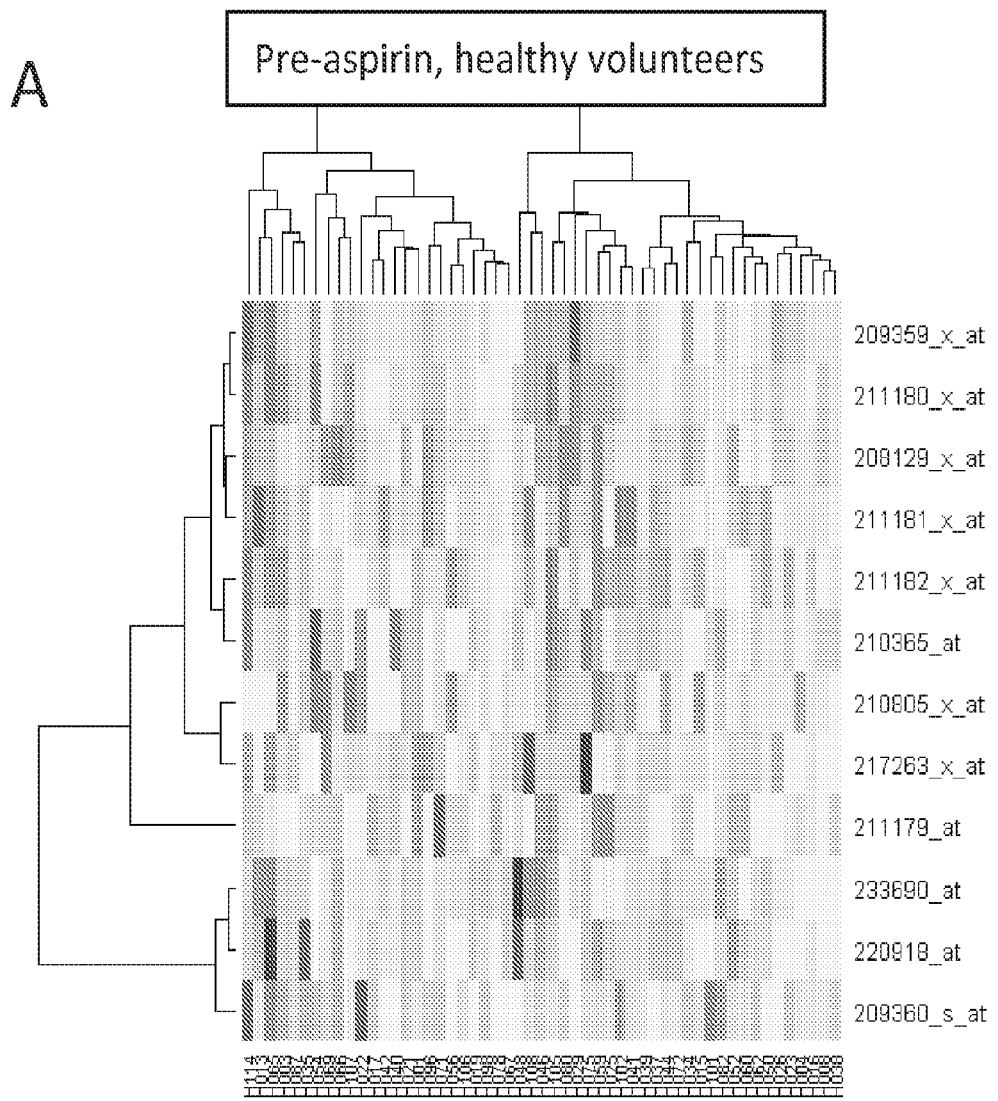
FIG. 12 shows that RUNX1 probe sets cluster into two distinct clusters representing P1 and P2 driven transcription.
Figure 12:
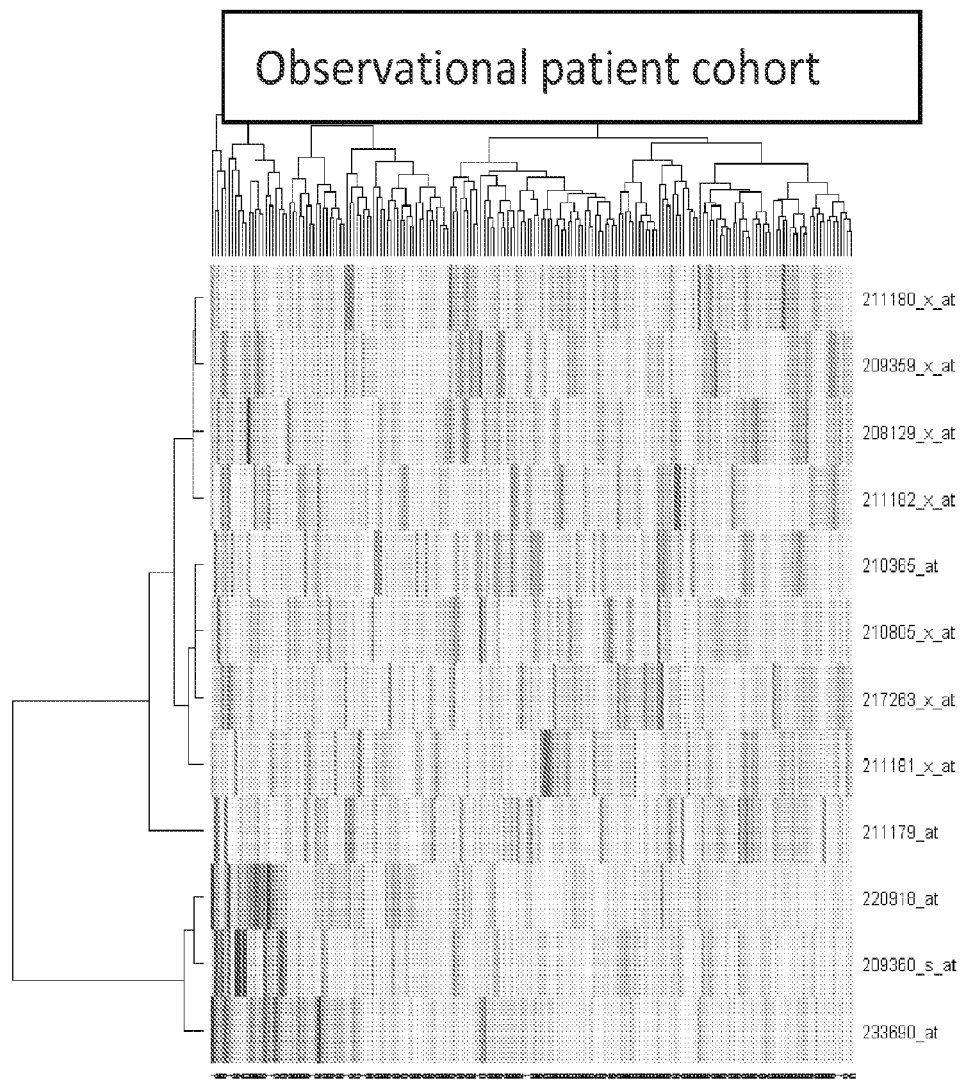
Figure 12:
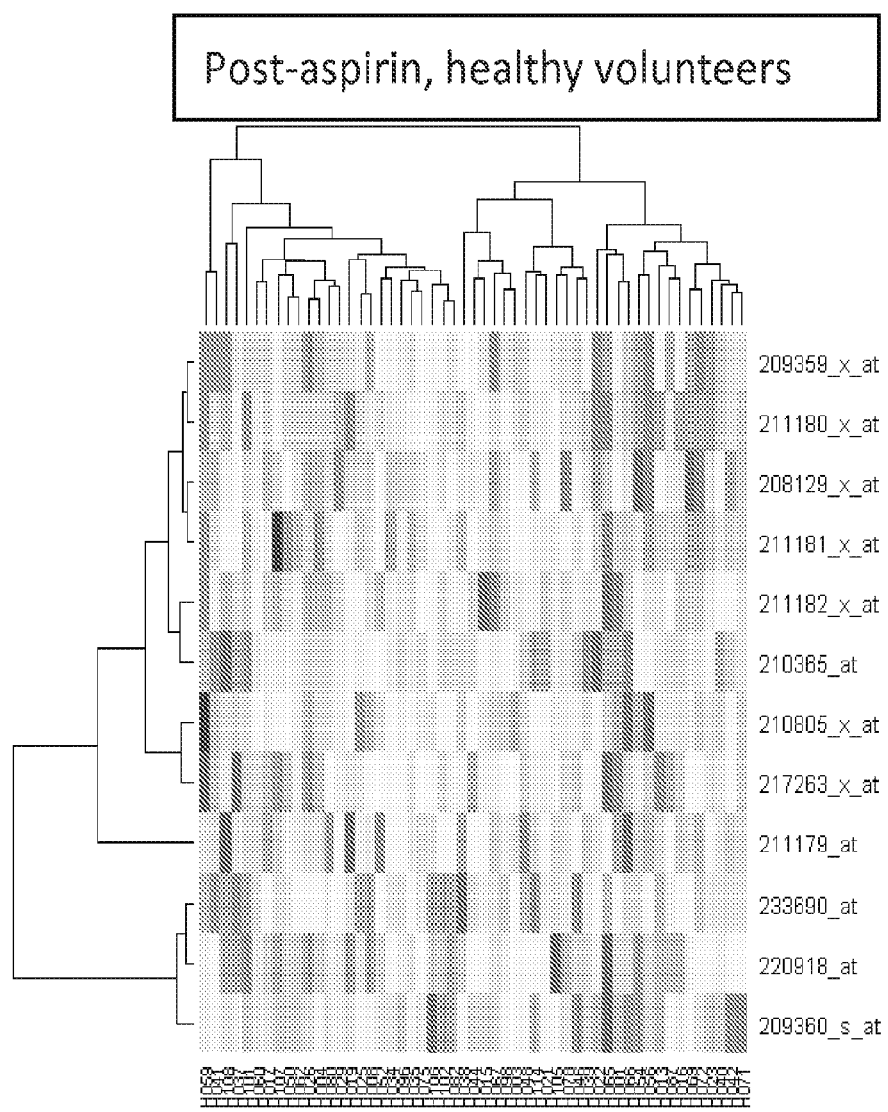
Figure 12:
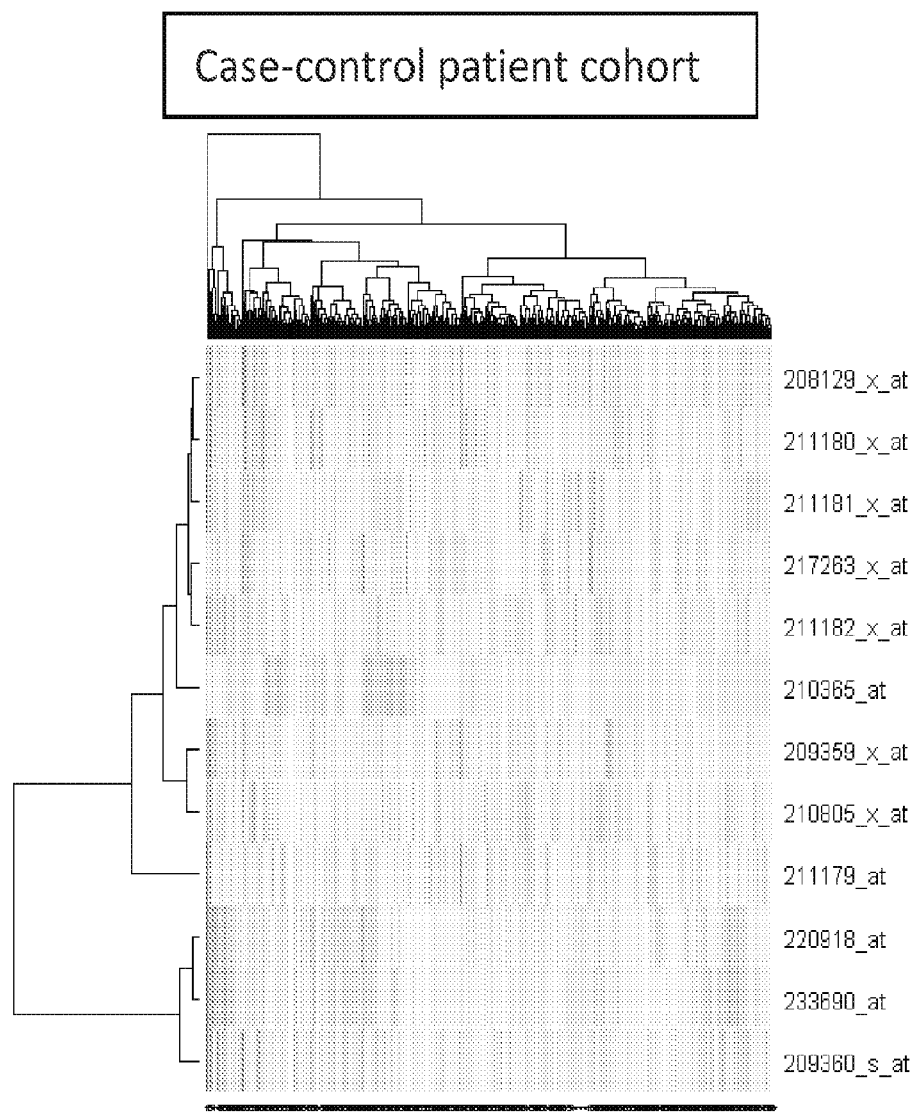
Figure 12:
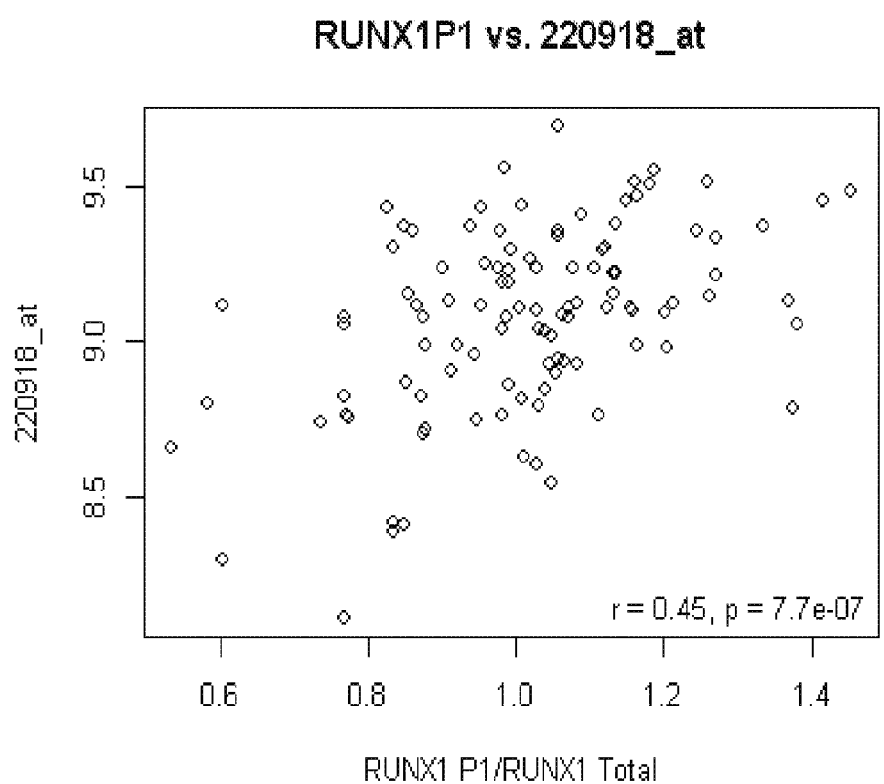
Figure 12:
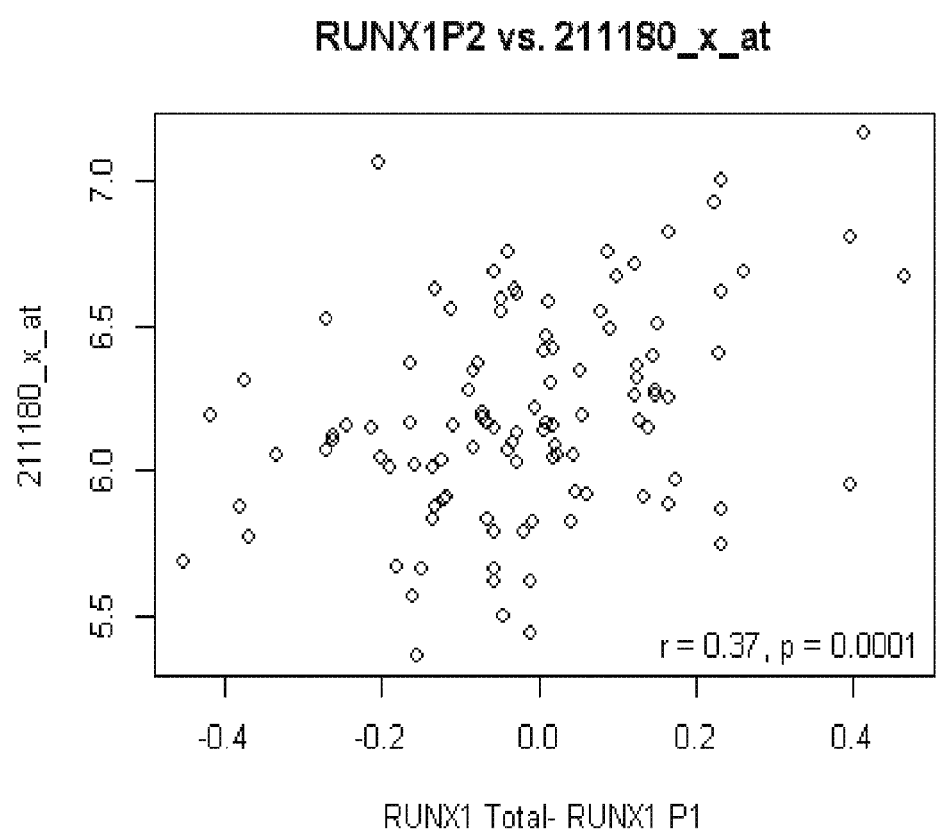
Figure 12:
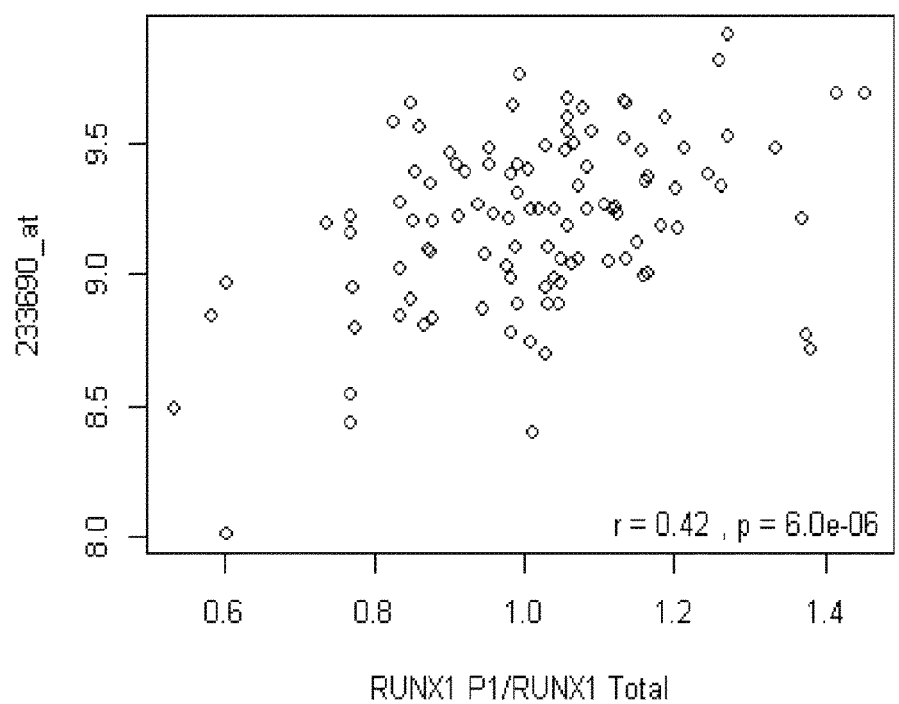
Figure 12:
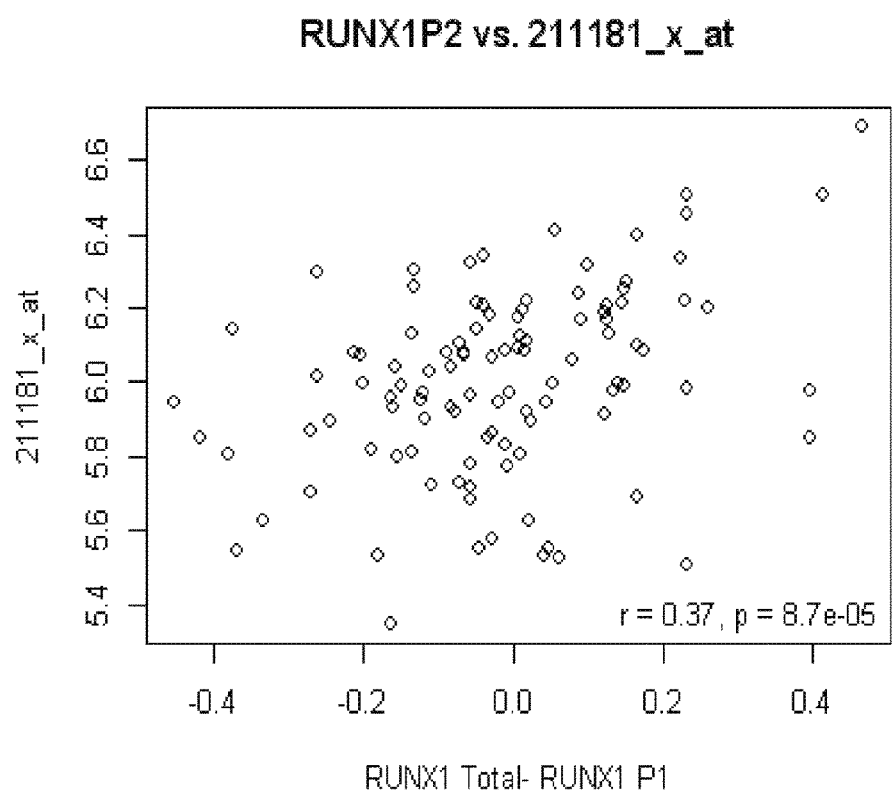

RUNX1 probe sets reflect P1-specific vs. non-specific RUNX1 derived transcripts. To confirm that the 12 RUNX1 probe sets indeed represent distinct sets of transcripts, a clustering analysis was begun using the 12 RUNX1 transcripts and the healthy volunteer and CATHGEN microarray datasets (FIG. 12). Hierarchical clustering was used to reorder probe sets (rows) and samples (columns) in each dataset. Gene expression values were centered and scaled by rows and colored to reflect higher vs. lower gene expression. Across all 4 datasets, three probe sets (233690_at, 220918_at, and 209360_s_at) consistently clustered together (lower cluster in each heatmap) and map to P1 derived RUNX1 transcripts. The remaining nine probe sets formed a separate distinct cluster (upper cluster in each heatmap) and likely represent P2 derived RUNX1 transcription. Additionally, in the pre- and post-aspirin datasets, the samples (columns) cluster into two distinct clusters: those with high P2 expression/low P1 expression or low P2 expression/high P1 expression.

To test the hypothesis that the two clusters of probe sets represent RUNX1 transcription from the two different promoters, we correlated probe set expression with the relative quantity of P1 vs. P2 derived transcripts. We observed that the probe set expression of 220918_at and 233690_at were significantly correlated with P1 relative expression while the majority of the probe sets in the remaining cluster were significantly correlated with P2 relative expression. (FIG. 12B) Therefore, for the remainder of the manuscript we refer to 220918_at, 233690_at, and 209360_s_at probe sets as P1-derived RUNX1 transcripts and the remaining nine probe sets representing P2-derived RUNX1 transcripts.

Statistical Analysis.

The projection of Factor 14 into various microarray datasets were performed as described in "Factor Projection" section of Example 3.

RT-PCR Summary:

RNA was extracted from peripheral blood derived platelets using the miRvana miRNA Isolation Kit (Life Technologies) with acid-phenol chloroform (Life Technologies) separation. Due to the low concentration of available platelet RNA, concentration and integrity were assessed using the Agilent 2100 Bioanalyzer Pico chips (Agilent Technologies; Santa Clara, Calif.). The concentration was too low for accurate determination via standard spectrophotometric methods and for the Agilent Pico RIN algorithm to accurately determine a RIN quality score. As a result, quality was assessed by visualization of the Bioanalyzer lane curve. RNA samples with obvious 18S and 28S peaks, minimal degradation "noise" between peaks, and no large aberrant peaks above or below the 18S and 28S bands were selected for further analysis.

cDNA was synthesized using SuperScript VILO Master Mix (Life Technologies) according to the manufacturer's recommended protocol in 20 µl reactions using 15 ng of RNA, generating a final cDNA concentration of 0.75 ng/µl. Real-Time PCR was performed using 20 µl (15 ng) of cDNA, 30 µl of RNase/DNase free water, and 50 µl of TaqMan Gene Expression Master Mix (Life Technologies) per TLDA well. The TLDA cards were centrifuged, sealed, and assayed using the ViiA7 Real-Time Detection System (Life Technologies). GeNorm analysis was performed on the resulting data to determine the most stable set of reference targets for normalization. The geometric mean of the most stable reference assays (ACTB, GAPDH) was used as the normalization control for downstream ΔCq analysis.

An additional quality assessment step was added due to PCR efficiency variation in some post-reaction PCR amplification curves. A subset of samples demonstrated aberrant amplification curves (efficiency) when compared to the majority, which was likely due to low input RNA concentration or quality, and was discarded. This subjective quality control step was based upon visual inspection of the shape and consistency of amplification curves (ARn vs Cycle), and was performed completely blinded to the identity and group assignment of each sample.

Platelet RT-PCR Methodology

RNA Analysis and Quality Control

RNA was extracted from peripheral blood derived platelets using the miRvana miRNA Isolation Kit (Life Technologies) with acid-phenol chloroform (Life Technologies) separation. MicroRNA and mRNA were collected in the same elution. Platelet protein was separated from nucleic acids prior to RNA extraction.

Figure 22:
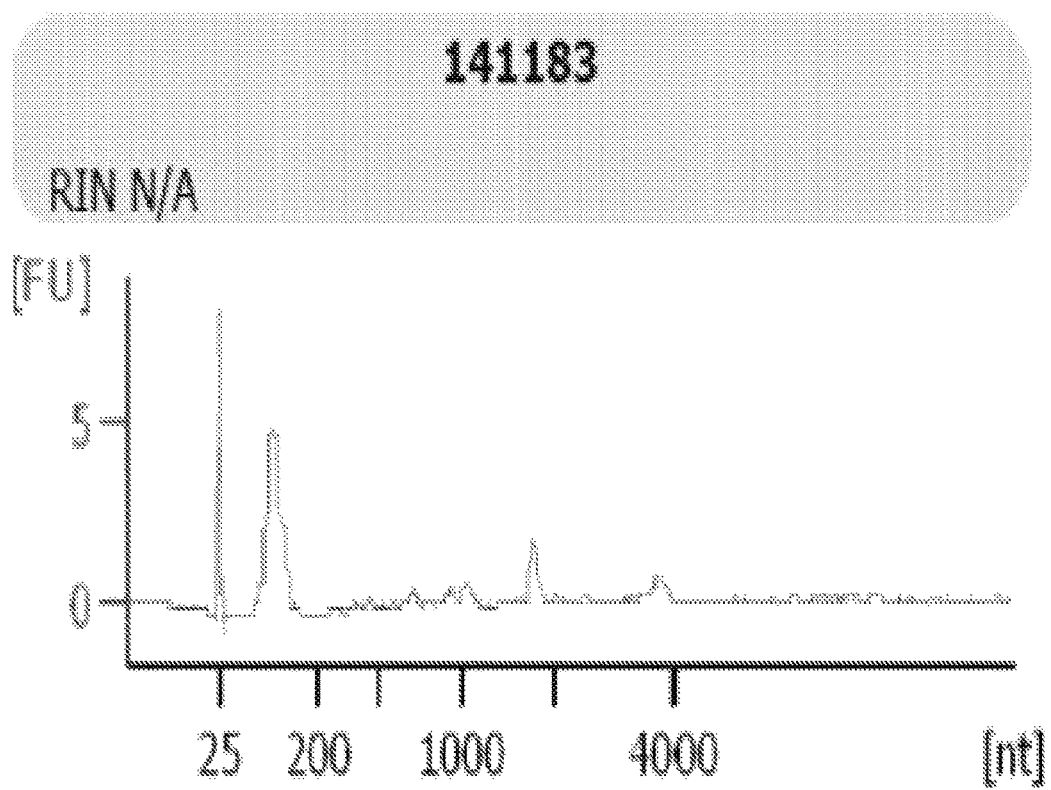
FIG. 22 shows examples of (A) accepted and (B) rejected RNAs based on Bioanalyzer microfluidic gel traces.
Figure 22:
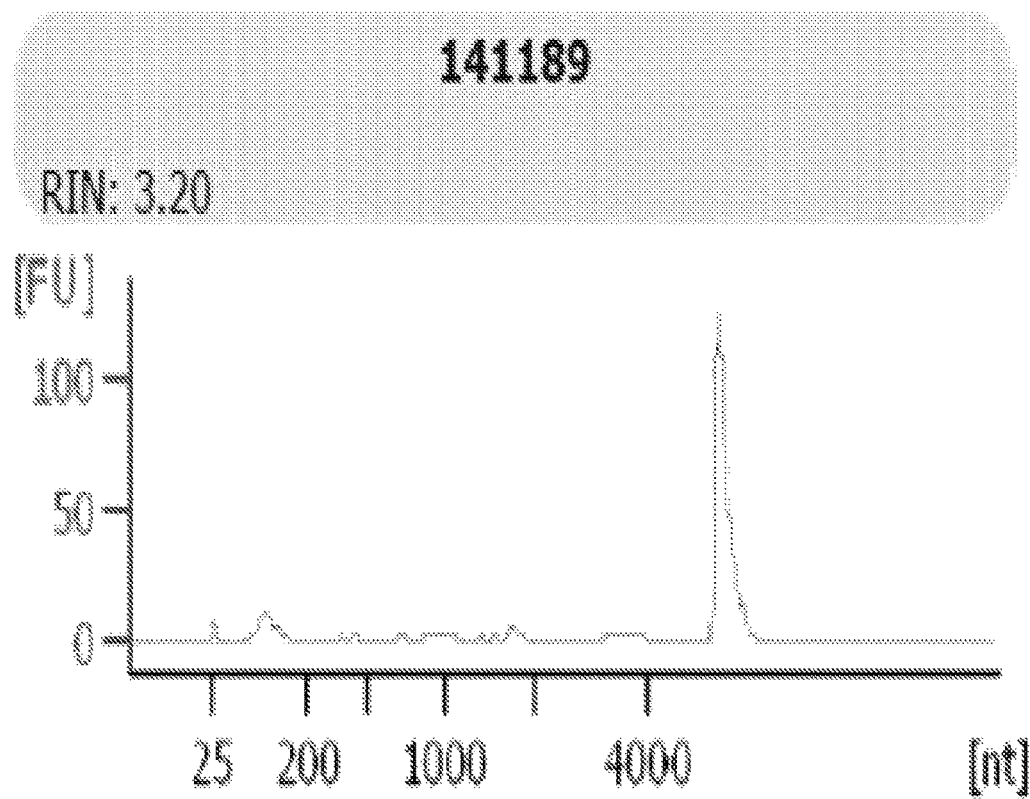

Concentration and integrity of available platelet RNA were assessed using Agilent 2100 Bioanalyzer Pico chips (Agilent Technologies; Santa Clara, Calif.). The concentration was too low for accurate determination via standard spectrophotometric methods, and for the Agilent Pico RIN algorithm to determine an accurate RIN quality score. As a result, quality was assessed by visualization of the Bioanalyzer trace. See FIG. 22; Table 20. RNA samples with obvious 18S and 28S peaks, minimal degradation between peaks, and no large aberrant peaks above the 18S and 28S bands were selected for further analysis. Visual RNA quality assessments were performed blinded to the identity and group assignment of each sample.

TABLE 20

Basic statistical summary of RNA concentration in available platelet RNA samples

| n = 100 | Mean | SD | Max | Min |
| --- | --- | --- | --- | --- |
| Conc. [ng/µl] | 6.6 | 3.67 | 23.33 | 1.34 | cDNA was synthesized using SuperScript VILO Master Mix (Life Technologies) according to the manufacturer's recommended protocol in 20 µl reactions using 15 ng of RNA, generating a final cDNA concentration of 0.75 ng/µl. Aliquots from samples with an initial RNA concentration of >7.5 ng/µl were diluted with RNase-free water prior to plating of cDNA synthesis reactions.

A loading test plate was run using 4 samples; 2 from each experimental group. These samples were loaded at 50 ng and 15 ng of cDNA per TLDA well each. This test plate was used to estimate the most desirable loading amount of cDNA in the final experiment. Optimal loading would result in expression of our lowest targets of interest resulting in Cq values<35, abundant transcripts>18 and a minimal loss of low quantity samples to high RNA loading requirements. The data from this test plate and the number of samples lacking a minimum of 50 ng of RNA predicated that we use 15 ng of cDNA per TLDA well in the subsequent experimentation. Table 21.

TABLE 21

TLDA Assay and Target of Interest list for Platelet analysis Platelet TaqMan Array Card

| TaqMan Assay | Target Transcript |
| --- | --- |
| Hs00257856_s1 | RUNX1 |
| Hs01021966_m1 | RUNX1 |

TABLE 21-continued

TLDA Assay and Target of Interest list for Platelet analysis Platelet TaqMan Array Card

| TaqMan Assay | Target Transcript |
| --- | --- |
| Hs01021967_m1 | RUNX1 |
| Hs01021970_m1 | RUNX1 |
| Hs04186042_m1 | RUNX1 |

Real-Time PCR was performed using 20 µl (15 ng) of cDNA, 30 µl of RNase/DNase free water, and 50 µl of TaqMan Gene Expression Master Mix (Life Technologies) per TLDA well. The TLDA cards were centrifuged, sealed, and assayed using the ViiA7 Real-Time Detection System (Life Technologies). PCR thermal cycling parameters were the same as those used in the Whole Blood experiment and match the recommended protocol for TLDA card studies. GeNorm analysis was performed on the resulting data to determine the most stable set of reference targets for normalization. The geometric mean of the most stable reference assays (ACTB, GAPDH) was used as the normalization control for downstream ΔCq analysis. Table 22.

TABLE 22

Stability M-scores of reference assays used to normalize Platelet TLDA data

| Assay | Transcript | M |
| --- | --- | --- |
| Hs99999903_m1 | ACTB | 0.41 |
| Hs99999905_m1 | GAPDH | 0.41 |

An additional quality assessment step was added due to PCR efficiency variation in some post-reaction PCR amplification curves. A subset of samples demonstrated aberrant amplification curves (efficiency) when compared to the majority, likely due to low input RNA concentration or quality, and was discarded. This subjective quality control step was based upon visual inspection of the shape and consistency of amplification curves (ΔRn vs Cycle), and was performed blinded to the identity and group assignment of each sample.

Real-Time Statminer Analysis of all Real-Time PCR Data.

Data exported form the ViiA7 was formatted for import into Real-Time Statminer Analysis software (Integromics; Madison, Wis.). This software provided a pipeline for rapid analysis of the total set of Real-Time PCR data generated in this study. Data were normalized based on the geometric mean of the most stable set of reference targets as determined by the GeNorm stability analysis algorithm in Statminer. This normalization was used to generate tables of Cq, ΔCq, and ΔΔCq values used in more advanced analysis.

Results: Correlation of RUNX1 Transcripts with Factor 14 Expression

RUNX1 may regulate a number of individual genes represented by Factor 14. RUNX1 transcripts may correlate with the aggregate expression of the genes represented by Factor 14. Prior to the administration of aspirin, only 208129_x_at, a P2-specific RUNX1 probe set, was associated with Factor 14 expression. (Table 23, pre-aspirin) However after the administration of aspirin, there was a significant strengthening of the association of the majority of RUNX1 probe sets with Factor 14 expression (Table 23, post-aspirin), such that the P2 RUNX1 probe sets were positively correlated with Factor 14 expression on aspirin while the P1 probe sets were inversely correlated with Factor 14 expression. To confirm the directionality of the P1-vs. non-specific RUNX1 probe set correlations, the CATHGEN patient cohort datasets were used. In both cohorts, we found that the P1-derived probe sets were inversely correlated with F14 expression while the P2-derived RUNX1 probe sets were positively correlated with F14 expression. (Table 23, observational and case control cohorts). Therefore, in general, higher expression levels of P2 RUNX1 expression are associated with higher Factor 14 expression, while higher P1 derived transcripts are associated with lower Factor 14 expression. Aspirin exposure strengthens these relationships.

TABLE 23

RUNX1 transcripts are associated with Factor 14 expression, primarily after aspirin exposure

| RUNX1 Probe set | Healthy Volunteer Cohort | | Observational cohort | Case control cohort |
| --- | --- | --- | --- | --- |
| | Pre-aspirin correlation | Post-aspirin correlation | | |
| P2 derived RUNX1 transcripts | | | | |
| 208129_x_at | 0.34* | 0.60*** | 0.16* | 0.20*** |
| 209359_x_at | 0.22 | 0.53*** | 0.14* | 0.19 |
| 210365_at | −0.01 | 0.39** | 0.25** | 0.13* |
| 210805_x_at | −0.11 | 0.42** | 0.09 | 0.23*** |
| 211179_at | 0.16 | 0.11 | 0.16* | 0.12* |
| 211180_x_at | 0.23 | 0.55*** | 0.11 | 0.16** |
| 211181_x_at | −0.07 | 0.65*** | 0.21** | 0.23*** |
| 211182_x_at | 0.01 | 0.44** | 0.28*** | 0.26**** |
| 217263_x_at | −0.11 | 0.39** | 0.17* | 0.10* |
| P1 derived RUNX1 transcripts | | | | |
| 209360_s_at | 0.10 | −0.24* | −0.34*** | −0.33**** |
| 233690_at | −0.15 | −0.05 | −0.26** | −0.28**** |
| 220918_at | −0.03 | −0.45** | −0.35*** | −0.30**** |

*$p < 0.05$,
**$p < 0.01$,
***$p < 1E-04$,
****$p < 1E-07$

Because of the apparent strengthening of the relationship between RUNX1 and Factor 14 expression on aspirin, aspirin-induced changes in RUNX1 may correlate with change in Factor 14 expression. The change in the P2 RUNX1 probe set expression was highly correlated with the change in Factor 14 expression after aspirin exposure (Table 24, P2 derived transcripts). Furthermore, the change in P1 derived transcripts was inversely correlated with the change in Factor 14 expression (Table 24, P1 derived transcripts). These observations demonstrate that aspirin exposure is associated with changes in P1 and P2 RUNX1 expression levels, which are, respectively, associated with opposing effects on Factor 14 expression.

TABLE 24

Aspirin exposure results in changes in RUNX1 expression that correlate with changes in Factor 14 expression.

| Probe set | Correlation of changes in expression |
| --- | --- |
| P2-derived RUNX1 transcripts | |
| 208129_x_at | 0.60**** |
| 209359_x_at | 0.65**** |
| 210365_at | 0.30* |

TABLE 24-continued

Aspirin exposure results in changes in RUNX1 expression that correlate with changes in Factor 14 expression.

| Probe set | Correlation of changes in expression |
| --- | --- |
| 210805_x_at | 0.38** |
| 211179_at | −0.16 |
| 211180_x_at | 0.67**** |
| 211181_x_at | 0.57*** |
| 211182_x_at | 0.49** |
| 217263_x_at | 0.35* |
| P1-derived RUNX1 transcripts | |
| 209360_s_at | −0.11 |
| 233690_at | 0.13 |
| 220918_at | −0.27* |

*$p < 0.05$,
**$p < 0.01$,
***$p < 1E-04$,
****$p < 1E-06$

Example 8

Changes in RUNX1 Expression in Response to Aspirin Exposure

Visualization of the heatmap data suggested that not only are P1 and P2 RUNX1 probe sets clustered together, but also that within an individual (columns, FIG. 12, pre- and post-aspirin datasets) the P1 transcripts are inversely correlated with total RUNX1 expression levels. It was hypothesized that the P1 and P2 derived transcripts are regulated in a coordinated, inverse manner.

To test this hypothesis, the influence of aspirin exposure on the change in P1 vs. P2 RUNX1 probe set expression was assessed. Whole blood RNA from before and after aspirin exposure in healthy volunteers was analyzed by microarray analysis. Based on the pair-wise correlations in changes in P1 vs. P2 expression with aspirin exposure (Table 25), the correlation between the change in 211181_x_at and 209360_s_at probe sets for visualization were selected. The change (post-pre) in 211181_x_at expression with aspirin exposure is plotted on the y-axis and the change in 209360_s_at expression is plotted on the x-axis. The correlation and p-value of the changes in gene expression is depicted. The dotted horizontal and vertical lines represent no change in gene expression, while positive values represent upregulation, and negative values represent downregulation with aspirin exposure. The negative correlation between the change in P1 vs. P2 RUNX1 transcripts demonstrates that aspirin exposure leads to complementary changes in gene expression such that an up (or down) regulation of the P1 transcript is associated with a change in the opposite direction of the P2 transcript.

TABLE 25

RUNX1 P1 derived transcripts change in opposite directions compared
to P2 derived transcripts in response to aspirin exposure*

| Probe set ID | 208129_x_at | 209359_x_at | 210365_at | 210805_x_at | 211179_at | 211180_x_at | 211181_x_at |
|---|---|---|---|---|---|---|---|
| 208129_x_at |  | 2.00E−10 | 8.27E−02 | 3.36E−01 | 5.79E−01 | 5.98E−10 | 1.39E−06 |
| 209359_x_at | 0.74 |  | 1.15E−01 | 6.17E−03 | 9.25E−01 | 3.83E−11 | 2.38E−05 |
| 210365_at | 0.24 | 0.22 |  | 6.83E−01 | 5.57E−01 | 2.16E−02 | 7.80E−03 |
| 210805_x_at | 0.13 | 0.37 | 0.06 |  | 3.90E−01 | 2.58E−02 | 3.60E−03 |
| 211179_at | 0.08 | 0.01 | −0.08 | −0.12 |  | 9.18E−01 | 9.31E−01 |
| 211180_x_at | 0.73 | 0.76 | 0.32 | 0.31 | 0.01 |  | 4.25E−06 |
| 211181_x_at | 0.61 | 0.55 | 0.36 | 0.39 | 0.01 | 0.58 |  |
| 211182_x_at | 0.33 | 0.35 | 0.09 | 0.27 | −0.03 | 0.37 | 0.50 |
| 217263_x_at | 0.18 | 0.19 | 0.36 | 0.27 | −0.08 | 0.32 | 0.47 |
|  |  |  | P2 transcripts |  |  |  |  |
| 209360_s_at | −0.16 | −0.05 | −0.05 | −0.08 | −0.20 | −0.18 | −0.44 |
| 233690_at | −0.13 | −0.04 | 0.30 | −0.05 | −0.17 | 0.04 | −0.12 |
| 220918_at | −0.40 | −0.28 | −0.03 | −0.24 | −0.23 | −0.30 | −0.36 |

| Probe set ID | 211182_x_at | 217263_x_at |  | 209360_s_at | 233690_at | 220918_at |
|---|---|---|---|---|---|---|
| 208129_x_at | 1.52E−02 | 1.87E−01 | P2 transcripts | 2.48E−01 | 3.57E−01 | 2.72E−03 |
| 209359_x_at | 1.02E−02 | 1.67E−01 |  | 7.47E−01 | 7.93E−01 | 4.03E−02 |
| 210365_at | 5.27E−01 | 7.38E−03 |  | 7.32E−01 | 3.17E−02 | 8.39E−01 |
| 210805_x_at | 5.25E−02 | 5.08E−02 |  | 5.66E−01 | 7.38E−01 | 8.93E−02 |
| 211179_at | 8.52E−01 | 5.86E−01 |  | 1.53E−01 | 2.19E−01 | 9.93E−02 |
| 211180_x_at | 6.24E−03 | 2.00E−02 |  | 1.92E−01 | 7.56E−01 | 2.85E−02 |
| 211181_x_at | 1.35E−04 | 3.91E−04 |  | 1.04E−03 | 4.06E−01 | 9.05E−03 |
| 211182_x_at |  | 4.76E−02 |  | 2.45E−03 | 2.62E−01 | 3.36E−03 |
| 217263_x_at | 0.27 |  |  | 3.82E−02 | 1.18E−01 | 5.28E−01 |
|  | P2 transcripts |  |  |  | P1 transcripts |  |
| 209360_s_at | −0.41 | −0.29 | P1 transcripts |  | 1.60E−02 | 1.31E−01 |
| 233690_at | −0.16 | 0.22 |  | 0.33 |  | 1.20E−06 |
| 220918_at | −0.40 | 0.09 |  | 0.21 | 0.61 |  |

*Changes in RUNX1 transcripts with aspirin exposure were correlated with each other using Pearson correlation for the P1 and P2 transcripts. Pearson correlation coefficients for the change in expression for each pair of transcripts are given below the diagonal with corresponding p-values above the diagonal. Significant correlations are bolded.

Figure 13:
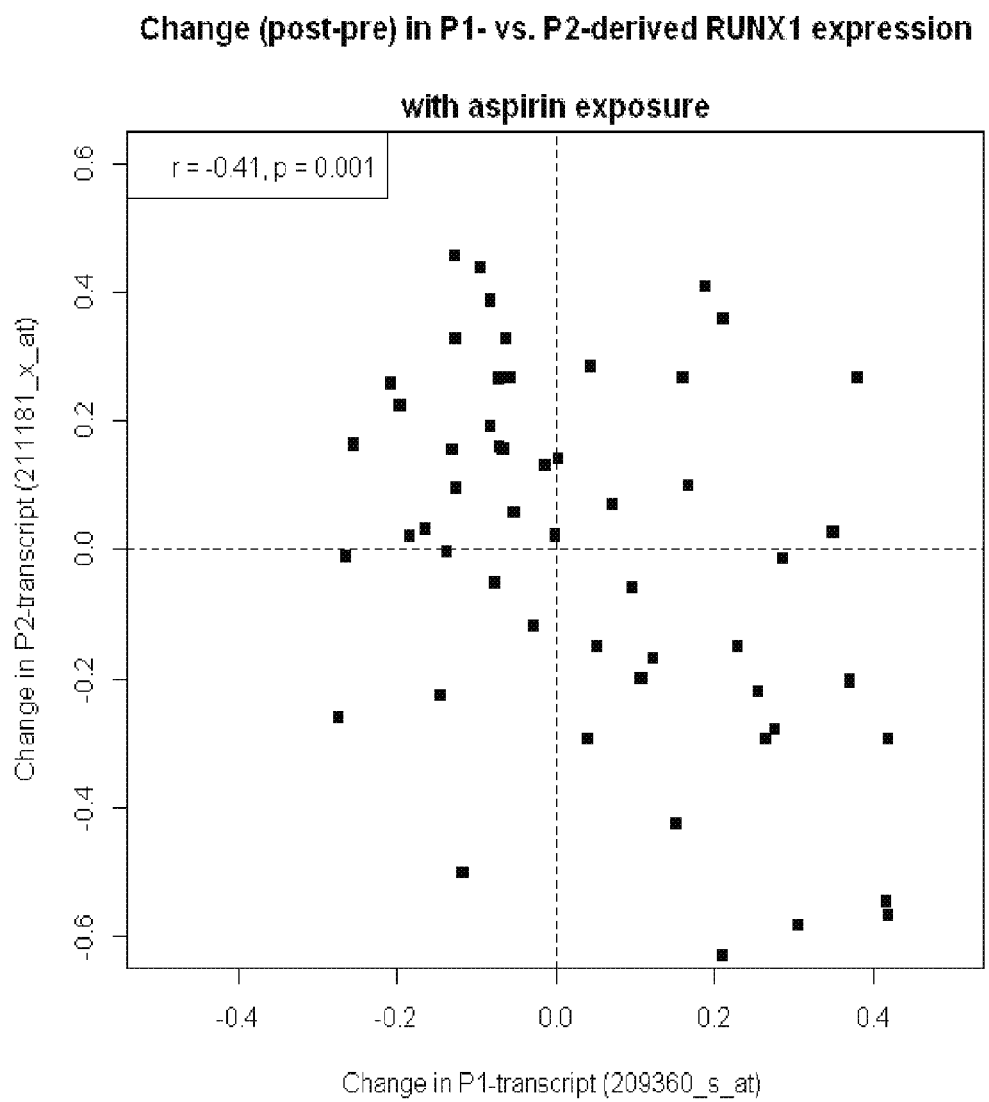
FIG. 13 shows that aspirin exposure was associated with opposing changes in P1 vs. P2 RUNX1 gene expression in whole blood RNA.

The change in P1 transcripts was correlated with the change in P2 RUNX1 probe set expression after aspirin exposure and it was found that the magnitude of change in P1 derived transcripts was inversely correlated with the magnitude of change in the P2 RUNX1 derived transcripts (Table 25). FIG. 13 demonstrates the P1 and P2 probe sets with the strongest, inverse correlation in change in expression with aspirin exposure. Therefore, aspirin exposure is associated with changes RUNX1 gene expression such that changes in P1 derived transcripts associated by changes (in the opposite direction) of P2 RUNX1 derived transcripts.

As shown in Example 2, the majority of the Factor 14 transcripts are of platelet origin. Although platelets are anucleate, they contain genomic material that may be remnants of thrombopoeisis. Purified platelets contain both the P1 and P2 derived RUNX1 transcripts based on publically available RNA-seq data. Based on the microarray data from whole blood RNA (FIG. 13), changes in RUNX1 transcripts in whole blood may be mirrored in platelet RNA. Purified platelet RNA was obtained from before and after aspirin exposure in the healthy volunteer cohort and the change in RUNX1 P1 transcripts was compared to the change in P2 RUNX1 transcripts using RT-PCR. Compared to total RUNX1 transcript levels, aspirin exposure was associated with larger magnitude changes in P1 RUNX1 expression (FIG. 13—x-axis vs. y-axis scales).

Figure 14:
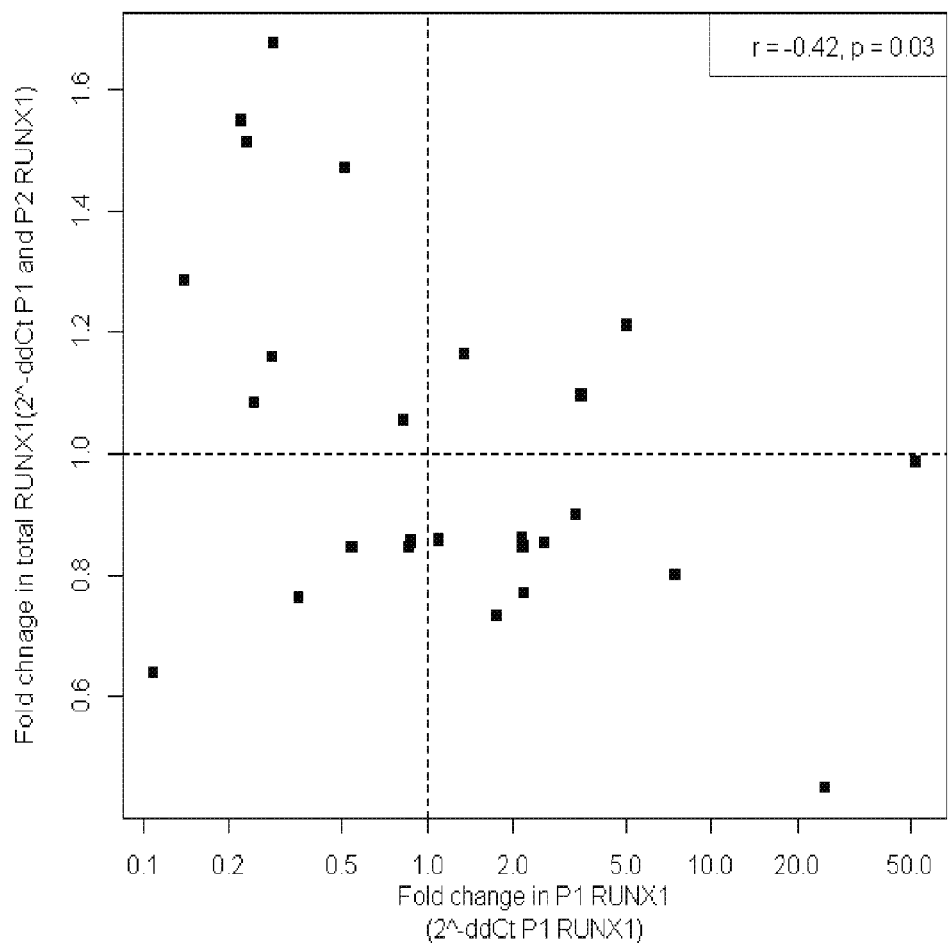
FIG. 14 shows that aspirin exposure was associated with opposing changes in P1 RUNX1 gene expression in platelet RNA.
Figure 14:
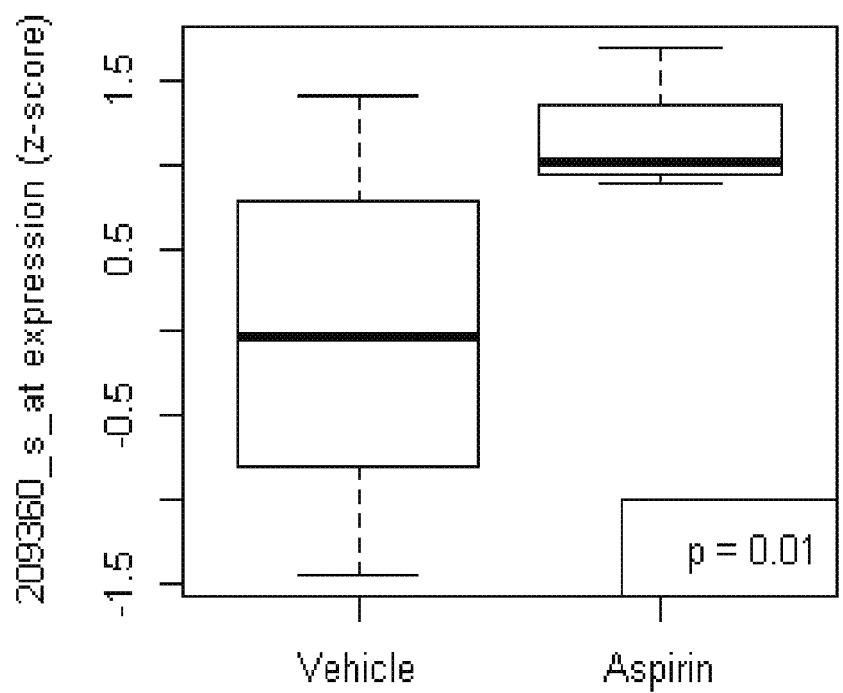
Figure 14:
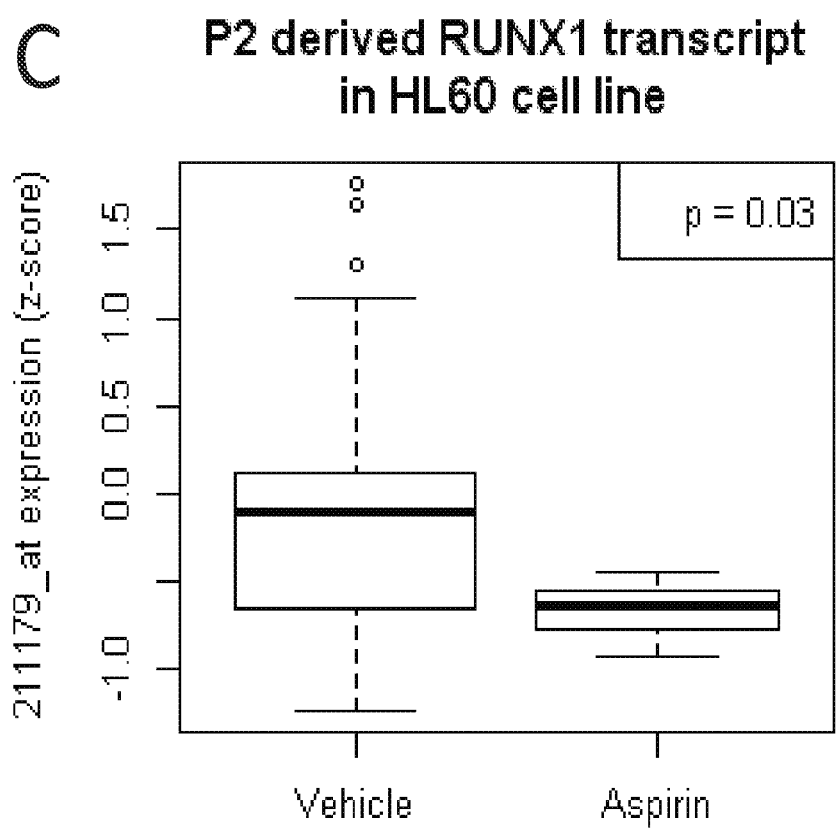
Figure 14:
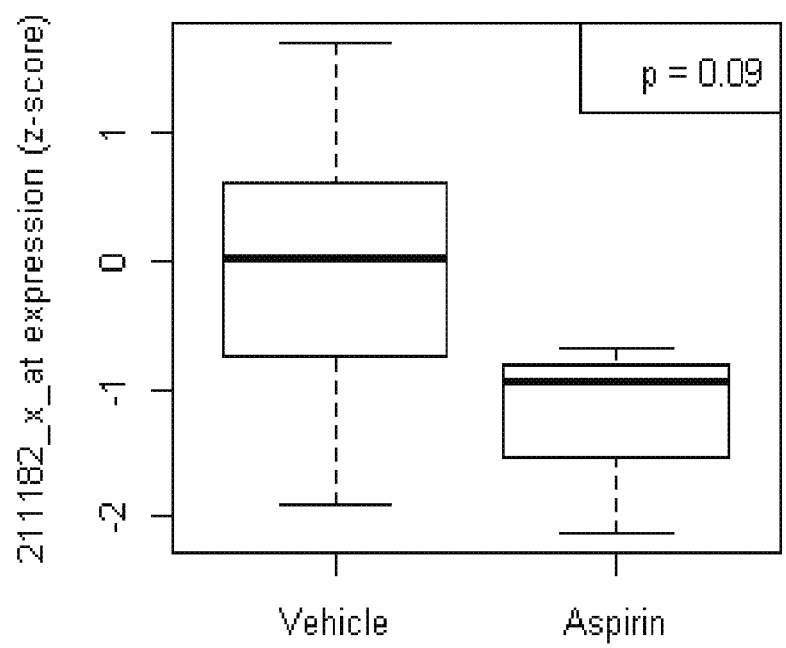

Furthermore, as in whole blood changes in P1 expression were associated with opposing changes in total RUNX1 expression (FIG. 14). Purified platelet RNA was obtained from a subset of healthy volunteers from before and after aspirin exposure and analyzed by RT-PCR. Changes in gene expression with aspirin exposure for RUNX1 P1-specific transcripts (x-axis) were correlated with the change in total RUNX1 gene expression (y-axis). Dotted horizontal and vertical lines represent no change; values greater than 1.0 represent down regulation while those less than 1.0 represent upregulation. The Pearson correlation coefficient and p-value is depicted. Aspirin exposure resulted in minimal changes in total RUNX1 gene expression, while the change in P1 transcripts was highly variable such that aspirin exposure resulted in up to a 5-fold up (or down) regulation in P1 RUNX1 expression. Further the inverse correlation between changes in P1 vs. total RUNX1 transcript suggests that an upregulation in P1 transcription with aspirin exposure is accompanied by a downregulation in P2 derived transcription. Therefore, the changes in RUNX1 expression using whole blood RNA are mirrored in platelet RNA.

Example 9

RUNX1 Transcripts are Associated with Platelet Function Before and after Aspirin Exposure Because Factor 14 genes were identified through their association with platelet function, we next tested the hypothesis that RUNX1 transcripts were associated with platelet function before and after aspirin exposure. Prior to the administration of aspirin a P2 RUNX1 probe set (208129_x_at) was correlated with higher levels of platelet function which determined using the platelet function score (PFS) as described in Example 1. (Table 26, pre-aspirin correlation). Therefore, prior to the administration of aspirin, higher RUNX1 expression, which is correlated with higher Factor 14 expression (Table 23, pre-aspirin), is also associated with higher levels of platelet function.

TABLE 26

Correlation of RUNX1 probes with platelet function before and after aspirin exposure

| Probe Set ID | Pre-aspirin correlation | Post-aspirin correlation |
|---|---|---|
| P2 derived RUNX1 transcripts | | |
| 208129_x_at | 0.34** | −0.26* |
| 209359_x_at | 0.22 | −0.16 |
| 210365_at | −0.01 | −0.07 |
| 210805_x_at | −0.11 | −0.05 |
| 211179_at | 0.16 | −0.08 |
| 211180_x_at | 0.23 | −0.32* |
| 211181_x_at | −0.07 | −0.40** |
| 211182_x_at | 0.01 | −0.08 |
| 217263_x_at | −0.11 | −0.13 |
| P1 derived RUNX1 transcripts | | |
| 209360_s_at | 0.10 | 0.26* |
| 233690_at | −0.15 | 0.10 |
| 220918_at | −0.03 | 0.34** |

*p = 0.06,
**p ≤ 0.01,

After aspirin exposure, however, several RUNX1 probe sets were associated with platelet function (Table 26, post-aspirin) such that the P2 RUNX1 probe set expression was now inversely correlated with platelet function. The change in the direction of association for the total RUNX1 derived transcripts before vs. after aspirin exposure (Table 26, pre vs. post-aspirin) and the prior observations that aspirin changes RUNX1 expression taken together suggest that the role of aspirin is to lower platelet function via changes in RUNX1 and Factor 14 expression. Further, we again observed opposing effects of the P1 derived transcripts when compared to the P2 RUNX1 probe sets (Table 26). When compared to P2 RUNX1 transcripts, the P1 derived RUNX1 transcripts have opposing influences not only on gene expression, but also platelet function.

Example 10

In Vitro Aspirin Exposure Changes RUNX1 Expression

Based on our in vivo human data following aspirin exposure, similar changes in RUNX1 expression may occur in vitro. Using publically available microarray data in a human promyelocytic cell line (HL60), the hypothesis was tested that in vitro aspirin exposure would change RUNX1 probe set expression. Compared to vehicle-only control, aspirin exposure decreased the expression of two P2 RUNX1 probe sets and increased the expression of a P1-specific probe set. (FIG. 14B-14D) The remaining RUNX1 probe sets did not change in response to aspirin in this system. Therefore, as in our in vivo healthy volunteer data, aspirin exposure in vitro changes RUNX1 gene expression with again opposing effects on the P1-derived vs. P2 transcript levels.

Example 11

Association of RUNX1 Transcripts with Long-Term Clinical Outcomes

The previous examples established that higher levels of Factor 14 genes are correlated with a higher risk of long-term clinical outcomes in patients with cardiovascular disease. Having established that RUNX1 transcripts are aspirin responsive transcripts in vivo and in vitro (Tables 24 and 25 and FIGS. 13 and 14), it was hypothesized that RUNX1 transcripts would be associated with clinical outcomes. Because of the consistent, opposing effects of the P1 vs. P2 RUNX1 probe set associations with Factor 14 expression, platelet function, and in vivo and in vitro response to aspirin exposure, it was further hypothesized that the P1 derived transcripts would be protective for death/MI while the P2 levels of RUNX1 would be a risk factor.

Using previously defined biorepository of patients with whole blood RNA microarray data at the time of cardiac catheterization and long-term follow up for death and myocardial infarction (MI), the case-control and observational patient cohorts were assembled. The associations of P1 (unshaded) and P2 (shaded) RUNX1 probe sets with death/MI in the case-control cohort (odds ratios, A) or the observational cohort (hazard ratios, B) are plotted as barplots. The p-values for each transcript are depicted within each bar. NS=nonsignificant. The P1 RUNX1 transcripts are protective for death/MI while the P2 transcripts are risk factors for death/MI.

Figure 15:
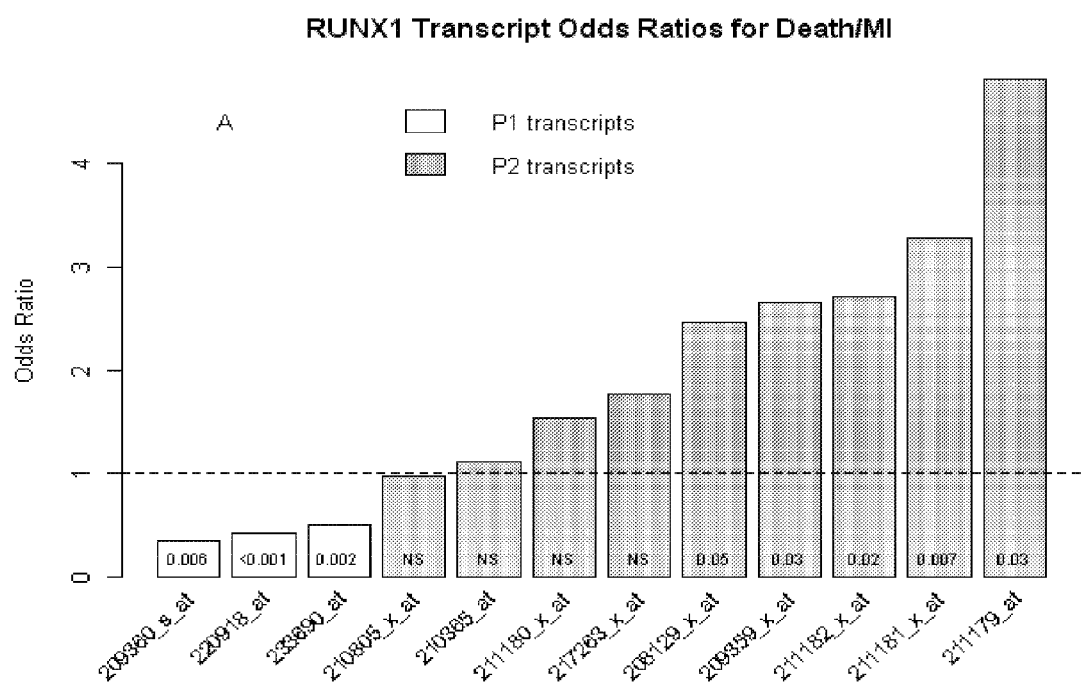
FIG. 15 shows that P1 vs. P2 RUNX1 transcripts were associated with the risk of death or myocardial infarction in opposing directions.
Figure 15:
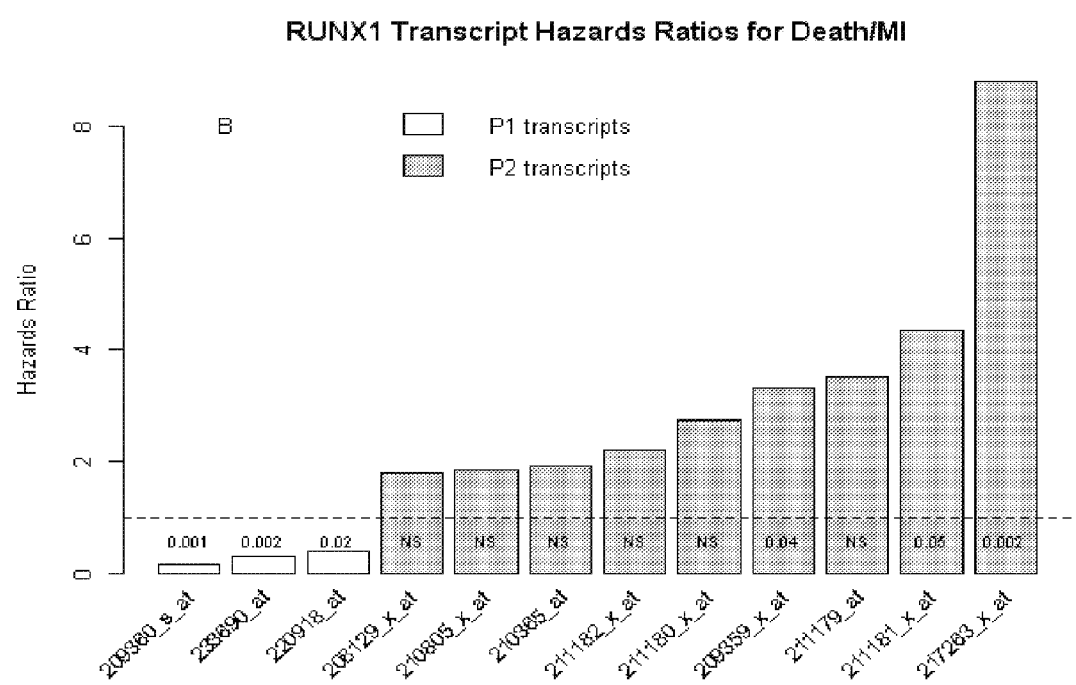

In both the case-control and observational cohorts, the P1-derived transcripts were indeed protective for death/MI, while the total levels of RUNX1 were risk factors for the outcome of death/MI. (FIG. 15). Therefore measurement of RUNX1 transcripts in whole blood RNA is a promising prognostic biomarker for patients with cardiovascular disease.

Cutoffs were determined by analyzing the change in gene expression pre-vs. post aspirin by RT-PCR in healthy volunteers. Table 27. The median value for those individuals who demonstrated a reduction in gene expression in response to aspirin was used to define the cutoff for each gene. Proposed reduction in gene expression cutoff expressed as absolute change for ARS and fold-change for individual transcripts. Similar cutoffs may be constructed using alternative methodologies for quantifying gene expression such as microarray or RNA-sequencing.

TABLE 27

Proposed cutoff values for reduction in gene expression with aspirin exposure to identify individuals with a favorable response to aspirin.

| Gene Symbol | Gene Description | Cutoff Values |
|---|---|---|
| ARS | Aggregate expression of 64-gene set signature | 1.6 |
| Individual components of ARS measured by RT-PCR | | |
| ALOX12 | arachidonate 12-lipoxygenase | 1.538 |
| ARHGAP6 | Rho GTPase activating protein 18 | 1.724 |
| CALD1 | caldesmon 1 | 1.26 |
| CDC14B | cell division cycle 14B | 1.474 |
| CLU | Clusterin | 1.854 |
| CMTM5 | CKLF-like MARVEL transmembrane domain containing 5 | 1.429 |
| CPNE5 | copine V | 1.879 |
| CTDSPL | CTD (carboxy-terminal domain, RNA polymerase II, polypeptide A) small phosphatase-like | 1.495 |
| CTTN | Cortactin | 1.443 |
| ELOVL7 | ELOVL family member 7, elongation of long chain fatty acids (yeast) | 1.384 |
| FRMD3 | FERM domain containing 3 | 1.35 |
| FSTL1 | follistatin-like 1 | 1.748 |
| GNG11 | guanine nucleotide binding protein (G protein), gamma 11 | 1.383 |
| GP1BB | glycoprotein Ib (platelet), beta polypeptide | 1.432 |
| GUCY1B3 | guanylate cyclase 1, soluble, beta 3 | 1.551 |

TABLE 27-continued

Proposed cutoff values for reduction in gene expression with aspirin exposure to identify individuals with a favorable response to aspirin.

| Gene Symbol | Gene Description | Cutoff Values |
|---|---|---|
| IGF2BP3 | insulin-like growth factor 2 mRNA binding protein 3 | 1.347 |
| ITGA2B | integrin, alpha 2b (platelet glycoprotein IIb of IIb/IIIa complex, antigen CD41) | 1.663 |
| ITGB3 | integrin, beta 3 (platelet glycoprotein IIIa, antigen CD61) | 1.883 |
| MMD | monocyte to macrophage differentiation-associated | 1.29 |
| MPL | myeloproliferative leukemia virus oncogene | 1.883 |
| MYL9 | myosin, light chain 9, regulatory | 1.543 |
| MYLK | myosin, light chain kinase | 1.525 |
| PBX1 | pre-B-cell leukemia transcription factor 1 | 1.464 |
| PCSK6 | proprotein convertase subtilisin/kexin type 6 | 1.805 |
| PDE5A | phosphodiesterase 5A, cGMP-specific | 1.485 |
| PF4 | platelet factor 4 (chemokine (C—X—C motif) ligand 4) | 1.416 |
| PPBP | pro-platelet basic protein (chemokine (C—X—C motif) ligand 7) | 1.467 |
| PRKAR2B | protein kinase, cAMP-dependent, regulatory, type II, beta | 1.346 |
| RUNX1 | Runt-related transcription factor 1 | 1.331 |
| SDPR | serum deprivation response (phosphatidylserine binding protein) | 1.732 |
| SELP | selectin P (granule membrane protein 140 kDa, antigen CD62) | 1.543 |
| SH3BGRL2 | SH3 domain binding glutamic acid-rich protein like 2 | 1.44 |
| SLC24A3 | solute carrier family 24 (sodium/potassium/calcium exchanger), member 3 | 1.315 |
| SPARC | secreted protein, acidic, cysteine-rich (osteonectin) | 1.393 |
| TGFB1I1 | transforming growth factor beta 1 induced transcript 1 | 1.645 |
| THBS1 | thrombospondin 1 | 1.649 |
| TREML1 | triggering receptor expressed on myeloid cells-like 1 | 1.258 |
| TTC7B | tetratricopeptide repeat domain 7B | 1.348 |
| TUBB1 | tubulin, beta 1 | 1.287 |
| ALOX12 | arachidonate 12-lipoxygenase | 1.538 |
| ARHGAP6 | Rho GTPase activating protein 18 | 1.724 |
| CALD1 | caldesmon 1 | 1.26 |
| CDC14B | cell division cycle 14B | 1.474 |
| CLU | Clusterin | 1.854 |
| CMTM5 | CKLF-like MARVEL transmembrane domain containing 5 | 1.429 |
| CPNE5 | copine V | 1.879 |
| CTDSPL | CTD (carboxy-terminal domain, RNA polymerase II, polypeptide A) small phosphatase-like | 1.495 |
| CTTN | Cortactin | 1.443 |
| ELOVL7 | ELOVL family member 7, elongation of long chain fatty acids (yeast) | 1.384 |
| FRMD3 | FERM domain containing 3 | 1.35 |
| FSTL1 | follistatin-like 1 | 1.748 |
| GNG11 | guanine nucleotide binding protein (G protein), gamma 11 | 1.383 |
| GP1BB | glycoprotein Ib (platelet), beta polypeptide | 1.432 |
| GUCY1B3 | guanylate cyclase 1, soluble, beta 3 | 1.551 |
| IGF2BP3 | insulin-like growth factor 2 mRNA binding protein 3 | 1.347 |
| ITGA2B | integrin, alpha 2b (platelet glycoprotein IIb of IIb/IIIa complex, antigen CD41) | 1.663 |
| ITGB3 | integrin, beta 3 (platelet glycoprotein IIIa, antigen CD61) | 1.883 |
| MMD | monocyte to macrophage differentiation-associated | 1.29 |
| MPL | myeloproliferative leukemia virus oncogene | 1.883 |
| MYL9 | myosin, light chain 9, regulatory | 1.543 |
| MYLK | myosin, light chain kinase | 1.525 |
| PBX1 | pre-B-cell leukemia transcription factor 1 | 1.464 |
| PCSK6 | proprotein convertase subtilisin/kexin type 6 | 1.805 |
| PDE5A | phosphodiesterase 5A, cGMP-specific | 1.485 |
| PF4 | platelet factor 4 (chemokine (C—X—C motif) ligand 4) | 1.416 |
| PPBP | pro-platelet basic protein (chemokine (C—X—C motif) ligand 7) | 1.467 |
| PRKAR2B | protein kinase, cAMP-dependent, regulatory, type II, beta | 1.346 |
| RUNX1 | Runt-related transcription factor 1 | 1.331 |
| SDPR | serum deprivation response (phosphatidylserine binding protein) | 1.732 |
| SELP | selectin P (granule membrane protein 140 kDa, antigen CD62) | 1.543 |
| SH3BGRL2 | SH3 domain binding glutamic acid-rich protein like 2 | 1.44 |
| SLC24A3 | solute carrier family 24 (sodium/potassium/calcium exchanger), member 3 | 1.315 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for determining risk of death and/or myocardial infarction in a human subject, the method comprising:
   (a) obtaining a blood sample from the subject;
   (b) determining the gene expression level of at least one biomarker of platelet function selected from the group consisting of ALOX12, ARHGAP18, C12orf39, CALD1, CLEC1B, CLEC4D, CLU, CMTM5, CTDSPL, ELOVL7, ENDOD1, FRMD3, FSTL1, GNG11, GP1BB, HIST1H2AG, HIST1H2BG, HIST1H3H, IGF2BP3, ITGA2B, ITGB3, LGALSL, MGLL, MYL9, PARVB, PBX1, PCGF5, PCSK6, PDE5A, PF4, PPBP, PRKAR2B, PROS1, SELP, SH3BGRL2, SLC24A3, SPARC, TGFB1I1, THBS1, TPM1, TREML1, TTC7B, and TUBB1 in the blood sample from the subject, wherein the gene expression level is determined by measuring the mRNA level;
   (c) identifying the subject as being at risk of death and/or myocardial infarction when the gene expression level of the at least one biomarker of platelet function in the sample is greater than the reference level of the at least one biomarker of platelet function,
   wherein the reference level is the level of the at least one biomarker of platelet function in a healthy subject, or a subject without cardiovascular disease, or a subject having cardiovascular disease but who has not suffered death or myocardial infarction; and
   (d) administering an antiplatelet agent to the subject identified as being at risk of death and/or myocardial infarction.

2. The method of claim 1, wherein the reference level of the at least one biomarker of platelet function is the cutoff value of the at least one biomarker of platelet function determined by measuring a change in gene expression levels between blood samples obtained before and after aspirin treatment of a healthy patient group or patients without cardiovascular disease.

3. The method of claim 1, wherein the at least one biomarker of platelet function is selected from the group consisting of C12orf39, CLEC4D, CLU, ENDOD1, FRMD3, GP1BB, HIST1H2BG, HIST1H3H, IGF2BP3, ITGA2B, MYL9, PBX1, PCGF5, PPBP, PRKAR2B, PROS1, SELP, SH3BGRL2, TGFB1I1, THBS1, TPM1, TREML1, and TTC7B.

4. The method of claim 1, wherein the at least one biomarker of platelet function is selected from the group consisting of ITGA2B, ENDOD1, PBX1, LGALSL, TPM1, ITGB3, THBS1, HIST1H3H, and FRMD3.

* * * * *